(12) United States Patent
Takahashi et al.

(10) Patent No.: US 7,645,756 B2
(45) Date of Patent: Jan. 12, 2010

(54) NITROGENOUS FUSED HETEROAROMATIC RING DERIVATIVE

(75) Inventors: Toshiyuki Takahashi, Tsukuba (JP); Akio Kanatani, Ushiku (JP); Shigeru Tokita, Tsukuba (JP); Ryo Yoshimoto, Tsukuba (JP)

(73) Assignee: Banyu Pharmaceutical Co. Ltd., Tokyo (JP)

( * ) Notice: Subject to any disclaimer, the term of this patent is extended or adjusted under 35 U.S.C. 154(b) by 355 days.

(21) Appl. No.: 10/589,832

(22) PCT Filed: Feb. 17, 2005

(86) PCT No.: PCT/JP2005/002948

§ 371 (c)(1), (2), (4) Date: Aug. 17, 2006

(87) PCT Pub. No.: WO2005/077953

PCT Pub. Date: Aug. 25, 2005

(65) Prior Publication Data

US 2007/0167453 A1    Jul. 19, 2007

(30) Foreign Application Priority Data

Feb. 18, 2004    (JP)    ............................. 2004-042171

(51) Int. Cl.
C07D 487/04    (2006.01)
A61K 31/5025   (2006.01)
A61K 31/53     (2006.01)
A61P 3/04      (2006.01)
A61P 3/10      (2006.01)
A61P 9/10      (2006.01)

(52) U.S. Cl. ..................... 514/248; 514/243; 544/236; 544/184

(58) Field of Classification Search ................. 544/236; 514/248
See application file for complete search history.

(56) References Cited

U.S. PATENT DOCUMENTS 4,810,705 A    3/1989    Bourguignon et al.
5,011,835 A    4/1991    Peet et al.

FOREIGN PATENT DOCUMENTS

EP    1243271    9/2002

OTHER PUBLICATIONS

Hancock et al., Expert Opin. Investig. Drugs, 14(3), 223-241, 2005.*
Razvi, Mehboob et al., Synthesis and biological activity of 3,6-diaryl-1,2,4-triazolo[3, 4-a]phthalazines, Indian Journal of Chemistry, Section B: Organic Chemistry Including Medicinal Chemistry, vol. 28B, No. 11, pp. 987 to 989, 1989.
Lieberman, Daniel F. et al., A new and improved synthesis of 6-aryl-1,2,4-triazolo[4,3-b]pyridazines, Journal of Heterocyclic Chemistry, vol. 25, No. 3, pp. 827 to 830, 1988.

* cited by examiner

*Primary Examiner*—Venkataraman Balasubramanian
(74) *Attorney, Agent, or Firm*—J. Eric Thies; William Krovatin

(57) ABSTRACT

The invention provides a compound or its pharmaceutically-acceptable salt of formula

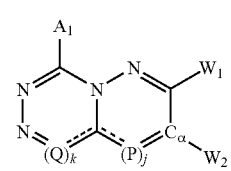

(I)

wherein $A_1$ is a hydrogen, etc.; j and k are 0 or 1;
$==(P)_j==$
is a double bond, etc.;
$==(Q)_k==$
is a double bond, etc.;
one of $W_1$ and $W_2$ is E—O—W, etc., and the other is a hydrogen atom, etc.; E is a divalent group derived from a benzene ring, etc., by removing two hydrogen atoms therefrom; W is a group of formula (II-1):

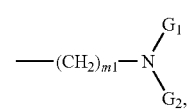

(II-1)

which has a histamine-H3 receptor antagonistic effect or a histamine-H3 receptor inverse-agonistic effect and is useful for prevention or remedy of metabolic system diseases, circulatory system diseases or nervous system diseases.

19 Claims, No Drawings

NITROGENOUS FUSED HETEROAROMATIC RING DERIVATIVE

CROSS REFERENCE TO RELATED APPLICATIONS

This application is a U.S. National Phase application under 35 U.S.C. §371 of PCT Application No. PCT/JP2005/002948, filed Feb. 17, 2005, which claims priority under 35 U.S.C. §119 from IP Application No. JP2004-042171, filed Feb. 18, 2004.

TECHNICAL FIELD

The present invention relates to nitrogen-containing condensed hetero-aromatic ring derivatives.

BACKGROUND ART

It has been known that, in organisms such as typically mammals, histamine that is a physiologically-active endogenous factor functions as a neurotransmitter and has extensive pharmacological activities (for example, see *Life Science*, Vol. 17, p. 503 (1975)).

Immunohistochemical studies have made it clear that a histamine-agonistic (producing) cell body exists in the nodal papillary nucleus in a posterior hypothalamic region and that histamine-agonistic nerve fibers project histamine in an extremely broad range in the brain, which supports various pharmacological effects of histamine (for example, see *Journal of Comprehensive Neurology*, Vol. 273, p. 283).

The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action, etc.) (for example, see *Progress in Neurobiology*, Vol. 63, p. 637 (2001)).

The projection of histamine-agonistic nerve fibers to the brain region that relates to vigilance sustenance (e.g., cerebral cortex) suggests the role of histamine in control of vigilance or vigilance-sleep cycle. The projection of histamine-agonistic nerve fibers to many peripheral structures such as hippocampus and amygdaloid complex suggests the role of histamine in control of autonomic nerves, emotion, control of motivated action and learning/memory process.

When released from producing cells, histamine acts with a specific polymer that is referred to as a receptor on the surface of a cell membrane or inside a target cell, therefore exhibiting its pharmacological effects for control of various body functions. Heretofore, four types of histamine receptors have been found. In particular, the presence of a histamine receptor that participates in the central and peripheral nervous functions, a histamine-H3 receptor, has been shown by various pharmacological and physiological studies (for example, see *Trends in Pharmacological Science*, Vol. 8, p. 24 (1986)). Recently, human and rodent histamine-H3 receptor genes have been identified and their existence has been revealed (for example, see *Molecular Pharmacology*, Vol. 55, p. 1101 (1999)).

The histamine-H3 receptor exists in the presynaptic membrane of central or peripheral neurocytes and functions as a self-receptor, therefore controlling the release of histamine and controlling the release of other neurotransmitters. Specifically, a histamine-H3 receptor agonist, or its antagonist or inverse-agonist controls the release of histamine, noradrenaline, serotonin, acetylcholine or dopamine from nerve ending. The release of these neurotransmitters is inhibited by a histamine-H3 receptor agonist such as (R)-(α)-methylhistamine, and is promoted by a histamine-H3 receptor antagonist or inverse-agonist such as thioperamide (for example, see *Trends in Pharmacological Science*, Vol. 19, p. 177 (1998)).

DISCLOSURE OF THE INVENTION

An object of the invention is to provide a novel substance having a histamine-H3 receptor antagonistic effect (an effect of inhibiting histamine from binding to a histamine-H3 receptor) or a histamine-H3 receptor inverse-agonistic effect (an effect of inhibiting the homeostatic activity that a histamine-H3 receptor has), or that is, a novel substance that acts as a histamine-H3 receptor agonist or antagonist in living bodies.

The present inventors have found that a specific nitrogen-containing condensed hetero-aromatic derivative acts as a histamine-H3 receptor antagonist or inverse-agonist, and have completed the invention.

Accordingly, for attaining the above object, the invention provides compounds or salts of the following (1) to (20):

(1) A compound or its pharmaceutically-acceptable salt of a formula (I):

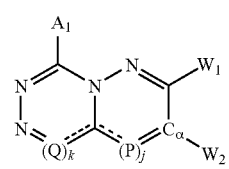

(I)

in the formula, $A_1$ represents a hydrogen atom, a group selected from a substituent group P optionally having 1 or 2 groups selected from a substituent group α, or a phenyl or heteroaryl group which are optionally having 1 or 2 groups selected from a substituent group γ; j and k each independently indicate 0 or 1; when j is 0, then a formula (III-1):

in the formula (I) represents a double bond, and when j is 1, then the formula (III-1) represents a group of:

$$-\underset{A_2}{\overset{\phantom{|}}{\text{C}}}=$$

(wherein $A_2$ has the same meaning as $A_1$); when k is 0, then a formula (III-2):

in the formula (I) represents a double bond, and when k is 1, then the formula (III-2) represents a group of:

$$=\underset{A_3}{\overset{\phantom{|}}{\text{C}}}-$$

(wherein $A_3$ has the same meaning as $A_1$); regarding $W_1$ and $W_2$, one of $W_1$ and $W_2$ is $A_4$ and the other is E—O—W, or when j is 1, then $W_1$ may be E—O—W and $A_2$—C=C—$W_2$ may together form a benzene ring or a heteroaryl ring having from 1 to 3, the same or different hetero atoms selected from a group consisting of a nitrogen atom, a sulfur atom and an oxygen atom (the benzene ring and the heteroaryl ring may be substituted with a nitro group, a hydroxy group, a lower alkyl group, a halo-lower alkyl group, a halogen atom, a lower alkoxy group, an alkanoylamino group); E represents a phenyl group optionally having from 1 to 3 groups selected from a substituent group δ, or a 5- or 6-membered monocyclic aromatic heterocyclic group having 1 or more, preferably from 1 to 3, the same or different hetero atoms selected from a group consisting of a nitrogen atom, an oxygen atom and a sulfur atom, or represents a condensed-cyclic aromatic heterocyclic group that the monocyclic aromatic heterocyclic group forms together with an aryl group; W represents a formula (II-1):

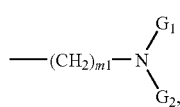

(II-1)

a formula (II-2):

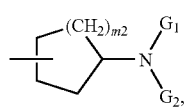

(II-2)

or a formula (II-3):

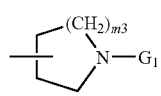

(II-3)

(wherein $G_1$ and $G_2$ may be the same or different, each representing a lower alkyl group (the lower alkyl group may be further substituted with a halogen atom) or a cycloalkyl group, or $G_1$ and $G_2$ form, together with the nitrogen atom adjacent to $G_1$ and $G_2$, a 5- to 8-membered aliphatic hetero-ring (the hetero-ring may have, in the ring, 1 or 2 groups of a lower alkyl group optionally substituted with a halogen atom or a halogen atom) or a bicyclo-ring; m1 indicates an integer of from 2 to 4; m2 and m3 each indicate an integer of from 1 to 3; $(CH_2)m1$ in the formula (II-1) may be further substituted with a lower alkyl group having from 1 to 3 carbon atoms;

Substituent group α: an amino group, a nitro group, a cyano group, a hydroxy group, a halogen atom, a lower alkylsulfonyl group, a lower alkyl group (the lower alkyl group may be substituted with a halogen atom), a lower cycloalkyl group (the lower cycloalkyl group may be substituted with a halogen atom), a lower alkoxy group (the lower alkoxy group may be substituted with a halogen atom), a lower cycloalkoxy group (the lower cycloalkoxy group may be substituted with a halogen atom), an aryloxy group, an alaryloxy group, an aryl group, a heteroaryl group, a mono-lower alkylcarbamoyl group, a di-lower alkylcarbamoyl group, a lower alkylcarboxamido group, an arylcarboxamido group, a heteroarylcarboxamido group, an alkanoyl group, an alkylthio group;

Substituent group β: an amino group, a lower alkylsulfonyl group, a lower alkyl group, a lower cycloalkyl group, a lower alkoxy group, a lower cycloalkoxy group, the lower alkyl group being optionally substituted with a halogen atom, a lower cycloalkyl group (the cycloalkyl group may be substituted with a halogen atom), a lower alkoxy group (the lower alkoxy group may be substituted with a halogen atom), a lower cycloalkoxy group (the lower cycloalkoxy group may be substituted with a halogen atom), a carbamoyl group, a mono- or di-lower alkylcarbamoyl group;

Substituent group γ: an amino group, a nitro group, a cyano group, a hydroxy group, a lower alkylsulfonyl group, a halogen atom, a lower alkyl group (the lower alkyl group may be substituted with a halogen atom), a lower cycloalkyl group (the lower alkyl group may be substituted with a halogen atom), a lower alkoxy group (the lower alkoxy group may be substituted with a halogen atom or a hydroxy group), a lower cycloalkoxy group (the lower alkyl group may be substituted with a halogen atom), an aryloxy group, an alaryloxy group, an aryl group, a heteroaryl group, a mono-lower alkylcarbamoyl group, a di-lower alkylcarbamoyl group, a lower alkylcarboxamido group, an arylcarboxamido group, a heteroarylcarboxamido group, an alkanoyl group, an alkylthio group, an alkoxycarbonylamino group, an alkylsulfonylamino group, an arylsulfonylamino group, an alkylaminosulfonyl group or an arylaminosulfonyl group;

Substituent group δ: a halogen atom, a nitro group, a lower alkyl group, a halo-lower alkyl group, a hydroxy group, a hydroxy-lower alkyl group, a cyclo-lower alkyl group, a lower alkenyl group, a hydroxyl group, a lower alkoxy group, a halo-lower alkoxy group, a lower alkylamino group, a di-lower alkylamino group, a lower alkylthio group, a carboxyl group, a lower alkanoyl group, a lower alkoxycarbonyl group.

(2) The compound or its pharmaceutically-acceptable salt of (1), wherein $A_1$ is a hydrogen atom, a lower alkyl group (the lower alkyl group may be substituted with a halogen atom), a lower alkoxy group, a phenyl group, a pyridyl group, a carbamoyl group, a mono- or di-lower alkylcarbamoyl group, and $A_2$, $A_3$ and $A_4$ each are independently a hydrogen atom or a lower alkyl group.

(3) The compound or its pharmaceutically-acceptable salt of (1) or (2), wherein one of $W_1$ and $W_2$ is $A_4$, and the other is E—O—W; or when j is 1, then $W_1$ is E—O—W, and $A_2$—C=C—$W_2$ together forms a benzene ring or a heteroaryl ring having 1 or 2 nitrogen atoms in the ring.

(4) The compound or its pharmaceutically-acceptable salt of (2) or (3), wherein E is a phenyl group, a pyridyl group, a pyrimidinyl group, a pyridazinyl group or a pyrazinyl group.

(5) The compound or its pharmaceutically-acceptable salt of (2) or (3), wherein E is a phenyl group or a pyridyl group.

(6) The compound or its pharmaceutically-acceptable salt of (2) or (3), wherein E is a phenyl group.

(7) The compound or its pharmaceutically-acceptable salt of (1), (2), (3), (4), (5) or (6), wherein W is the formula (II-1) or (II-3).

(8) The compound or its pharmaceutically-acceptable salt of (1), (2) or (3), wherein the formula (I) is the following formula (I-0):

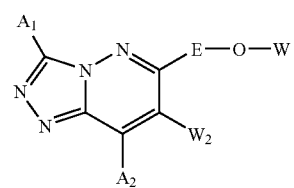

(I-0)

[in the formula, the symbols have the same meanings as above].

(9) The compound or its pharmaceutically-acceptable salt of (1), (2) or (3), wherein the formula (I) is the following formula (I-1):

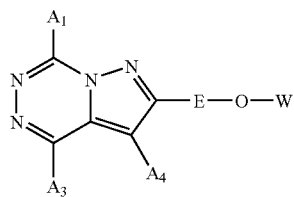

(I-1)

[in the formula, the symbols have the same meanings as above].

(10) The compound or its pharmaceutically-acceptable salt of (1), (2) or (3), wherein the formula (I) is the following formula (I-2):

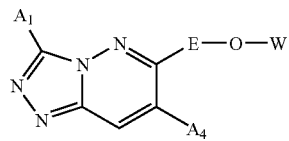

(I-2)

(11) The compound or its pharmaceutically-acceptable salt of (1), (2) or (3), wherein the formula (I) is the following formula (I-3):

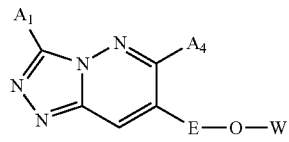

(I-3)

(12) The compound or its pharmaceutically-acceptable salt of (1), (2) or (3), wherein the formula (I) is the following formula (I-4):

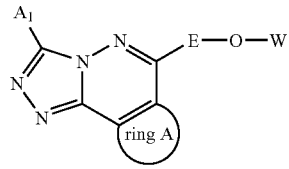

(I-4)

in the formula, ring A represents a benzene ring or a heteroaryl ring having 1 or 2 nitrogen atoms in the ring (the benzene ring and the heteroaryl ring may be substituted with a nitro group, a hydroxyl group, a lower alkyl group, a halo-lower alkyl group, a halogen atom, a lower alkoxy group, an alkanoylamino group).

(13) The compound or its pharmaceutically-acceptable salt of (12), wherein the ring A is a benzene ring or a pyridine ring.

(14) The compound or its pharmaceutically-acceptable salt of (1), wherein the formula (I) is:
2-[4-(3-piperidin-1-ylpropoxy)-phenyl]-3aH-pyrazolo[1,5-d][1,2,4]triazine,
2-[4-(1-cyclopentyl-piperidin-4-yloxy)phenyl]-3aH-pyrazolo[1,5-d][1,2,4]triazine trifluoroacetate,
3-methyl-2-[4-(3-piperidin-1-ylpropoxy)-phenyl]-3aH-pyrazolo[1,5-d][1,2,4]triazine,
3-ethyl-2-[4-(3-piperidin-1-ylpropoxy)phenyl]-3aH-pyrazolo[1,5-d][1,2,4]triazine,
7-methyl-2-[4-(3-piperidin-1-ylpropoxy)-phenyl]-3aH-pyrazolo[1,5-d][1,2,4]triazine,
7-(5-methyl-isoxazol-3-yl)-2-[4-(3-piperidin-1-ylpropoxy)-phenyl]-3aH-pyrazolo[1,5-d][1,2,4]triazine,
7-phenyl-2-[4-(3-piperidin-1-ylpropoxy)-phenyl]-3aH-pyrazolo[1,5-d][1,2,4]triazine,
3-methyl-7-phenyl-2-[4-(3-piperidin-1-ylpropoxy)-phenyl]-3aH-pyrazolo[1,5-d][1,2,4]triazine,
3-methyl-2-[4-(3-piperidin-1-ylpropoxy)-phenyl]-7-(pyridin-3-yl)-3aH-pyrazolo[1,5-d][1,2,4]triazine,
6-[4-(3-piperidin-1-ylpropoxy)-phenyl]-[1,2,4]triazolo[4,3-b]pyridazine,
7-methyl-6-[4-(3-piperidin-1-ylpropoxy)-phenyl]-[1,2,4]triazolo[4,3-b]pyridazine,
3-methyl-6-[4-(3-piperidin-1-ylpropoxy)-phenyl]-[1,2,4]triazolo[4,3-b]pyridazine,
6-[4-(3-piperidin-1-ylpropoxy)-phenyl]-3-trifluoromethyl-[1,2,4]triazolo[4,3-b]pyridazine,
3-tert-butyl-6-[4-(3-piperidin-1-ylpropoxy)-phenyl]-[1,2,4]triazolo[4,3-b]pyridazine,
3-phenyl-6-[4-(3-piperidin-1-ylpropoxy)-phenyl]-[1,2,4]triazolo[4,3-b]pyridazine,
6-[4-(3-piperidin-1-ylpropoxy)-phenyl]-3-(pyridin-2-yl)-[1,2,4]triazolo[4,3-b]pyridazine,
6-[4-(3-piperidin-1-ylpropoxy)-phenyl]-3-(pyridin-3-yl)-[1,2,4]triazolo[4,3-b]pyridazine,
7-methyl-3-phenyl-6-[4-(3-piperidin-1-ylpropoxy)-phenyl]-[1,2,4]triazolo[4,3-b]pyridazine,
6-methyl-7-[4-(3-piperidin-1-ylpropoxy)-phenyl]-[1,2,4]triazolo[4,3-b]pyridazine,
3,6-dimethyl-7-[4-(3-piperidin-1-ylpropoxy)-phenyl]-[1,2,4]triazolo[4,3-b]pyridazine,
6-methyl-3-phenyl-[4-(3-piperidin-1-ylpropoxy)-phenyl]-[1,2,4]triazolo[4,3-b]pyridazine,
6-[4-(3-piperidin-1-ylpropoxy)-phenyl]-pyrido[3,2-d][1,2,4]triazolo[4,3-b]pyridazine,
4-(pyrido[3,2-d][1,2,4]triazolo[4,3-b]pyridazin-6-yl)-phenol,
4-(pyrido[2,3-d][1,2,4]triazolo[4,3-b]pyridazin-6-yl)-phenol,
3-phenyl-6-[4-(3-piperidin-1-ylpropoxy)-phenyl]-pyrido[2,3-d][1,2,4]triazolo[4,3-b]pyridazine,
3-phenyl-6-[6-(3-piperidin-1-ylpropoxy)-pyridin-3-ylmethoxy]-[1,2,4]triazolo[3,4-a]phthalazine,
3-phenyl-6-[4-(3-piperidin-1-ylpropoxy)-phenyl]-[1,2,4]triazolo[3,4-a]phthalazine,
6-[4-(3-piperidin-1-ylpropoxy)-phenyl]-3-(pyridin-3-yl)-[1,2,4]triazolo[3,4-a]phthalazine,
6-[4-(3-piperidin-1-ylpropoxy)-phenyl]-3-(pyridin-2-yl)-[1,2,4]triazolo[3,4-a]phthalazine,
3-phenyl-6-[4-(3-piperidin-1-ylpropoxy)-phenyl]-pyrido[3,2-d][1,2,4]triazolo[4,3-b]pyridazine,
6-[4-(3-piperidin-1-ylpropoxy)-phenyl]-pyrido[2,3-d][1,2,4]triazolo[4,3-b]pyridazine,
3-methyl-6-[4-(3-piperidin-1-ylpropoxy)-phenyl]-pyrido[3,2-d][1,2,4]triazolo[4,3-b]pyridazine, 3-methyl-6-[4-(3-piperidin-1-ylpropoxy)-phenyl]-pyrido[2,3-d][1,2,4]triazolo[4,3-b]pyridazine,
6-[4-(3-piperidin-1-ylpropoxy)-phenyl]-[1,2,4]triazolo[3,4-a]phthalazine,
3-methyl-6-[4-(3-piperidin-1-ylpropoxy)-phenyl]-[1,2,4]triazolo[3,4-a]phthalazine,
6-[4-(3-piperidin-1-ylpropoxy)-phenyl]-3-trifluoromethyl-[1,2,4]triazolo[3,4-a]phthalazine,
3-tert-butyl-6-[4-(3-piperidin-1-ylpropoxy)-phenyl]-[1,2,4]triazolo[3,4-a]phthalazine,
6-[4-(1-cyclopentyl-piperidin-4-yloxy)-phenyl]-[1,2,4]triazolo[4,3-b]pyridazine,
6-[4-(1-cyclobutyl-piperidin-4-yloxy)-phenyl]-[1,2,4]triazolo[4,3-b]pyridazine,
6-[4-(1-cyclopentyl-piperidin-4-yloxy)-phenyl]-3-methyl-[1,2,4]triazolo[4,3-b]pyridazine,
6-[4-(1-cyclopentyl-piperidin-4-yloxy)-phenyl]-7-methyl-[1,2,4]triazolo[4,3-b]pyridazine,
7-[4-(3-piperidin-1-ylpropoxy)-phenyl]-[1,2,4]triazolo[4,3-b]pyridazine,
7-[4-(1-cyclopentyl-piperidin-4-yloxy)-phenyl]-3-methyl-[1,2,4]triazolo[4,3-b]pyridazine,
7-[4-(1-cyclopentyl-piperidin-4-yloxy)-phenyl]-6-methyl-[1,2,4]triazolo[4,3-b]pyridazine,
7-[4-(1-cyclopentyl-piperidin-4-yloxy)-phenyl]-3,6-dimethyl-[1,2,4]triazolo[4,3-b]pyridazine,
7-[4-(1-cyclopentyl-piperidin-4-yloxy)-phenyl]-[1,2,4]triazolo[4,3-b]pyridazine,
7-[4-(1-cyclobutyl-piperidin-4-yloxy)-phenyl]-[1,2,4]triazolo[4,3-b]pyridazine,
6-[4-(1-cyclopentyl-piperidin-4-yloxy)-phenyl]-[1,2,4]triazolo[3,4-a]phthalazine,
6-[4-(1-cyclopentyl-piperidin-4-yloxy)-phenyl]-3-methyl-[1,2,4]triazolo[3,4-a]phthalazine,
6-[4-(3-pyrrolidin-1-ylpropoxy)-phenyl]-[1,2,4]triazolo[4,3-b]pyridazine,
3-methyl-7-[4-(3-piperidin-1-ylpropoxy)-phenyl]-[1,2,4]triazolo[4,3-b]pyridazine,
7-[4-(1-cyclobutyl-piperidin-4-yloxy)-phenyl]-3-methyl-[1,2,4]triazolo[4,3-b]pyridazine,
6-[4-(1-cyclobutyl-piperidin-4-yloxy)-phenyl]-3-methyl-[1,2,4]triazolo[4,3-b]pyridazine,
6-[4-(1-cyclobutyl-piperidin-4-yloxy)-phenyl]-[1,2,4]triazolo[3,4-a]phthalazine,
6-[4-(1-cyclobutyl-piperidin-4-yloxy)-phenyl]-7-methyl-[1,2,4]triazolo[4,3-b]pyridazine,
7-[4-(1-cyclobutyl-piperidin-4-yloxy)-phenyl]-6-methyl-[1,2,4]triazolo[4,3-b]pyridazine,
7-[4-(1-cyclobutyl-piperidin-4-yloxy)-phenyl]-3,6-dimethyl-[1,2,4]triazolo[4,3-b]pyridazine,
6-[4-(1-cyclobutyl-piperidin-4-yloxy)-phenyl]-3-methyl-[1,2,4]triazolo[3,4-a]phthalazine,
6-{4-[3-(2,6-dimethylpiperizin-1-yl)propoxy]-phenyl}-[1,2,4]triazolo[4,3-b]pyridazine,
6-{4-[3-(2,5-dimethylpyrrolidin-1-yl)propoxy]-phe,
N-methyl-6-[4-(3-piperidin-1-ylpropoxy)phenyl]-[1,2,4]triazolo[4,3-b]pyridazine-3-carboxamide,
3-(piperidin-1-ylcarbonyl)-6-[4-(3-piperidin-1-ylpropoxy)phenyl]-[1,2,4]triazolo[4,3-b]pyridazine,
6-[4-(3-methylpiperidin-1-ylpropoxy)-phenyl]-[1,2,4]triazolo[4,3-b]pyridazine,
6-[4-{3-[(3S)-3-fluoropyrrolidin-1-yl]propoxy}-phenyl)-[1,2,4]triazolo[4,3-b]pyridazine,
6-{4-[3-(3-methylpiperidin-1-yl)propoxy]-phenyl}-[1,2,4]triazolo[4,3-b]pyridazine,
6-{4-[3-(4-fluoropiperidin-1-yl)propoxy]-phenyl}-[1,2,4]triazolo[4,3-b]pyridazine,
6-{4-[3-(3-fluoropiperidin-1-yl)propoxy]-phenyl}-[1,2,4]triazolo[4,3-b]pyridazine,
6-[4-{3-[(2R)-(2-methylpyrrolidin-1-yl]propoxy}-phenyl}-[1,2,4]triazolo[4,3-b]pyridazine,
6-[4-{3-[(2S)-(2-methylpyrrolidin-1-yl]propoxy}-phenyl}-[1,2,4]triazolo[4,3-b]pyridazine,
N,N-dimethyl-6-[4-{3-[(2R)-2-methylpyrrolidin-1-yl]propoxy)-phenyl}-[1,2,4]triazolo[3,4-a]phthalazine-3-carboxamide,
6-[4-(3-piperidin-1-ylpropoxy)-phenyl]-pyrido[3,4-d][1,2,4]triazolo[4,3-b]pyridazine,
6-[4-(3-pyrrolidin-1-ylpropoxy)-phenyl]-pyrido[3,4-d][1,2,4]triazolo[4,3-b]pyridazine,
6-[4-{3-[(3S)-3-methylpiperidin-1-yl]propoxy}-phenyl]-pyrido[3,4-d][1,2,4]triazolo[4,3-b]pyridazine,
3-methyl-6-[4-(3-piperidin-1-ylpropoxy)-phenyl]-pyrido[3,4-d][1,2,4]triazolo[4,3-b]pyridazine,
3-methyl-6-[4-(3-pyrrolidin-1-ylpropoxy)-phenyl]-pyrido[3,4-d][1,2,4]triazolo[4,3-b]pyridazine,
3-methyl-6-[4-{3-[(3S)-3-methylpiperidin-1-yl]propoxy}-phenyl]-pyrido[3,4-d][1,2,4]triazolo[4,3-b]pyridazine,
6-[4-{3-[(2R)-2-methylpyrrolidin-1-yl]propoxy}-phenyl]-pyrido[3,4-d][1,2,4]triazolo[4,3-b]pyridazine,
3-methyl-6-[4-{3-[(2R)-2-methylpyrrolidin-1-yl]propoxy}-phenyl]-pyrido[3,4-d][1,2,4]triazolo[4,3-b]pyridazine,
6-[4-(1-isopropylpiperidin-4-yloxy)phenyl]pyrido[3,4-d][1,2,4]triazolo[4,3-b]pyridazine,
6-[4-(1-cyclobutylpiperidin-4-yloxy)phenyl]pyrido[3,4-d][1,2,4]triazolo[4,3-b]pyridazine,
6-[4-(1-cylopentylpiperidin-4-yloxy)phenyl]pyrido[3,4-d][1,2,4]triazolo[4,3-b]pyridazine,
6-[4-(1-isopropylpiperidin-4-yloxy)phenyl]-3-methyl-pyrido[3,4-d][1,2,4]triazolo[4,3-b]pyridazine,
6-[4-(1-cyclobutylpiperidin-4-yloxy)phenyl]-3-methylpyrido[3,4-d][1,2,4]triazolo[4,3-b]pyridazine,
6-[4-(1-cyclopentylpiperidin-4-yloxy)phenyl]-3-methylpyrido[3,4-d][1,2,4]triazolo[4,3-b]pyridazine,
3-methyl-6-[4-(3-pyrrolidin-1-ylpropoxy)-phenyl]-pyrido[3,2-d][1,2,4]triazolo[4,3-b]pyridazine,
3-methyl-6-[4-(3-pyrrolidin-1-ylpropoxy)-phenyl]-pyrido[2,3-d][1,2,4]triazolo[4,3-b]pyridazine,
3-methyl-6-(4-{3-[(3S)-3-methylpiperidin-1-yl]propoxy}-phenyl]-pyrido[3,2-d][1,2,4]triazolo[4,3-b]pyridazine,
3-methyl-6-(4-{3-[(3S)-3-methylpiperidin-1-yl]propoxy}-phenyl]-pyrido[2,3-d][1,2,4]triazolo[4,3-b]pyridazine,
3-methyl-6-(4-{3-[(2R)-3-methylpyrrolidin-1-yl]propoxy}-phenyl]-pyrido[3,2-d][1,2,4]triazolo[4,3-b]pyridazine,
3-methyl-6-(4-{3-[(2R)-3-methylpyrrolidin-1-yl]propoxy}-phenyl]-pyrido[2,3-d][1,2,4]triazolo[4,3-b]pyridazine,
6-[4-(1-isopropylpiperidin-4-yloxy)phenyl]-3-methylpyrido[3,2-d][1,2,4]triazolo[4,3-b]pyridazine,
6-[4-(1-isopropylpiperidin-4-yloxy)phenyl]-3-methylpyrido[2,3-d][1,2,4]triazolo[4,3-b]pyridazine,
6-[4-(1-cyclobutylpiperidin-4-yloxy)phenyl]-3-methylpyrido[3,2-d][1,2,4]triazolo[4,3-b]pyridazine,
6-[4-(1-cyclobutylpiperidin-4-yloxy)phenyl]-3-methylpyrido[2,3-d][1,2,4]triazolo[4,3-b]pyridazine,
6-[4-(1-cyclopentylpiperidin-4-yloxy)phenyl]-3-methylpyrido[3,2-d][1,2,4]triazolo[4,3-b]pyridazine,
6-[4-(1-cyclopentylpiperidin-4-yloxy)phenyl]-3-methylpyrido[2,3-d][1,2,4]triazolo[4,3-b]pyridazine,
6-[4-(1-isopropylpiperidin-4-yloxy)phenyl]pyrido[3,2-d][1,2,4]triazolo[4,3-b]pyridazine,
6-[4-(1-isopropylpiperidin-4-yloxy)phenyl]pyrido[2,3-d][1,2,4]triazolo[4,3-b]pyridazine,
6-[4-(1-cyclobutylpiperidin-4-yloxy)phenyl]pyrido[3,2-d][1,2,4]triazolo[4,3-b]pyridazine, 6-[4-(1-cyclobutylpiperidin-4-yloxy)phenyl]pyrido[2,3-d][1,2,4]triazolo[4,3-b]pyridazine, 6-[4-(1-cyclopentylpiperidin-4-yloxy)phenyl]pyrido[3,2-d][1,2,4]triazolo[4,3-b]pyridazine, 6-[4-(1-cyclopentylpiperidin-4-yloxy)phenyl]pyrido[2,3-d][1,2,4]triazolo[4,3-b]pyridazine, 6-[6-(3-piperidin-1-ylpropoxy)pyridin-3-yl]-[1,2,4]triazolo[3,4-a]phthalazine or 6-{6-[(3S)-3-piperidin-1-ylpropoxy]pyridin-3-yl}-[1,2,4]triazolo[3,4-a]phthalazine.

(15) A histamine receptor-H3 antagonist containing, as the active ingredient thereof, a compound of any one of (1) to (14).

(16) A histamine receptor-H3 inverse-agonist described in any one of (1) to (14).

(17) A preventive or remedy containing, as the active ingredient thereof, a compound or its pharmaceutically-acceptable salt of any of (1) to (14), which is for metabolic system diseases, circulatory system diseases or nervous system diseases.

(18) The preventive or remedy of (17), wherein the metabolic system diseases are at least one selected from obesity, diabetes, hormone secretion disorder, hyperlipemia, gout and fatty liver.

(19) The preventive or remedy of (17), wherein the circulatory system diseases are at least one selected from stenocardia, acute/congestive cardiac insufficiency, cardiac infarction, coronary arteriosclerosis, hypertension, nephropathy and electrolyte metabolism disorder.

(20) The preventive or remedy of (17), wherein the nervous system diseases are at least one selected from sleep disorder and diseases accompanied by sleep disorder, bulimia, emotional disorder, epilepsy, delirium, dementia, attention deficit/hyperactivity disorder, memory disorder, Alzheimer's disease, Parkinson's disease, recognition disorder, motion disorder, paresthesia, dysosmia, morphine resistance, narcotic dependency, alcoholic dependency and tremor.

(21) The preventive or remedy of (17), wherein the nervous system diseases are at least one selected from idiopathic hypersomnnia, repetitive hypersomnia, true hypersomnnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, melancholia, anxiety, schizophrenia.

(22) A preventive or remedy for metabolic system diseases, circulatory system diseases or nervous system diseases, which contains, as the active ingredients thereof, the compound or its pharmaceutically-acceptable salt of any one of (1) to (14) and an additional drug.

The compounds or their salts of above (1) to (14) act as a histamine-H3 receptor antagonist or inverse-agonist in living bodies. Accordingly, the invention provides a histamine-H3 receptor antagonist or inverse-agonist comprising the compound or its pharmaceutically-acceptable salt of above (1) to (14).

Recent studies have shown that a histamine-H3 receptor has extremely high homeostatic activities (activities observed in the absence of endogenous agonistic factor (e.g., histamine)) in the receptor-expressing cells/tissues or in a membrane fraction derived from the expressing cells/tissues and even in living bodies (for example, see Nature, Vol. 408, p. 860). It is reported that these homeostatic activities are inhibited by an inverse-agonist. For example, thioperamide or syproxyfan inhibits the homeostatic self-receptor activity of a histamine-H3 receptor, and, as a result, promotes the release of neurotransmitters (e.g., histamine) from nerve ending.

Regarding rats, a high-level selective inhibitor of histamine synthase (histidine decarboxylase) inhibits the vigilance of rats, and therefore histamine participates in controlling motive vigilance. Regarding cats, administration of a histamine-H3 receptor agonist, (R)-(α)-methylhistamine to cats increases their deep slow-wave sleep (for example, see *Brain Research*, Vol. 523, p. 325 (1990)).

Contrary to this, a histamine-H3 receptor antagonist or inverse-agonist, thioperamide dose-dependently increases vigilance, and decreases slow-wave and REM sleep (see *Life Science*, Vol. 48, p. 2397 (1991)). A histamine-H3 receptor antagonist or inverse-agonist, thioperamide or GT-2331 reduces emotional cataplexy and sleep of narcoleptic dogs (for example, see *Brain Research*, Vol. 793, p. 279 (1998)).

These informations suggest that the H3 receptor may participate in control of vigilance-sleep and in sleep disorder-associated diseases, further suggesting a possibility that a selective histamine-H3 agonist, antagonist or inverse-agonist may be useful for treatment of sleep disorders or various sleep disorder-associated diseases (for example, idiopathic hypersomnnia, repetitive hypersomnia, true hypersomnnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, melancholia, anxiety, schizophrenia). Accordingly, it may be considered that the compounds or their salts of above (1) to (14) acting as a histamine-H3 receptor antagonist or inverse-agonist may be effective for prevention and remedy of sleep disorders and various sleep disorder-associated diseases.

In rats, a histamine-H3 receptor antagonist or inverse-agonist, thioperamide or GT-2331 relieves the condition of learning disorder (LD) and attention deficit hyperactivity disorder (ADHD) (for example, see *Life Science*, Vol. 69, p. 469 (2001)). Further in rats, a histamine-H3 receptor agonist, (R)-(α)-methylhistamine lowers their object recognition and learning effects in the object recognition test and the passive turnout test with them.

On the other hand, in a scopolamine-induced amnesia test, a histamine-H3 receptor antagonist or inverse-agonist, thioperamide dose-dependently relieves amnesia induced by the chemical (for example, see *Pharmacology, Biochemistry and Behavior*, Vol. 68, p. 735 (2001)).

These informations suggest a possibility that a histamine-H3 receptor antagonist or inverse-agonist may be useful for prevention or remedy of memory/learning disorder and various diseases accompanied by it (e.g., Alzheimer's disease, Parkinson's disease, attention deficit/hyperactivity disorder). Accordingly, it may also be considered that the compounds or their salts of above (1) to (14) may be effective for prevention or remedy of such memory/learning disorder and various diseases accompanied by it.

Regarding rats, administration of histamine to their ventricle inhibits their eating action, therefore suggesting that histamine may participate in control of eating action (for example, see *Journal of Physiology and Pharmacology*, Vol. 49, p. 191 (1998)). In fact, a histamine-H3 receptor antagonist or inverse-agonist, thioperamide dose-dependently inhibits eating action and promotes intracerebral histamine release (for example, see *Behavioral Brain Research*, Vol. 104, p. 147 (1999)).

These informations suggest that a histamine H3 receptor may participate in eating action control, further suggesting that a histamine-H3 antagonist or inverse-agonist may be useful for prevention or remedy of metabolic syndromes such as eating disorder, obesity, diabetes, emaciation, hyperlipemia. Accordingly, it may be considered that the compounds or their salts of above (1) to (14) may be effective also for prevention or remedy of such metabolic syndromes.

In rats, a histamine-H3 receptor agonist, (R)-(α)-methyl-histamine dose-dependently lowers their basal diastolic pressure, and its action is antagonized by a histamine-H3 receptor antagonist or inverse-agonist, thioperamide (for example, see *European Journal of Pharmacology*, Vol. 234, p. 129, (1993)).

These informations suggest that a histamine-H3 receptor may participate in control of blood pressure, heart beat and cardiac output, further suggesting that a histamine-H3 receptor agonist, antagonist or inverse-agonist may be useful for prevention or remedy of circulatory system diseases such as hypertension and various cardiac disorders. Accordingly, it may be considered that the compounds or their salts of above (1) to (14) may be effective also for prevention or remedy of such circulatory system diseases.

In mice, a histamine-H3 receptor antagonist or inverse-agonist, thioperamide dose-dependently inhibits the spasm induced by electric shock or the epileptoid seizure induced by pentylene tetrazole (PTZ) (for example, see *European Journal of Pharmacology*, Vol. 234, p. 129 (1993) and *Pharmacology, Biochemistry and Behavior*, Vol. 68, p. 735 (2001)).

These informations suggest that a histamine-H3 receptor antagonist or inverse-agonist may be useful for prevention or remedy of epilepsy or central spasm. Accordingly, it may be considered that the compounds or their salts of above (1) to (14) may be effective also for prevention or remedy of such epilepsy or central spasm.

Accordingly, the invention further provides a preventive or remedy for metabolic system diseases, circulatory system diseases or nervous system diseases, which contains, as the active ingredient thereof, the compound or its pharmaceutically-acceptable salt of any one of above (1) to (14).

The metabolic system diseases are at least one selected from obesity, diabetes, hormone secretion disorder, hyperlipemia, gout and fatty liver.

The circulatory system diseases are at least one selected from stenocardia, acute/congestive cardiac insufficiency, cardiac infarction, coronary arteriosclerosis, hypertension, nephropathy and electrolyte metabolism disorder.

The nervous system diseases are at least one selected from sleep disorder, diseases accompanied by sleep disorder, bulimia, emotional disorder, epilepsy, delirium, dementia, attention deficit/hyperactivity disorder, memory disorder, Alzheimer's disease, Parkinson's disease, recognition disorder, motion disorder, paresthesia, dysosmia, morphine resistance, narcotic dependency, alcoholic dependency and tremor.

The nervous system diseases are also at least one selected from idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, melancholia, anxiety, schizophrenia.

The compounds or their pharmaceutically-acceptable salts of above (1) to (14) may be used, as combined with co-medicines. Accordingly, the invention further provides a preventive or remedy for metabolic system diseases, circulator system diseases or nervous system diseases, which contains the compound or its pharmaceutically-acceptable salt of above (1) to (14) and a co-medicine, as the active ingredients thereof. The co-medicine includes a remedy for diabetes, a remedy for hyperlipemia, a remedy for hypertension, a remedy for obesity. Two or more such co-medicines may be used herein, as combined.

The preventive or remedy for metabolic system diseases, circulator system diseases or nervous system diseases, which the invention provides herein, may comprise the following (i), (ii) and (iii):

(i) a compound or its pharmaceutically-acceptable salt of any one of above (1) to (14);

(ii) at least one selected from a group of the following (a) to (g):

(a) a histamine-H3 receptor antagonist or inverse-agonist except (i);

(b) a biguanide, (c) a PPAR (peroxisome proliferator-activated receptor)-agonist;

(d) insulin, (e) somatostatin, (f) an α-glucosidase inhibitor, (g) an insulin secretion promoter;

(iii) a pharmaceutically-acceptable carrier.

BEST MODE FOR CARRYING OUT THE INVENTION

The meanings of the terms used in this description are described first, and then the compounds of the invention are described.

"Aryl group" includes a hydrocarbon-ring aryl group having from 6 to 14 carbon atoms, for example, a phenyl group, a naphthyl group, a biphenyl group, an anthryl group.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Hydroxy-lower alkyl group" means the above-mentioned lower alkyl group substituted with a hydroxy group, including, for example, a hydroxymethyl group, a 2-hydroxyethyl group, a 1-hydroxyethyl group, a 2-hydroxy-1-methyl-ethyl group.

"Lower cycloalkyl group" means a cycloalkyl group having from 3 to 9 carbon atoms, including, for example, a cyclopropyl group, a cyclobutyl group, a cyclopentyl group, a cyclohexyl group, a cycloheptyl group, a cyclooctyl group, a cyclononyl group.

"Lower cycloalkoxy group" means a group of the above-mentioned lower cycloalkyl group with an oxygen atom bonding thereto, including, for example, a cyclopropyloxy group, a cyclobutyloxy group, a cyclopentyloxy group, a cyclohexyloxy group, a cycloheptyloxy group, a cyclooctyloxy group, a cyclononyloxy group.

"Alkoxy group" means a hydroxyl group of which the hydrogen atom is substituted with the above-mentioned lower alkyl group, including, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

"Alkylsulfonyl group" means a group of the above-mentioned alkyl group with a sulfonyl group bonding thereto, including, for example, a methylsulfonyl group, an ethylsulfonyl group, a propylsulfonyl group, an isopropylsulfonyl group, a butylsulfonyl group.

"Alkylsulfonylamino group" means an amino group of which one hydrogen atom is substituted with the above-mentioned alkylsulfonyl group, including, for example, a methylsulfonylamino group, an ethylsulfonylamino group, a propylsulfonylamino group, an isopropylsulfonylamino group, a butylsulfonylamino group, a sec-butylsulfonylamino group, a tert-butylsulfonylamino group, an N-methyl-methylsulfonylamino group, an N-methyl-ethylsulfonylamino group, an N-methyl-propylsulfonylamino group, an N-methyl-isopropylsulfonylamino group, an N-methyl-butylsulfonylamino group, an N-methyl-sec-butylsulfonylamino group, an N-methyl-tert-butylsulfonylamino group, an N-ethyl-methylsulfonylamino group, an N-ethyl-ethylsulfonylamino group, an N-ethyl-propylsulfonylamino group, an N-ethyl-isopropylsulfonylamino group, an N-ethyl-butylsulfonylamino group, an N-ethyl-sec-butylsulfonylamino group, an N-ethyl-tert-butylsulfonylamino group.

"Cyclo-lower alkylsulfonyl group" means a group of the above-mentioned "cycloalkyl group having from 3 to 9 carbon atoms" with a sulfonyl group bonding thereto, including, for example, a cyclopropylsulfonyl group, a cyclobutylsulfonyl group, a cyclopentylsulfonyl group, a cyclohexylsulfonyl group, a cycloheptylsulfonyl group, a cyclooctylsulfonyl group, a cyclononylsulfonyl group.

"Aralkyl group" means the above-mentioned lower alkyl group having the above-mentioned aryl group, including, for example, a benzyl group, a 1-phenylethyl group, a 2-phenylethyl group, a 1-naphthylmethyl group, a 2-naphthylmethyl group.

"Hetero-aryl group" means a 5- to 7-membered monocyclic heteroaryl group having therein from 1 to 3 hetero atoms selected from an oxygen atom, a sulfur atom and a nitrogen atom, or a bicyclic heteroaryl group of the monocyclic heteroaryl group condensed with a benzene ring or a pyridine ring, including, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a quinolyl group, an isoquinolyl group, a quinazolyl group, a quinolidinyl group, an quinoxalinyl group, a cinnolinyl group, a benzimidazolyl group, a imidazopyridyl group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group.

"Halogen atom" means, for example, a fluorine atom, a chlorine atom, a bromine atom, an iodine atom.

"Halo-lower alkyl group" means a lower alkyl group substituted with from 1 to 3 halogen atoms as above, including, for example, a chloromethyl group, a 2-chloroethyl group, a fluoromethyl group, a difluoromethyl group, a trifluoromethyl group.

"Alkoxycarbonylamino group" means an amino group of which one hydrogen atom is substituted with the above-mentioned alkoxycarbonyl group, including, for example, a methoxycarbonylamino group, an ethoxycarbonylamino group, a propoxycarbonylamino group, an isopropoxycarbonylamino group, a butoxycarbonylamino group, a sec-butoxycarbonylamino group, a tert-butoxycarbonylamino group, a pentyloxycarbonylamino group, an N-methyl-methoxycarbonylamino group, an N-methyl-ethoxycarbonylamino group, an N-methyl-propoxycarbonylamino group, an N-methyl-isopropoxycarbonylamino group, an N-methyl-butoxycarbonylamino group, an N-methyl-sec-butoxycarbonylamino group, an N-methyl-tert-butoxycarbonylamino group, an N-ethyl-methoxycarbonylamino group, an N-ethyl-ethoxycarbonylamino group, an N-ethyl-propoxycarbonylamino group, an N-ethyl-isopropoxycarbonylamino group, an N-ethyl-butoxycarbonylamino group, an N-ethyl-sec-butoxycarbonylamino group, an N-ethyl-tert-butoxycarbonylamino group.

"Hydroxyalkyl group" means a group of the above-mentioned lower alkyl group of which one hydrogen atom is substituted with a hydroxyl group, including, for example, a hydroxymethyl group, a hydroxyethyl group, a 1-hydroxypropyl group, a 1-hydroxyethyl group, a 2-hydroxypropyl group, a 2-hydroxy-1-methyl-ethyl group.

"Mono-lower alkylcarbamoyl group" means a carbamoyl group mono-substituted with the above-mentioned lower alkyl group, including, for example, a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group.

"Di-lower alkylcarbamoyl group" means a carbamoyl group di-substituted with the same or different, above-mentioned lower alkyl groups, and the "di-lower alkylcarbamoyl group" includes, for example, a dimethylcarbamoyl group, a diethylcarbamoyl group, an ethylmethylcarbamoyl group, a dipropylcarbamoyl group, a methylpropylcarbamoyl group, a diisopropylcarbamoyl group.

"Di-lower alkylcarbamoyl group" also includes a 5- to 8-membered monocyclic group formed together by the nitrogen atom that constitutes the carbamoyl group and the same or different lower alkyl groups bonding to the nitrogen atom; or a bicyclic group formed through condensation of the monocyclic group with a benzene ring or a pyridine ring. Concretely, they include the following groups:

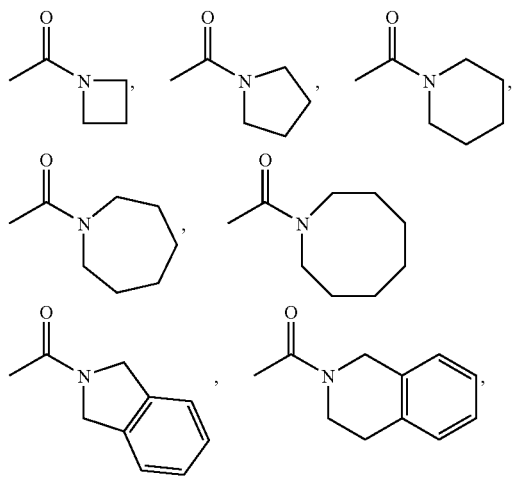

-continued

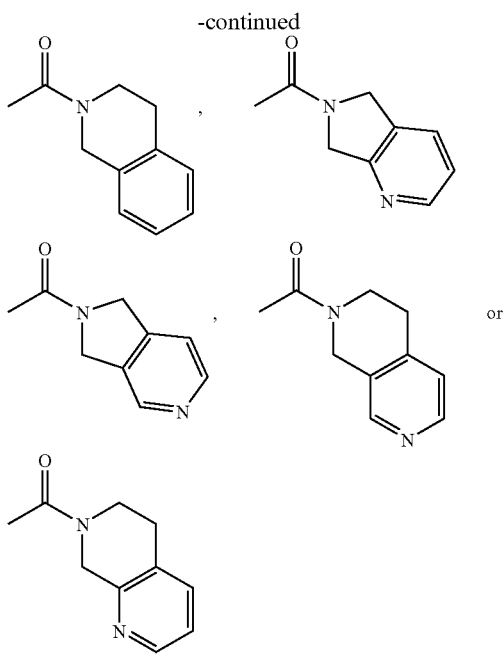

"Alkylamino group" means an amino group mono-substituted with the above-mentioned lower alkyl group, including, for example, a methylamino group, an ethylamino group, a propylamino group, an isopropylamino group, a butylamino group, a sec-butylamino group, a tert-butylamino group.

"Dialkylamino group" means an amino group di-substituted with the same or different, above-mentioned lower alkyl groups, including, for example, a dimethylamino group, a diethylamino group, a dipropylamino group, a methylpropylamino group, a diisopropylamino group.

"Aminoalkyl group" means a group of the above-mentioned alkyl group of which one hydrogen atom is substituted with an amino group, including, for example, an aminomethyl group, an aminoethyl group, an aminopropyl group.

"Alkanoyl group" means a group of the above-mentioned alkyl group with a carbonyl group bonding thereto, including, for example, a methylcarbonyl group, an ethylcarbonyl group, a propylcarbonyl group, an isopropylcarbonyl group.

"Alkanoylamino group" means a group of the above-mentioned alkanoyl group with an amino group bonding thereto, including, for example, an acetylamino group, a propanoylamino group, a butanoylamino group, a pentanoylamino group, an N-methyl-acetylamino group, an N-methyl-propanoylamino group, an N-methyl-butanoylamino group, an N-methyl-pentanoylamino group, an N-ethyl-acetylamino group, an N-ethyl-propanoylamino group, an N-ethyl-butanoylamino group, an N-ethyl-pentanoylamino group.

"Mono-lower alkylaminocarbonyloxy group" means a carbonyloxy group mono-substituted with the above-mentioned lower alkyl group, including, for example, a methylaminocarbonyloxy group, an ethylaminocarbonyloxy group, a propylaminocarbonyloxy group, an isopropylaminocarbonyloxy group.

"Di-lower alkylaminocarbonyloxy group" means a carbonyloxy group di-substituted with the above-mentioned lower alkyl group, including, for example, a dimethylaminocarbonyloxy group, a diethylaminocarbonyloxy group, a diisopropylaminocarbonyloxy group, an ethylmethylaminocarbonyloxy group.

"Alkylthio group" means a group of the above-mentioned alkyl group with a sulfur atom bonding thereto, including, for example, a methylthio group, an ethylthio group, a propylthio group, an isopropylthio group.

"Cycloalkyl group" means a cycloalkyl group having from 3 to 9 carbon atoms, including, for example, a cyclopropyl group, a cyclobutyl group, a cyclopentyl group, a cyclohexyl group, a cycloheptyl group, a cyclooctyl group, a cyclononyl group.

"Cycloalkoxy group" means a group of the above-mentioned alkoxy group in which the alkyl group is substituted with a cycloalkyl group having from 3 to 9 carbon atoms, including, for example, a cyclopropoxy group, a cyclobutoxy group, a cyclopentyloxy group, a cyclohexyloxy group, a cycloheptyloxy group.

"Aryloxy group" means a group of the above-mentioned aryl group with an oxygen atom bonding thereto, including, for example, a phenoxy group, a naphthalene-1-yloxy group, a naphthalene-2-yloxy group.

"Heteroaryloxy group" means a group of the above-defined "heteroaryl group" with an oxy group bonding thereto, including, for example, a furan-2-yloxy group, a furan-3-yloxy group, a thiophen-2-yloxy group, a thiophen-3-yloxy group, a 1H-pyrrol-2-yloxy group, a 1H-pyrrol-3-yloxy group, a 1H-imidazol-2-yloxy group, a 1H-imidazol-4-yloxy group, a 3H-imidazol-4-yloxy group, a 4H-[1,3,4]triazol-3-yloxy group, a 2H-[1,2,4]triazol-3-yloxy group, a 1H-[1,2,4]triazol-3-yloxy group, a thiazol-2-yloxy group, a thiazol-4-yloxy group, a thiazol-5-yloxy group, a pyridin-2-yloxy group, a pyridin-3-yloxy group, a pyridin-4-yloxy group, a pyrimidin-2-yloxy group, a pyrimidin-4-yloxy group, a pyrimidin-5-yloxy group, a pyridazin-3-yloxy group, a pyridazin-4-yloxy group, a 2H-pyrazol-3-yloxy group, a 1H-pyrazol-4-yloxy group, a 1H-pyrazol-3-yloxy group, a pyrazin-3-yloxy group, a pyrazin-4-yloxy group, a quinolin-2-yloxy group, a quinolin-3-yloxy group, a quinolin-4-yloxy group, an isoquinolin-1-yloxy group, an isoquinolin-3-yloxy group, an isoquinolin-4-yloxy group, a quinazolin-2-yloxy group, a quinazolin-3-yloxy group, a quinoxalin-2-yloxy group, a quinoxalin-3-yloxy group, a cinnolin-3-yloxy group, a cinnolin-4-yloxy group, a 1H-benzimidazol-2-yloxy group, a 1H-imidazo[4,5-b]pyridin-5-yloxy group, a 1H-imidazo[4,5-b]pyridin-6-yloxy group, 1H-imidazo[4,5-b]pyridine-7-yloxy group, a benzo[d]isoxazol-4-yloxy group, a benzo[d]isoxazol-5-yloxy group, a benzo[d]isoxazol-6-yloxy group, a benzoxazol-4-yloxy group, a benzoxazol-5-yloxy group, a benzoxazol-6-yloxy group.

"Heteroarylalkyl group" means a group formed by the above-mentioned heteroaryl group and the above-mentioned alkyl group bonding to each other, including, example, a furan-3-ylmethyl group, a furan-2-ylmethyl group, a furan-3-ylmethyl group, a furan-2-ylmethyl group, a furan-3-ylpropyl group, a furan-2-ylpropyl group, a thiophen-3-ylmethyl group, a thiophen-2-ylmethyl group, a thiophen-3-ylethyl group, a thiophen-2-ylethyl group, a thiophen-3-ylpropyl group, a thiophen-2-ylpropyl group, a 1H-pyrrol-3-ylmethyl group, a 1H-pyrrol-2-ylmethyl group, a 1H-pyrrol-3-ylethyl group, a 1H-pyrrol-2-ylethyl group, a 1H-pyrrol-3-ylpropyl group, a 1H-pyrrol-2-ylpropyl group, a 1H-imidazol-4-ylmethyl group, a 1H-imidazol-2-ylmethyl group, a 1H-imidazol-5-ylmethyl group, a 1H-imidazol-4-ylethyl group, a 1H-imidazol-2-ylethyl group, a 1H-imidazol-5-ylethyl group, a 1H-imidazol-4-ylpropyl group, a 1H-imidazol-2-ylpropyl group, a 1H-imidazol-5-ylpropyl group, a 1H-[1,2,3]triazol-4-ylmethyl group, a 1H-[1,2,3]triazol-5-ylmethyl group, a 1H-[1,2,3]triazol-4-ylethyl group, a 1H-[1,2,3]triazol-5-ylethyl group, a 1H-[1,2,3]triazol-4-ylpropyl group, a 1H-[1,2,3]triazol-5-ylpropyl group, a 1H-[1,2,4]triazol-3-ylmethyl group, a 1H-[1,2,4]triazol-5-ylmethyl group, a 1H-[1,2,4]triazol-3-ylethyl group, a 1H-[1,2,4]triazol-5-ylethyl group, a 1H-[1,2,4]triazol-3-ylpropyl group, a 1H-[1,2,4]triazol-5-ylpropyl group, a thiazol-4-ylmethyl group, a thiazol-3-ylmethyl group, a thiazol-2-ylmethyl group, a thiazol-4-ylethyl group, a thiazol-3-ylethyl group, a thiazol-2-ylethyl group, a thiazol-4-ylpropyl group, a thiazol-3-ylpropyl group, a thiazol-2-ylpropyl group, a [1,2,4]thiadiazol-3-ylmethyl group, a [1.2.4]thiadiazol-3-ylethyl group, a [1,2,4]thiadiazol-3-ylpropyl group, a [1,2,4]thiadiazol-5-ylmethyl group, a [1,2,4]thiadiazol-5-ylethyl group, a [1,2,4]thiadiazol-5-ylpropyl group, a [1,3,4]thiadiazol-2-ylmethyl group, a [1,3,4]thiadiazol-2-ylethyl group, a [1,3,4]thiadiazol-2-ylpropyl group.

"Monoarylcarbamoyl group" means a carbamoyl group mono-substituted with the above-mentioned aryl group, including, for example, a phenylcarbamoyl group.

For further more concretely disclosing the compounds of formula (I) of the invention, the symbols used in the formula (I):

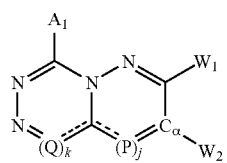

(I)

[in the formula, the symbols have the same meanings as above] are described below.

$A_1$ represents a hydrogen atom, a group selected from a substituent group β optionally having 1 or 2 groups selected from a substituent group α, or a phenyl or heteroaryl group optionally having 1 or 2 groups selected from a substituent group γ.

The substituent group a includes those mentioned hereinabove, of which, for example, preferred are a cyano group, a halogen atom, a lower alkyl group, a lower alkoxy group, a lower cycloalkoxy group.

The substituent group β includes those mentioned hereinabove, of which, for example, preferred are a lower alkyl group, a lower cycloalkyl group, a lower alkoxy group, a lower cycloalkyl group.

For the "group selected from a substituent group β optionally having 1 or 2 groups selected from a substituent group α" for $A_1$, for example, preferred are a methyl group, an ethyl group, a trifluoromethyl group, a tert-butyl group.

The substituent group γ includes those mentioned hereinabove, of which, for example, preferred are a cyano group, a halogen atom, a lower alkyl group, a lower cycloalkyl group, a lower alkoxy group, a lower cycloalkoxy group, a mono-lower alkylcarbamoyl group, a di-lower alkylcarbamoyl group, a lower alkylcarboxamido group, an arylcarboxamido group, a heteroarylcarboxamido group.

The "heteroaryl group" for $A_1$ indicates the following (1) or (2):
(1) a 5-membered or 6-membered monocyclic aromatic heterocyclic group having the same or different, one or more, preferably 1 to 3 hetero atoms selected from a group consisting of a nitrogen atom, an oxygen atom and a sulfur atom;
(2) a condensed-cyclic aromatic heterocyclic group formed through condensation of the monocyclic aromatic heterocyclic group of above (1) and the above-mentioned aryl group; or a condensed-cyclic aromatic heterocyclic group formed through condensation of the same or different, above-mentioned monocyclic aromatic heterocyclic groups.

Concretely, (1) "an 5-membered or 6-membered monocyclic aromatic heterocyclic group having the same or different, one or more hetero atoms selected from a group consisting of a nitrogen atom, an oxygen atom and a sulfur atom" for $A_1$ includes, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a tetrazolyl group, an oxadiazolyl group. Of those, preferred are . . . ; and more preferred are a phenyl group, an isoxazolyl group, a pyridyl group, a pyrimidinyl group.

Stating (2) "a condensed-cyclic aromatic heterocyclic group formed through condensation of the monocyclic aromatic heterocyclic group and the above-mentioned aryl group, or a condensed-cyclic aromatic heterocyclic group formed through condensation of the same or different, above-mentioned monocyclic aromatic heterocyclic groups" for it, $A_1$ means a condensed group of the 5-membered or 6-membered monocyclic aromatic heterocyclic group of (1) and the above-defined hydrocarbon-ring aryl group having from 6 to 14 carbon atoms; or means a condensed-cyclic aromatic heterocyclic group formed through condensation of the same or different, monocyclic aromatic heterocyclic groups of above (1). More concretely, for example, it includes a quinolyl group, an isoquinolyl group, a quinazolyl group, a quinolidinyl group, a quinoxalyl group, a cinnolinyl group, a benzimidazolyl group, an imidazopyridiyl group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group, an indolyl group, a benzothienyl group, a benzisothiazolyl group, indazolyl group, a purinyl group, a phthalazinyl group, a naphthyridinyl group, a pteridinyl group.

$A_1$ is, for example, a hydrogen atom, a methyl group, a trifluoromethyl group, an ethyl group, a pyridyl group, a phenyl group, a mono-lower alkylcarbamoyl group, a di-lower alkylcarbamoyl group, or a piperidin-1-yl-carbonyl group.

j and k each independently indicate 0 or 1. Preferably, j is 0 and k is 1; or j is 1 and k is 0.

$A_2$ has the same meaning as $A_1$, and is preferably a hydrogen atom or a lower alkyl group, more preferably a hydrogen atom.

$A_3$ has the same meaning as $A_1$, and is preferably a hydrogen atom or a lower alkyl group.

$A_4$ has the same meaning as $A_1$, and is preferably a hydrogen atom or a lower alkyl group, more preferably a hydrogen atom.

E is a phenyl group optionally having from 1 to 3 groups selected from a substituent group δ, or a 5- or 6-membered monocyclic aromatic heterocyclic group having 1 or more, preferably from 1 to 3, the same or different hetero atoms selected from a group consisting of a nitrogen atom, an oxygen atom and a sulfur atom, or represents a condensed-cyclic aromatic heterocyclic group formed through condensation of the monocyclic aromatic heterocyclic group and an aryl group.

Concretely, for example, E (this E may have from 1 to 3 groups selected from the substituent group δ) includes a phenyl group, a pyrimidinyl group, a pyridyl group and a pyridazyl group, or that is, it is a divalent group derived from a benzene, pyrimidine, pyridine or pyridazine by removing two hydrogen atoms therefrom. Of those, preferred are a phenyl group and a pyrimidinyl group, or that is, divalent groups derived from benzene and pyridine by removing two hydrogen atoms therefrom; and more preferred is a phenyl group, or that is, a divalent group derived from a benzene by removing two hydrogen atoms therefrom.

Of the substituent group δ, for example, preferred are a halogen atom, a lower alkoxy group, a hydroxy-lower alkyl group. The halogen atom includes a fluorine atom, a bromine atom, a chlorine atom. The lower alkoxy group includes a methoxy group, an ethoxy group. The lower alkoxy group may be further substituted with a halogen atom. The lower alkyl group includes a methyl group, an ethyl group.

W is a group of a formula (II-1):

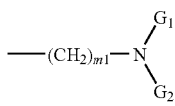

[in the formula, the symbols have the same meanings as above], a group of a formula (II-2):

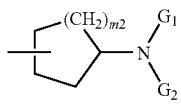

[in the formula, the symbols have the same meanings as above], or a group of a formula (II-3):

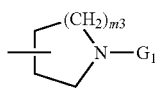

[in the formula, the symbols have the same meanings as above].

The compounds where W is a group of a formula (II-1):

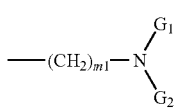

[in the formula, the symbols have the same meanings as above] are described.

m1 is an integer of from 2 to 4, preferably 3 or 4, more preferably 3.

The "lower alkyl group" for $G_1$ and $G_2$ may be the same as the above-mentioned lower alkyl group, including, for example, a methyl group, an ethyl group, a propyl group, an isopropyl group.

The lower alkyl groups may be the same or different.

The lower alkyl group may be further substituted with a halogen atom.

The "cycloalkyl group" for $G_1$ and $G_2$ may be the same as the above-mentioned cycloalkyl group, including a cyclopropyl group, a cyclobutyl group.

In formula (II-1), $G_1$, $G_2$ and the nitrogen atom may together form a 5- to 8-membered aliphatic hetero-ring (the hetero-ring may have, in the ring, 1 or 2 groups of a lower alkyl group optionally substituted with a halogen atom or a halogen atom) or a bicyclo-ring.

The 5- to 8-membered aliphatic hetero ring includes a pyrrolidine ring, a piperidine ring, a homopiperidine ring, a heptamethylenimine ring, a piperazine ring, a morpholine ring, a homomorpholine ring.

The bicyclo-ring that $G_1$, $G_2$ and the nitrogen atom together form in formula (II-1) may be an aza-bicyclic ring, and this is a non-aromatic ring in which only one hetero atom that constitutes the ring is the nitrogen atom adjacent to $G_1$ and $G_2$ in formula (II-1). The bicyclo-ring preferably has from 6 to 10 ring-constituting atoms, more preferably from 7 to 9 ring-constituting atoms.

The bicyclo-ring includes, for example, groups of a formula (III-1):

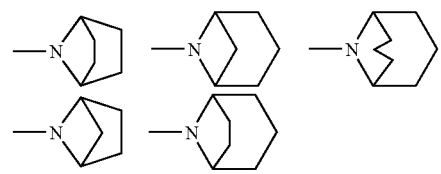

$CH_2$ in formula (II-1) may be substituted with a lower alkyl group having from 1 to 3 carbon atoms. The lower alkyl group includes a methyl group, an ethyl group, an n-propyl group, an isopropyl group.

When W is a group of formula (II-1), it is desirable that m1 is 3 or 4 and that $G_1$, $G_2$ and the nitrogen atom together form a 5- to 8-membered aliphatic hetero ring (the hetero ring may have, in the ring, 1 or 2 groups of a lower alkyl group optionally substituted with a halogen atom or a halogen atom) or a 6- or 10-membered bi-cyclo ring; more preferably m1 is 3, and $G_1$, $G_2$ and the nitrogen atom together form a 5- to 8-membered aliphatic hetero ring (the hetero ring may have, in the ring, 1 or 2 groups of a lower alkyl group optionally substituted with a halogen atom or a halogen atom) or a bi-cyclo ring.

The compounds where W is a group of a formula (II-2):

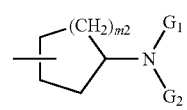

[in the formula, the symbols have the same meanings as above] are described.

m2 is an integer of from 1 to 3, preferably 2 or 3.

$G_1$ and $G_2$ have the same meanings as above, and their preferred embodiments and more preferred embodiments may be the same as above.

When W is a group of formula (II-2), then two different carbon atoms of those constituting W (but excepting the carbon atoms in $G_1$ and $G_2$) may bond to each other via a single bond or —(CH$_2$)$_{m11}$— (where m11 indicates an integer of from 1 to 3), thereby forming a bicyclo ring. The bicyclo ring includes, for example, groups of a formula (III-2):

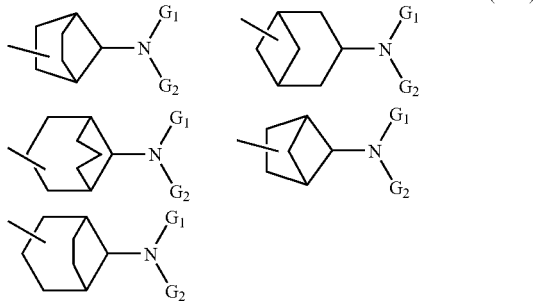

[In these formulae, the symbols have the same meanings as above.]

Preferred embodiments of G$_1$ and G$_2$ in the embodiment where W is a bicyclo ring of formula (III-2) may be the same as those mentioned hereinabove.

The compounds where W is a group of a formula (II-3):

[in the formula, the symbols have the same meanings as above] are described.

m3 is an integer of from 1 to 3, preferably 2 or 3.

G$_1$ has the same meanings as above, and its preferred embodiments and more preferred embodiments may be the same as above.

When W is a group of formula (II-3), then two different carbon atoms of those constituting W may bond to each other via —(CH$_2$)$_{m11}$— (where m11 indicates an integer of from 1 to 3), thereby forming a bicyclo ring. The bicyclo ring includes, for example, groups of a formula (III-3):

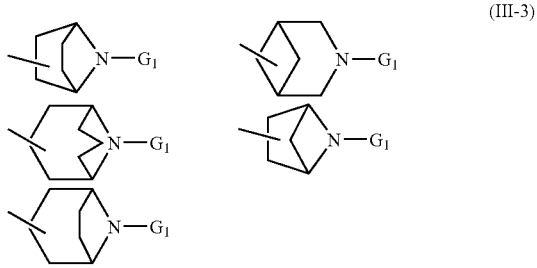

In formula (III-3), preferred embodiments and more preferred embodiments of G$_1$ may be the same as those mentioned hereinabove.

From the above, W includes, for example, a 2-dimethylamino-ethyl group, a 2-diethylamino-ethyl group, a 2-di-n-propylamino-ethyl group, a 2-diisopropylamino-ethyl group, a 3-dimethylamino-propyl group, a 3-diethylamino-propyl group, a 3-di-n-propylamino-propyl group, a 3-diisopropylamino-propyl group, a 4-dimethylamino-butyl group, a 4-di-ethylamino-butyl group, a 4-di-n-propylamino-butyl group, a 4-diisopropylamino-butyl group, a 2-(methylmethylamino)ethyl group, a 2-(ethylpropylamino)ethyl group, a 2-(ethylisopropylamino)ethyl group, a 2-(ethylisopropylamino)ethyl group, a 2-(ethyl-n-propyl-amino)ethyl group, a 3-(ethylmethylamino)propyl group, a 3-(ethylpropylamino)propyl group, a 3-(ethylisopropylamino)propyl group, a 3-(methylisopropylamino)propyl group, a 2-(ethyl-n-propyl-amino) propyl group, a 4-(ethylmethylamino)butyl group, a 4-(ethylpropylamino)butyl group, a 4-(ethylisopropylamino)butyl group, a 2-(ethyl-n-propyl-amino)butyl group, a 2-dicyclopropylamino-ethyl group, a 2-dicyclobutylamino-ethyl group, a 2-dicyclopentylamino-ethyl group, a 2-dicyclohexylamino-ethyl group, a 3-dicyclopropylamino-propyl group, a 3-dicyclobutylamino-propyl group, a 3-dicyclopentylamino-propyl group, a 3-dicyclohexylamino-propyl group, a 4-dicyclopropylamino-butyl group, a 4-dicyclobutylamino-butyl group, a 4-dicyclopentylamino-butyl group, a 4-dicyclohexylamino-butyl group, a 2-(cyclobutyl-cyclopropylamino)ethyl group, a 2-(cyclobutyl-cyclopentyl-amino)ethyl group, a 2-(cyclohexyl-cyclopentyl)ethyl group, a 3-(cyclobutyl-cyclopropyl-amino)propyl group, a 3-(cyclobutyl-cyclopentyl-amino)propyl group, a 3-(cyclohexyl-cyclopentyl-amino) propyl group, a 4-(cyclobutyl-cyclopropyl-amino)butyl group, a 4-(cyclobutyl-cyclopentyl-amino)butyl group, a 4-(cyclohexyl-cyclopentyl-amino)butyl group, a 2-(cyclopropyl-methyl-amino)ethyl group, a 2-(cyclopropyl-ethyl-amino)ethyl group, a 2-(cyclopropyl-n-propyl-amino)ethyl group, a 2-(cyclopropyl-isopropyl-amino)ethyl group, a 2-(cyclobutyl-methyl-amino)ethyl group, a 2-(cyclobutyl-ethyl-amino)ethyl group, a 2-(cyclobutyl-n-propyl-amino) ethyl group, a 2-(cyclobutyl-isopropyl-amino)ethyl group, a 2-(cyclopentyl-methyl-amino)ethyl group, a 2-(cyclopentyl-ethyl-amino)ethyl group, a 2-(cyclopentyl-n-propyl-amino) ethyl group, a 2-(cyclopentyl-isopropyl-amino)ethyl group, a 2-(cyclohexyl-methyl-amino)ethyl group, a 2-(cyclohexyl-ethyl-amino)ethyl group, a 2-(cyclohexyl-n-propyl-amino) ethyl group, a 2-(cyclohexyl-isopropyl-amino)ethyl group, a 3-(cyclopropyl-methyl-amino)propyl group, a 3-(cyclopropyl-ethyl-amino)propyl group, a 3-(cyclopropyl-n-propyl-amino)propyl group, a 3-(cyclopropyl-isopropyl-amino)propyl group, a 3-(cyclobutyl-methyl-amino)propyl group, a 3-(cyclobutyl-ethyl-amino)propyl group, a 3-(cyclobutyl-n-propyl-amino)propyl group, a 3-(cyclobutyl-isopropyl-amino)propyl group, a 3-(cyclopentyl-methyl-amino)propyl group, a 3-(cyclopentyl-ethyl-amino)propyl group, a 3-(cyclopentyl-n-propyl-amino)propyl group, a 3-(cyclopentyl-isopropyl-amino)propyl group, a 3-(cyclohexyl-methyl-amino)propyl group, a 3-(cyclohexyl-ethyl-amino)propyl group, a 3-(cyclohexyl-n-propyl-amino)propyl group, a 3-(cyclohexyl-isopropyl-amino)propyl group, a 4-(cyclopropyl-methyl-amino)butyl group, a 4-(cyclopropyl-ethyl-amino)butyl group, a 4-(cyclopropyl-n-propyl-amino)butyl group, a 4-(cyclopropyl-isopropyl-amino)butyl group, a 4-(cyclobutyl-methyl-amino)butyl group, a 4-(cyclobutyl-ethyl-amino)butyl group, a 4-(cyclobutyl-n-propyl-amino) butyl group, a 4-(cyclobutyl-isopropyl-amino)butyl group, a 4-(cyclopentyl-methyl-amino)butyl group, a 4-(cyclopentyl-ethyl-amino)butyl group, a 4-(cyclopentyl-n-propyl-amino) butyl group, a 4-(cyclopentyl-isopropyl-amino)butyl group, a 4-(cyclohexyl-methyl-amino)butyl group, a 4-(cyclohexyl-ethyl-amino)butyl group, a 4-(cyclohexyl-n-propyl-amino) butyl group, a 4-(cyclohexyl-isopropyl-amino)butyl group, a 2-pyrrolidin-1-ylethyl group, a 2-piperidin-1-ylethyl group, a 2-homopiperidin-1-ylethyl group, a 2-heptamethylenimin-1-ylethyl group, a 2-morpholin-4-ylethyl group, a 2-homomorpholin-4-ylethyl group, a 3-pyrrolidin-1-ylpropyl group, a 3-piperidin-1-ylpropyl group, a 3-homopiperidin-1-ylpropyl group, a 3-heptamethylenimin-1-ylpropyl group, a 3-morpholin-4-ylpropyl group, a 3-homomorpholin-4-ylpropyl group, a 4-pyrrolidin-1-ylbutyl group, a 4-piperidin-1-ylbutyl group, a 4-homopiperidin-1-ylbutyl group, a 4-heptamethylenimin-1-ylbutyl group, a 4-morpholin-4-ylbutyl group, a 4-homomorpholin-4-ylbutyl group, a 2-(5-aza-bicyclo[2.1.1]hexan-5-ylethyl group, a 2-(6-aza-bicyclo[3.1.1]heptan-6-ylethyl group, a 2-(7-aza-bicyclo[2.1.1]heptan-7-ylethyl group, a 2-(8-aza-bicyclo[3.2.1]octan-8-ylethyl group, a 2-(9-aza-bicyclo[3.3.1]nonan-9-ylethyl group, a 3-(5-aza-bicyclo[2.1.1]hexan-5-ylpropyl group, a 3-(6-aza-bicyclo[3.1.1]heptan-6-ylpropyl group, a 3-(7-aza-bicyclo[2.1.1]heptan-7-ylpropyl group, a 3-(8-aza-bicyclo[3.2.1]octan-8-ylpropyl group, a 3-(9-aza-bicyclo[3.3.1]nonan-9-ylpropyl group, a 4-(5-aza-bicyclo[2.1.1]hexan-5-ylbutyl group, a 4-(6-aza-bicyclo[3.1.1]heptan-6-ylbutyl group, a 4-(7-aza-bicyclo[2.1.1]heptan-7-ylbutyl group, a 4-(8-aza-bicyclo[3.2.1]octan-8-ylbutyl group, a 4-(9-aza-bicyclo[3.3.1]nonan-9-ylbutyl group, a 1-methylazetidin-3-yl group, a 1-methylazetidin-2-yl group, a 1-ethylazetidin-3-yl group, a 1-ethylazetidin-2-yl group, a 1-isopropylazetidin-3-yl group, a 1-isopropylazetidin-2-yl group, a 1-cyclopropylazetidin-3-yl group, a 1-cyclobutylazetidin-3-yl group, a 1-cyclobutylazetidin-2-yl group, a 1-cyclopentylazetidin-3-yl group, a 1-cyclopentylazetidin-2-yl group, a 1-cyclohexylazetidin-3-yl group, a 1-cyclohexylazetidin-2-yl group, a 1-methylpyrrolidin-3-yl group, a 1-methylpyrrolidin-2-yl group, a 1-ethylpyrrolidin-3-yl group, a 1-ethylpyrrolidin-3-yl group, a 1-isopropylpyrrolidin-3-yl group, a 1-isopropyl-pyrrolidin-2-yl group, a 1-cyclopropylpyrrolidin-3-yl group, a 1-cyclopropylpyrrolidin-2-yl group, a 1-cyclobutylpyrrolidin-3-yl group, a 1-cyclobutylpyrrolidin-2-yl group, a 1-cyclopentylpyrrolidin-3-yl group, a 1-cyclopentylpyrrolidin-2-yl group, a 1-cyclohexylpyrrolidin-3-yl group, a 1-cyclohexylpyrrolidin-2-yl group, a 1-methylpiperidin-4-yl group, a 1-methylpiperidin-3-yl group, a 1-methylpiperidin-2-yl group, a 1-ethylpiperidin-4-yl group, a 1-ethylpiperidin-3-yl group, a 1-ethylpiperidin-2-yl group, a 1-isopropylpiperidin-4-yl group, a 1-isopropylpiperidin-3-yl group, a 1-isopropylpiperidin-2-yl group, a 1-cyclopropylpiperidin-4-yl group, a 1-cyclopropylpiperidin-3-yl group, a 1-cyclopropylpiperidin-2-yl group, a 1-cyclobutylpiperidin-4-yl group, a 1-cyclobutylpiperidin-3-yl group, a 1-cyclobutylpiperidin-2-yl group, a 1-cyclopentylpiperidin-4-yl group, a 1-cyclopentylpiperidin-3-yl group, a 1-cyclopentylpiperidin-2-yl group, a 1-cyclohexylpiperidin-4-yl group, a 1-cyclohexylpiperidin-3-yl group, a 1-cyclohexylpiperidin-2-yl group, a 3-dimethylaminocyclobutyl group, a 3-diethylaminocyclobutyl group, a 3-diisopropylaminocyclobutyl group, a 3-dicyclopropylaminobutyl group, a 3-dicyclobutylaminobutyl group, a 3-dicyclopentylaminobutyl group, a 3-dicyclohexylaminobutyl group, a 2-dimethylaminocyclobutyl group, a 2-diethylaminocyclobutyl group, a 2-diisopropylaminocyclobutyl group, a 2-dicyclopropylaminobutyl group, a 2-dicyclobutylaminobutyl group, a 2-dicyclopentylaminobutyl group, a 2-dicyclohexylaminobutyl group, a 3-(cyclopropyl-methylamino)cyclobutyl group, a 3-(cyclopropyl-ethylamino)cyclobutyl group, a 3-(cyclobutyl-methyl-amino)cyclobutyl group, a 3-(cyclobutyl-ethyl-amino)cyclobutyl group, a 3-(cyclopentyl-methyl-amino)cyclobutyl group, a 3-(cyclopentyl-ethyl-amino)cyclobutyl group, a 3-(cyclohexyl-methyl-amino)cyclobutyl group, a 2-(cyclopropyl-methyl-amino)cyclobutyl group, a 2-(cyclopropyl-ethyl-amino)cyclobutyl group, a 2-(cyclobutyl-methyl-amino)cyclobutyl group, a 2-(cyclobutyl-ethyl-amino)cyclobutyl group, a 2-(cyclopentyl-methyl-amino)cyclobutyl group, a 2-(cyclopentyl-ethyl-amino)cyclobutyl group, a 2-(cyclohexyl-methyl-amino)cyclobutyl group, a 3-pyrrolidin-1-yl-cyclobutyl group, a 2-pyrrolidin-1-yl-cyclobutyl group, a 3-pyrrolidin-1-yl-cyclopentyl group, a 2-pyrrolidin-1-yl-cyclopentyl group, a 4-pyrrolidin-1-yl-cyclohexyl group, a 3-pyrrolidin-1-yl-cyclohexyl group, a 2-pyrrolidin-1-yl-cyclohexyl group, a 3-piperidin-1-yl-cyclobutyl group, a 2-piperidin-1-yl-cyclobutyl group, a 3-piperidin-1-yl-cyclopentyl group, a 2-piperidin-1-yl-cyclopentyl group, a 4-piperidin-1-yl-cyclohexyl group, a 3-piperidin-1-yl-cyclohexyl group, a 2-piperidin-1-yl-cyclohexyl group, a 3-homopiperidin-1-yl-cyclobutyl group, a 2-homopiperidin-1-yl-cyclobutyl group, a 3-homopiperidin-1-yl-cyclopentyl group, a 2-homopiperidin-1-yl-cyclopentyl group, a 4-homopiperidin-1-yl-cyclohexyl group, a 3-homopiperidin-1-yl-cyclohexyl group, a 2-homopiperidin-1-yl-cyclohexyl group, a 3-heptamethylenimin-1-yl-cyclobutyl group, a 2-heptamethylenimin-1-yl-cyclobutyl group, a 3-heptamethylenimin-1-yl-cyclopentyl group, a 2-heptamethylenimin-1-yl-cyclopentyl group, a 4-heptamethylenimin-1-yl-cyclohexyl group, a 3-heptamethylenimin-1-yl-cyclohexyl group, a 2-heptamethylenimin-1-yl-cyclohexyl group, a 2-morpholin-4-yl-cyclobutyl group, a 3-morpholin-4-yl-cyclobutyl group, a 2-morpholin-4-yl-cyclopentyl group, a 3-morpholin-4-yl-cyclopentyl group, a 2-morpholin-4-yl-cyclohexyl group, a 3-morpholin-4-yl-cyclohexyl group, a 4-morpholin-4-yl-cyclohexyl group, a 2-homomorpholin-4-yl-cyclobutyl group, a 3-homomorpholin-4-yl-cyclobutyl group, a 4-homomorpholin-4-yl-cyclobutyl group, a 2-homomorpholin-4-yl-cyclopentyl group, a 3-homomorpholin-4-yl-cyclopentyl group, a 4-homomorpholin-4-yl-cyclopentyl group, a 2-homomorpholin-4-yl-cyclohexyl group, a 3-homomorpholin-4-yl-cyclohexyl group, a 4-homomorpholin-4-yl-cyclohexyl group, a 2-(5-aza-bicyclo[2.1.1]hexan-5-yl)cyclobutyl group, a 2-(6-aza-bicyclo[3.1.1]heptan-6-yl)cyclobutyl group, a 2-(7-aza-bicyclo[2.1.1]heptan-7-yl)cyclobutyl group, a 2-(8-aza-bicyclo[3.2.1]octan-8-yl)cyclobutyl group, a 2-(9-aza-bicyclo[3.3.1]nonan-9-yl)cyclobutyl group, a 3-(5-aza-bicyclo[2.1.1]hexan-5-yl)cyclobutyl group, a 3-(6-aza-bicyclo[3.1.1]heptan-6-yl)cyclobutyl group, a 3-(7-aza-bicyclo[2.1.1]heptan-7-yl)cyclobutyl group, a 3-(8-aza-bicyclo[3.2.1]octan-8-yl)cyclobutyl group, a 3-(9-aza-bicyclo[3.3.1]nonan-9-yl)cyclobutyl group, a 2-(5-aza-bicyclo[2.1.1]hexan-5-yl)cyclopentyl group, a 2-(6-aza-bicyclo[3.1.1]heptan-6-yl)cyclopentyl group, a 2-(7-aza-bicyclo[2.1.1]heptan-7-yl)cyclopentyl group, a 2-(8-aza-bicyclo[3.2.1]octan-8-yl)cyclopentyl group, a 2-(9-aza-bicyclo[3.3.1]nonan-9-yl)cyclopentyl group, a 3-(5-aza-bicyclo[2.1.1]hexan-5-yl)cyclopentyl group, a 3-(6-aza-bicyclo[3.1.1]heptan-6-yl)cyclopentyl group, a 3-(7-aza-bicyclo[2.1.1]heptan-7-yl)cyclopentyl group, a 3-(8-aza-bicyclo[3.2.1]octan-8-yl)cyclopentyl group, a 3-(9-aza-bicyclo[3.3.1]nonan-9-yl)cyclopentyl group, a 2-(5-aza-bicyclo[2.1.1]hexan-5-yl)cyclohexyl group, a 2-(6-aza-bicyclo[3.1.1]heptan-6-yl)cyclohexyl group, a 2-(7-aza-bicyclo[2.1.1]heptan-7-yl)cyclohexyl group, a 2-(8-aza-bicyclo[3.2.1]octan-8-yl)cyclohexyl group, a 2-(9-aza-bicyclo[3.3.1]nonan-9-yl)cyclohexyl group, a 3-(5-aza-bicyclo[2.1.1]hexan-5-yl)cyclohexyl group, a 3-(6-aza-bicyclo[3.1.1]heptan-6-yl)cyclohexyl group, a 3-(7-aza-bicyclo[2.1.1]heptan-7-yl)cyclohexyl group, a 3-(8-aza-bicyclo[3.2.1]octan-8-yl)cyclohexyl group, a 3-(9-aza-bicyclo[3.3.1]nonan-9-yl)cyclohexyl group, a 3-(7-azabicyclo[2.2.1]hept-7-yl)propyl group, a 3-(8-azabicyclo[3.2.1]oct-8-yl)propyl group, a 3-(3,3-difluoropyrrolidin-1-yl)propyl group, a 3-(3-fluoropiperidin-1-yl)propyl group, a 3-[(3R)-3-fluoropyrrolidin-1-yl]propyl group, a 3-(4,4-difluoropiperidin-1-yl)propyl group, a 3-(4-fluoropiperidin-1-yl)propyl group, a 3-(3,3-difluoropiperidin-1-yl)propyl group, a 3-[(3R)-3-methylpiperidin-1-yl]propyl group, a 3-[(2R,5R)-2,5-dimethylpyrrolidin-1-yl]propyl group, a 3-[3-methylpyrrolidin-1-ylpropyl group, a 3-[(2S)-2-methylpyrrolidin-1-yl] propyl group, a 3-[(2R)-2-methylpyrrolidin-1-yl]propyl group, a 3-[(3S)-3-methylpiperidin-1-yl]propyl group, a 3-(azepan-1-yl)propyl group, a 3-[(2-oxopyrrolidin-1-yl)] propyl group. Of those, preferred are a 3-piperidin-1-ylpropyl group, a 1-cyclobutylpiperidin-4-yl group, a 1-cyclopentylpiperidin-4-yl group, a 3-[(3S)-3-methylpiperidin-1-yl]propyl group, a 3-[(2R)-2-methylpyrrolidin-1-yl]propyl group, a 3-[(2S)-2-methylpyrrolidin-1-yl]propyl group, a 1-cyclopentylpiperidin-4-yl group, a 3-(pyrrolidin-1-yl)propyl group, a 3-(piperidin-1-yl)propyl group.

The compounds of formula (I) include, for example, compounds of a formula (I-0):

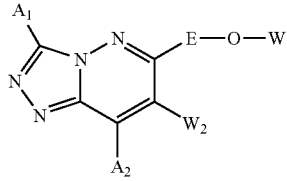

(I-0)

[in the formula, the symbols have the same meanings as above];

compounds of a formula (I-1):

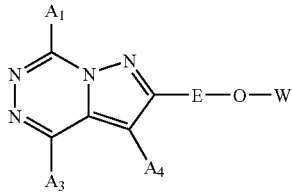

(I-1)

[in the formula, the symbols have the same meanings as above];

compounds of a formula (I-2):

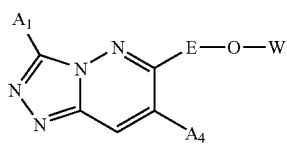

(I-2)

[in the formula, the symbols have the same meanings as above];

compounds of a formula (I-3):

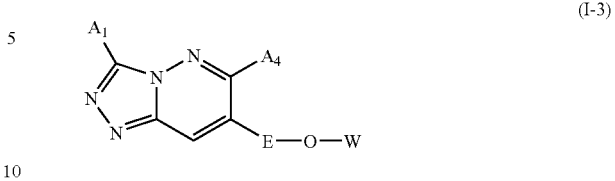

(I-3)

[in the formula, the symbols have the same meanings as above].

Of those, preferred are compounds of formula (I-0).

The compounds of formula (I-0) include compounds of a formula (I-4):

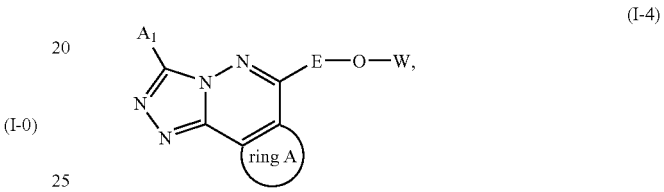

(I-4)

in which $A_2$ and $W_2$ together form the ring A.

The ring A is a benzene ring, or a 5- or 6-membered heteroaryl ring having, in the ring, from 1 to 3 hetero atoms selected from a group consisting of a nitrogen atom, a sulfur atom and an oxygen atom. Preferably, the ring A is a benzene ring, or a heteroaryl ring having 1 or 2 nitrogen atoms as the hetero ring-constituting atoms thereof.

For example, the ring A is preferably a benzene ring, a pyridine ring, a thiophene ring, a furan ring or a pyrazine ring, more preferably a benzene ring, a pyridine ring or a pyrimidine ring, even more preferably a benzene ring or a pyridine ring.

Any of the above-mentioned preferred embodiments of $A_1$, $A_2$, $A_3$, $A_4$, E, W, $W_1$, $W_2$, $G_1$, $G_2$, m1, m2, m3, the substituent groups α, β, γ, δ and ring A described hereinabove may be combined in any manner.

The compounds of formula (I):

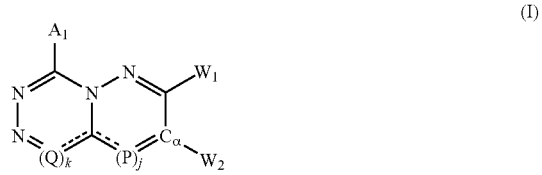

(I)

[in the formula, the symbols have the same meanings as above] include, for example, the following:

2-[4-(3-piperidin-1-ylpropoxy)-phenyl]-3aH-pyrazolo[1,5-d][1,2,4]triazine,

2-[4-(1-cyclopentyl-piperidin-4-yloxy)phenyl]-3aH-pyrazolo[1,5-d][1,2,4]triazine trifluoroacetate, 3-methyl-2-[4-(3-piperidin-1-ylpropoxy)-phenyl]-3aH-pyrazolo[1,5-d][1,2,4]triazine, 3-ethyl-2-[4-(3-piperidin-1-ylpropoxy)phenyl]-3aH-pyrazolo[1,5-d][1,2,4]triazine, 7-methyl-2-[4-(3-piperidin-1-ylpropoxy)-phenyl]-3aH-pyrazolo[1,5-d][1,2,4]triazine, 7-(5-methyl-isoxazol-3-yl)-2-[4-(3-piperidin-1-ylpropoxy)-phenyl]-3aH-pyrazolo[1,5-d][1,2,4]triazine, 7-phenyl-2-[4-(3-piperidin-1-ylpropoxy)-phenyl]-3aH-pyrazolo[1,5-d][1,2,4]triazine, 3-methyl-7-phenyl-2-[4-(3-piperidin-1-ylpropoxy)-phenyl]-3aH-pyrazolo[1,5-d][1,2,4]triazine, 3-methyl-2-[4-(3-piperidin-1-ylpropoxy)-phenyl]-7-(pyridin-3-yl)-3aH-pyrazolo[1,5-d][1,2,4]triazine, 6-[4-(3-piperidin-1-ylpropoxy)-phenyl]-[1,2,4]triazolo[4,3-b]pyridazine, 7-methyl-6-[4-(3-piperidin-1-ylpropoxy)-phenyl]-[1,2,4]triazolo[4,3-b]pyridazine, 3-methyl-6-[4-(3-piperidin-1-ylpropoxy)-phenyl]-[1,2,4]triazolo[4,3-b]pyridazine, 6-[4-(3-piperidin-1-ylpropoxy)-phenyl]-3-trifluoromethyl-[1,2,4]triazolo[4,3-b]pyridazine, 3-tert-butyl-6-[4-(3-piperidin-1-ylpropoxy)-phenyl]-[1,2,4]triazolo[4,3-b]pyridazine, 3-phenyl-6-[4-(3-piperidin-1-ylpropoxy)-phenyl]-[1,2,4]triazolo[4,3-b]pyridazine, 6-[4-(3-piperidin-1-ylpropoxy)-phenyl]-3-(pyridin-2-yl)-[1,2,4]triazolo[4,3-b]pyridazine, 6-[4-(3-piperidin-1-ylpropoxy)-phenyl]-3-(pyridin-3-yl)-[1,2,4]triazolo[4,3-b]pyridazine, 7-methyl-3-phenyl-6-[4-(3-piperidin-1-ylpropoxy)-phenyl]-[1,2,4]triazolo[4,3-b]pyridazine, 6-methyl-7-[4-(3-piperidin-1-ylpropoxy)-phenyl]-[1,2,4]triazolo[4,3-b]pyridazine, 3,6-dimethyl-7-[4-(3-piperidin-1-ylpropoxy)-phenyl]-[1,2,4]triazolo[4,3-b]pyridazine, 6-methyl-3-phenyl-[4-(3-piperidin-1-ylpropoxy)-phenyl]-[1,2,4]triazolo[4,3-b]pyridazine, 6-[4-(3-piperidin-1-ylpropoxy)-phenyl]-pyrido[3,2-d][1,2,4]triazolo[4,3-b]pyridazine, 3-phenyl-6-[4-(3-piperidin-1-ylpropoxy)-phenyl]-pyrido[2,3-d][1,2,4]triazolo[4,3-b]pyridazine, 3-phenyl-6-[6-(3-piperidin-1-ylpropyl)-pyridin-3-yl-methoxy]-[1,2,4]triazolo[3,4-a]phthalazine, 3-phenyl-6-[4-(3-piperidin-1-ylpropoxy)-phenyl]-[1,2,4]triazolo[3,4-a]phthalazine, 6-[4[(3-piperidin-1-ylpropoxy)phenyl]-3-(pyridin-3-yl)-[1,2,4]triazolo[3,4-a]phthalazine, 6-[4-(3-piperidin-1-ylpropoxy)-phenyl]-3-(pyridin-2-yl)-[1,2,4]triazolo[3,4-a]phthalazine, 3-phenyl-6-[4-(3-piperidin-1-ylpropoxy)-phenyl]-pyrido[3,2-d][1,2,4]triazolo[4,3-b]pyridazine, 6-[4-(3-piperidin-1-ylpropoxy)-phenyl]-pyrido[2,3-d][1,2,4]triazolo[4,3-b]pyridazine, 3-methyl-6-[4-(3-piperidin-1-ylpropoxy)-phenyl]-pyrido[3,2-d][1,2,4]triazolo[4,3-b]pyridazine, 3-methyl-6-[4-(3-piperidin-1-ylpropoxy)-phenyl]-pyrido[2,3-d][1,2,4]triazolo[4,3-b]pyridazine, 6-[4-(3-piperidin-1-ylpropoxy)-phenyl]-[1,2,4]triazolo[3,4-a]phthalazine, 3-methyl-6-[4-(3-piperidin-1-ylpropoxy)-phenyl]-[1,2,4]triazolo[3,4-a]phthalazine, 6-[4-(3-piperidin-1-ylpropoxy)-phenyl]-3-trifluoromethyl-[1,2,4]triazolo[3,4-a]phthalazine, 3-tert-butyl-6-[4-(3-piperidin-1-ylpropoxy)-phenyl]-[1,2,4]triazolo[3,4-a]phthalazine, 6-[4-(1-cyclopentyl-piperidin-4-yloxy)-phenyl]-[1,2,4]triazolo[4,3-b]pyridazine, 6-[4-(1-cyclobutyl-piperidin-4-yloxy)-phenyl]-[1,2,4]triazolo[4,3-b]pyridazine, 6-[4-(1-cyclopentyl-piperidin-4-yloxy)-phenyl]-3-methyl-[1,2,4]triazolo[4,3-b]pyridazine, 6-[4-(1-cyclopentyl-piperidin-4-yloxy)-phenyl]-7-methyl-[1,2,4]triazolo[4,3-b]pyridazine, 7-[4-(3-piperidin-1-ylpropoxy)-phenyl]-[1,2,4]triazolo[4,3-b]pyridazine, 7-[4-(1-cyclopentyl-piperidin-4-yloxy)-phenyl]-3-methyl-[1,2,4]triazolo[4,3-b]pyridazine, 7-[4-(1-cyclopentyl-piperidin-4-yloxy)-phenyl]-6-methyl-[1,2,4]triazolo[4,3-b]pyridazine, 7-[4-(1-cyclopentyl-piperidin-4-yloxy)-phenyl]-3,6-dimethyl-[1,2,4]triazolo[4,3-b]pyridazine, 7-[4-(1-cyclopentyl-piperidin-4-yloxy)-phenyl]-[1,2,4]triazolo[4,3-b]pyridazine, 7-[4-(1-cyclobutyl-piperidin-4-yloxy)-phenyl]-[1,2,4]triazolo[4,3-b]pyridazine, 6-[4-(1-cyclopentyl-piperidin-4-yloxy)-phenyl]-[1,2,4]triazolo[3,4-a]phthalazine, 6-[4-(1-cyclopentyl-piperidin-4-yloxy)-phenyl]-3-methyl-[1,2,4]triazolo[3,4-a]phthalazine, 6-[4-(3-pyrrolidin-1-ylpropoxy)-phenyl]-[1,2,4]triazolo[4,3-b]pyridazine, 3-methyl-7-[4-(3-piperidin-1-ylpropoxy)-phenyl]-[1,2,4]triazolo[4,3-b]pyridazine, 7-[4-(1-cyclobutyl-piperidin-4-yloxy)-phenyl]-3-methyl-[1,2,4]triazolo[4,3-b]pyridazine, 6-[4-(1-cyclobutyl-piperidin-4-yloxy)-phenyl]-3-methyl-[1,2,4]triazolo[4,3-b]pyridazine, 6-[4-(1-cyclobutyl-piperidin-4-yloxy)-phenyl]-[1,2,4]triazolo[3,4-a]phthalazine, 6-[4-(1-cyclobutyl-piperidin-4-yloxy)-phenyl]-7-methyl-[1,2,4]triazolo[4,3-b]pyridazine, 7-[4-(1-cyclobutyl-piperidin-4-yloxy)-phenyl]-6-methyl-[1,2,4]triazolo[4,3-b]pyridazine, 7-[4-(1-cyclobutyl-piperidin-4-yloxy)-phenyl]-3,6-dimethyl-[1,2,4]triazolo[4,3-b]pyridazine, 6-[4-(1-cyclobutyl-piperidin-4-yloxy)-phenyl]-3-methyl-[1,2,4]triazolo[3,4-a]phthalazine, 6-{4-[3-(2,6-dimethylpiperizin-1-yl)propoxy]-phenyl}-[1,2,4]triazolo[4,3-b]pyridazine, 6-{4-[3-(2,5-dimethylpyrrolidin-1-yl)propoxy]-phenyl}-[1,2,4]triazolo[4,3-b]pyridazine, N-methyl-6-[4-(3-piperidin-1-ylpropoxy)phenyl]-[1,2,4]triazolo[4,3-b]pyridazine-3-carboxamide, 3-(piperidin-1-ylcarbonyl)-6-[4-(3-piperidin-1-ylpropoxy)phenyl]-[1,2,4]triazolo[4,3-b]pyridazine, 6-[4-(3-methylpiperidin-1-yl)propoxy)-phenyl]-[1,2,4]triazolo[4,3-b]pyridazine, 6-[4-{3-[(3S)-3-fluoropyrrolidin-1-yl]propoxy}-phenyl)-[1,2,4]triazolo[4,3-b]pyridazine, 6-{4-[3-(3-methylpiperidin-1-yl)propoxy]-phenyl}-[1,2,4]triazolo[4,3-b]pyridazine, 6-{4-[3-(4-fluoropiperidin-1-yl)propoxy]-phenyl}-[1,2,4]triazolo[4,3-b]pyridazine, 6-{4-[3-(3-fluoropiperidin-1-yl)propoxy]-phenyl}-[1,2,4]triazolo[4,3-b]pyridazine, 6-[4-{3-[(2R)-(2-methylpyrrolidin-1-yl]propoxy)-phenyl}-[1,2,4]triazolo[4,3-b]pyridazine, 6-[4-{3-[(2S)-(2-methylpyrrolidin-1-yl)propoxy)-phenyl}-[1,2,4]triazolo[4,3-b]pyridazine, N,N-dimethyl-6-[4-{3-[(2R)-2-methylpyrrolidin-1-yl]propoxy)-phenyl}-[1,2,4]triazolo[3,4-a]phthalazine-3-carboxamide, 6-[4-(3-piperidin-1-ylpropoxy)-phenyl]-pyrido[3,4-d][1,2,4]triazolo[4,3-b]pyridazine, 6-[4-(3-pyrrolidin-1-ylpropoxy)-phenyl]-pyrido[3,4-d][1,2,4]triazolo[4,3-b]pyridazine, 6-[4-{3-[(3S)-3-methylpiperidin-1-yl]propoxy}-phenyl]-pyrido[3,4-d][1,2,4]triazolo[4,3-b]pyridazine, 3-methyl-6-[4-(3-piperidin-1-ylpropoxy)-phenyl]-pyrido[3,
4-d][1,2,4]triazolo[4,3-b]pyridazine,
3-methyl-6-[4-(3-pyrrolidin-1-ylpropoxy)-phenyl]-pyrido
[3,4-d][1,2,4]triazolo[4,3-b]pyridazine,
3-methyl-6-[4-{3-[(3S)-3-methylpiperidin-1-yl]propoxy}-
phenyl]-pyrido[3,4-d][1,2,4]triazolo[4,3-b]pyridazine,
6-[4-{3-[(2R)-2-methylpyrrolidin-1-yl]propoxy}-phenyl]-
pyrido[3,4-d][1,2,4]triazolo[4,3-b]pyridazine,
3-methyl-6-[4-{3-[(2R)-2-methylpyrrolidin-1-yl]propoxy}-
phenyl]-pyrido[3,4-d][1,2,4]triazolo[4,3-b]pyridazine,
6-[4-(1-isopropylpiperidin-4-yloxy)phenyl]pyrido[3,4-d][1,
2,4]triazolo[4,3-b]pyridazine,
6-[4-(1-cyclobutylpiperidin-4-yloxy)phenyl]pyrido[3,4-d]
[1,2,4]triazolo[4,3-b]pyridazine,
6-[4-(1-cyclopentylpiperidin-4-yloxy)phenyl]pyrido[3,4-d]
[1,2,4]triazolo[4,3-b]pyridazine,
6-[4-(1-isopropylpiperidin-4-yloxy)phenyl]-3-methyl-py-
rido[3,4-d][1,2,4]triazolo[4,3-b]pyridazine,
6-[4-(1-cyclobutylpiperidin-4-yloxy)phenyl]-3-methylpy-
rido[3,4-d][1,2,4]triazolo[4,3-b]pyridazine,
6-[4-(1-cyclopentylpiperidin-4-yloxy)phenyl]-3-methylpy-
rido[3,4-d][1,2,4]triazolo[4,3-b]pyridazine,
3-methyl-6-[4-(3-pyrrolidin-1-ylpropoxy)-phenyl]-pyrido
[3,2-d][1,2,4]triazolo[4,3-b]pyridazine,
3-methyl-6-[4-(3-pyrrolidin-1-ylpropoxy)-phenyl]-pyrido
[2,3-d][1,2,4]triazolo[4,3-b]pyridazine,
3-methyl-6-(4-{3-[(3S)-3-methylpiperidin-1-yl]propoxy}-
phenyl)-pyrido[3,2-d][1,2,4]triazolo[4,3-b]pyridazine,
3-methyl-6-(4-{3-[(3S)-3-methylpiperidin-1-yl]propoxy}-
phenyl)-pyrido[2,3-d][1,2,4]triazolo[4,3-b]pyridazine,
3-methyl-6-(4-{3-[(2R)-3-methylpyrrolidin-1-yl]propoxy}-
phenyl)-pyrido[3,2-d][1,2,4]triazolo[4,3-b]pyridazine,
3-methyl-6-(4-{3-[(2R)-3-methylpyrrolidin-1-yl]propoxy}-
phenyl)-pyrido[2,3-d][1,2,4]triazolo[4,3-b]pyridazine,
6-[4-(1-isopropylpiperidin-4-yloxy)phenyl]-3-methylpyrido
[3,2-d][1,2,4]triazolo[4,3-b]pyridazine,
6-[4-(1-isopropylpiperidin-4-yloxy)phenyl]-3-methylpyrido
[2,3-d][1,2,4]triazolo[4,3-b]pyridazine,
6-[4-(1-cyclobutylpiperidin-4-yloxy)phenyl]-3-methylpy-
rido[3,2-d][1,2,4]triazolo[4,3-b]pyridazine,
6-[4-(1-cyclobutylpiperidin-4-yloxy)phenyl]-3-methylpy-
rido[2,3-d][1,2,4]triazolo[4,3-b]pyridazine,
6-[4-(1-cyclopentylpiperidin-4-yloxy)phenyl]-3-methylpy-
rido[3,2-d][1,2,4]triazolo[4,3-b]pyridazine,
6-[4-(1-cyclopentylpiperidin-4-yloxy)phenyl]-3-methylpy-
rido[2,3-d][1,2,4]triazolo[4,3-b]pyridazine,
6-[4-(1-isopropylpiperidin-4-yloxy)phenyl]pyrido[3,2-d][1,
2,4]triazolo[4,3-b]pyridazine,
6-[4-(1-isopropylpiperidin-4-yloxy)phenyl]pyrido[2,3-d][1,
2,4]triazolo[4,3-b]pyridazine,
6-[4-(1-cyclobutylpiperidin-4-yloxy)phenyl]pyrido[3,2-d]
[1,2,4]triazolo[4,3-b]pyridazine,
6-[4-(1-cyclobutylpiperidin-4-yloxy)phenyl]pyrido[2,3-d]
[1,2,4]triazolo[4,3-b]pyridazine,
6-[4-(1-cyclopentylpiperidin-4-yloxy)phenyl]pyrido[3,2-d]
[1,2,4]triazolo[4,3-b]pyridazine,
6-[4-(1-cyclopentylpiperidin-4-yloxy)phenyl]pyrido[2,3-d]
[1,2,4]triazolo[4,3-b]pyridazine,
6-[6-(3-piperidin-1-ylpropoxy)pyridin-3-yl]-[1,2,4]triazolo
[3,4-a]phthalazine,
6-{6-[(3S)-3-piperidin-1-ylpropoxy]pyridin-3-yl}-[1,2,4]
triazolo[3,4-a]phthalazine.

Methods for producing the compounds of the invention are
described below.

The compounds (I) of the invention may be produced,
using known reaction methods or according to per-se known
methods. The compounds (I) of the invention may be pro-
duced not only according to ordinary liquid-phase production
methods but also according to any solid-phase methods such
as combinatorial production methods or parallel production
methods that are being significantly developed these days.

Compounds (I-11) of the invention may be produced, for
example, according to the following methods:

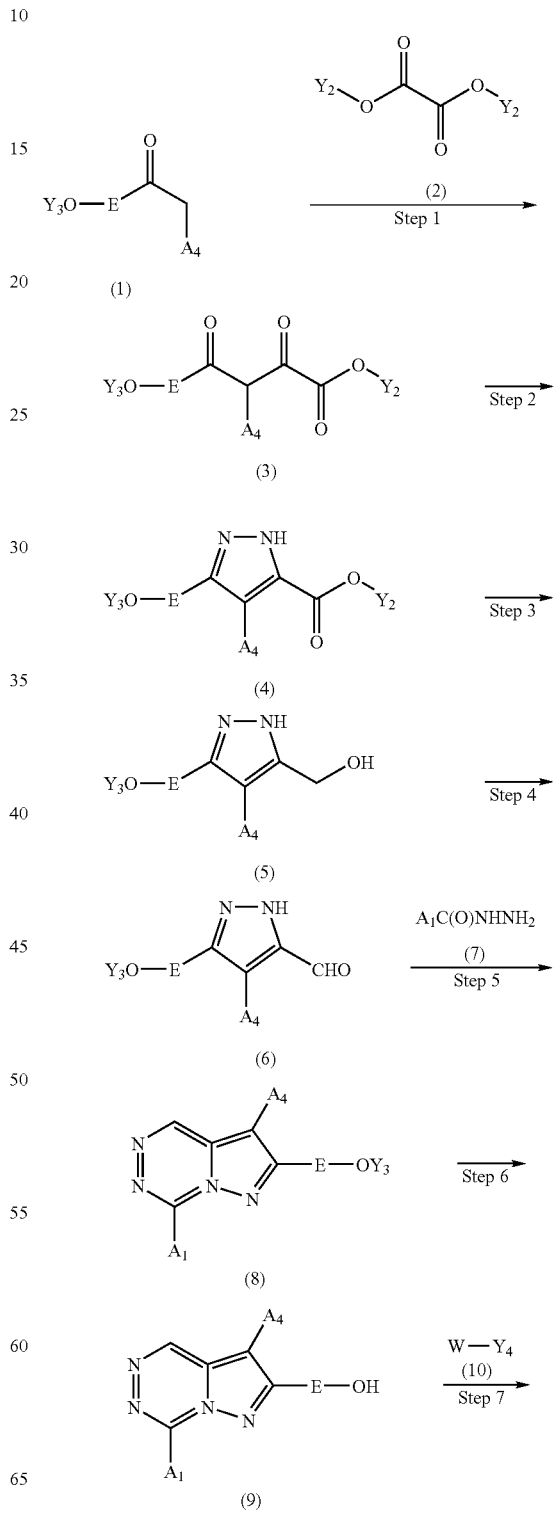

-continued

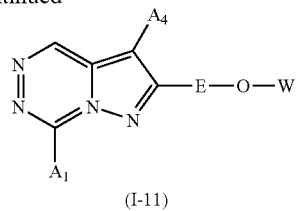

(I-11)

[In the formulae, $Y_2$ represents a linear or branched lower alkyl group, a cycloalkyl group or an aralkyl group; $Y_3$ represents a lower alkyl group or an aralkyl group; $Y_4$ represents a halogen atom, or an organic sulfonyloxy group such as a methanesulfonyloxy group, an ethanesulfonyloxy group, a p-toluenesulfonyloxy group or a trifluoromethanesulfonyloxy group; and the other symbols have the same meanings as above.]

(Step 1)

This step is to produce a compound (3) by reacting a compound (1) with an oxalate derivative (2) in the presence of a base.

$Y_3$ in the compound (1) means the above-defined lower alkyl group or aralkyl group, and more concretely includes, for example, a methyl group, an ethyl group, a benzyl group.

$A_1$ in the compound (1) includes the same groups as defined hereinabove.

$Y_2$ in the compound (2) is a linear or branched lower alkyl group, a cycloalkyl group or an aralkyl group.

"Linear lower alkyl group" for $Y_2$ includes more concretely, for example, a methyl group, an ethyl group, an n-propyl group, an n-butyl group.

"Branched lower alkyl group" for $Y_2$ includes more concretely, for example, a tert-butyl group, a 2-methylpropyl group.

"Cycloalkyl group" for $Y_2$ includes more concretely, for example, a cyclohexyl group.

"Aralkyl group" for $Y_2$ includes more concretely, for example, a benzyl group.

The amount of the compound (2) to be used in this step may be generally from 1 equivalent to an excessive equivalent relative to 1 equivalent of the compound (1).

The base to be used in this step includes, for example, sodium hydride, sodium methoxide, sodium ethoxide, lithium hexamethyldisilazane. Of those, preferred is sodium hydride.

The amount of the base to be used in this step may be generally from 1 equivalent to an excessive equivalent relative to 1 equivalent of the compound (1).

The reaction temperature may be generally from −50° C. to 100° C., preferably from −20° C. to 50° C.

The reaction time may be generally from 5 minutes to 7 days, preferably from 30 minutes to 24 hours.

The reaction solvent to be used in this step is not specifically defined and may be any one not interfering with the reaction. Concretely, it includes, for example, toluene, benzene, xylene, diethyl ether, dioxane, hexane, tetrahydrofuran.

Thus obtained, the compound (3) may be isolated and purified in any known separation and purification method of, for example, concentration, concentration under reduced pressure, solvent extraction, crystallization, reprecipitation, chromatography; or not isolated and purified, it may be subjected to the next step.

(Step 2)

This step is to produce a compound (4) by reacting the compound (3) obtained in the previous step 1, with hydrazine.

The amount of hydrazine to be used in this step may be generally from 1 equivalent to an excessive equivalent relative to 1 equivalent of the compound (3).

The reaction temperature may be generally from 0° C. to 200° C., preferably from room temperature to the boiling point of the solvent used in the reaction.

The reaction time may be generally from 30 minutes to 7 days, preferably from 1 hour to 24 hours.

The reaction solvent to be used in this step is not specifically defined and may be any one not interfering with the reaction. Concretely, it includes, for example, ethanol, methanol, acetic acid.

Thus obtained, the compound (4) may be isolated and purified in any known separation and purification method of, for example, concentration, concentration under reduced pressure, solvent extraction, crystallization, reprecipitation, chromatography; or not isolated and purified, it may be subjected to the next step.

(Step 3)

This step is to produce a compound (5) by reducing the ester group of the compound (4) obtained in the previous step 2.

The reducing agent to be used in this step concretely includes, for example, lithium aluminium hydride, lithium borohydride.

The amount of the reducing agent to be used in this step may be generally from 1 equivalent to an excessive equivalent, preferably from 1 equivalent to 1.5 equivalents relative to 1 equivalent of the compound (4).

The reaction temperature may be generally from −50° C. to 100° C., preferably from −20 to 50° C.

The reaction time may be generally from 5 minutes to 24 hours, preferably from 30 minutes to 24 hours.

The reaction solvent to be used in this step is not specifically defined and may be any one not interfering with the reaction. Concretely, it includes, for example, tetrahydrofuran, diethyl ether.

Thus obtained, the compound (5) may be isolated and purified in any known separation and purification method of, for example, concentration, concentration under reduced pressure, crystallization, solvent extraction, reprecipitation, chromatography; or not isolated and purified, it may be subjected to the next step.

(Step 4)

This step is to produce an aldehyde compound (6) by oxidizing the compound (5) obtained in the previous step 3.

The oxidizing agent to be used in this step concretely includes, for example, manganese dioxide, chromium oxide, pyridinium chlorochromate, pyridinium bichromate, selenium dioxide, dimethylsulfoxide.

The amount of the oxidizing agent to be used in this step may be generally from 1 equivalent to an excessive equivalent, preferably from 5 equivalents to 20 equivalents relative to 1 equivalent of the compound (4).

The reaction temperature may be generally from 0° C. to 200° C., preferably from 50° C. to the boiling point of the solvent used in the reaction.

The reaction time may be generally from 5 minutes to 7 days, preferably from 30 minutes to 24 hours.

The reaction solvent to be used in this step is not specifically defined and may be any one not interfering with the reaction. Concretely, it includes, for example, tetrahydrofuran, diethyl ether, dichloromethane, chloroform, acetone, benzene, toluene, xylene.

Thus obtained, the compound (6) may be isolated and purified in any known separation and purification method of, for example, concentration, concentration under reduced pressure, crystallization, solvent extraction, reprecipitation, chromatography; or not isolated and purified, it may be subjected to the next step.

(Step 5)

This step is to produce a compound (8) by reacting the compound (6) obtained in the previous step 4, with a hydrazide derivative, $A_1C(O)NHNH_2$ in the presence of a base.

The base to be used in this step is concretely, for example, triethylamine.

The amount of the base to be used in this step may be generally from 1 equivalent to an excessive equivalent, preferably from 1 equivalent to 1.5 equivalents relative to 1 equivalent of the compound (6).

$A_1$ in the hydrazide derivative (7) to be used in this step may have the same meaning as that defined hereinabove, and more concretely includes, for example, a hydrogen atom, a methyl group, an ethyl group, an n-propyl group, an n-butyl group, an isopropyl group, a tert-butyl group, a phenyl group, a pyridin-2-yl group, a pyridin-3-yl group, a pyridin-4-yl group, a furan-2-yl group, a thiophen-2-yl group, an indol-3-yl group, a 5-methylisoxazol-3-yl group.

The hydrazide derivative (7) to be used in this step may be a commercially-available one, or may be produced by reacting an ester derivative, $A_1C(O)OY_5$ (wherein $Y_5$ is a lower alkyl group such as a methyl group, an ethyl group) with hydrazine in a reaction solvent such as ether according to a method generally employed in the field of organic chemistry.

The amount of the hydrazide derivative (7) to be used in this step may be generally from 1 equivalent to an excessive equivalent, preferably from 1 equivalent to 1.5 equivalents relative to 1 equivalent of the compound (6).

The reaction temperature may be generally from 0° C. to 200° C., preferably from 50° C. to the boiling point of the solvent used in the reaction.

The reaction time may be generally from 5 minutes to 7 days, preferably from 1 hour to 24 hours.

The reaction solvent to be used in this step is not specifically defined and may be any one not interfering with the reaction. Concretely, it includes, for example, xylene, toluene, dioxane, tetrahydrofuran, dimethylformamide, N-methylpyrrolidone, quinoline.

Thus obtained, the compound (8) may be isolated and purified in any known separation and purification method of, for example, concentration, concentration under reduced pressure, crystallization, solvent extraction, reprecipitation, chromatography; or not isolated and purified, it may be subjected to the next step.

(Step 6)

This step is to produce a compound (9) by removing $Y_3$ from the compound (8) obtained in the previous step 5.

For removing $Y_3$, concretely employable is a method of using, for example, boron tribromide or trimethylsilyl iodide.

The amount of boron tribromide to be used in this step may be generally from 1 equivalent to an excessive equivalent, preferably from 1.5 equivalents to 2 equivalents relative to 1 equivalent of the compound (8).

The reaction temperature may be generally from –20° C. to 100° C., preferably from 0° C. to room temperature.

The reaction time may be generally from 5 minutes to 7 days, preferably from 1 hour to 24 hours.

The reaction solvent to be used in this step is not specifically defined and may be any one not interfering with the reaction. Concretely, it includes, for example, chloroform, methylene chloride, carbon tetrachloride.

Thus obtained, the compound (9) may be isolated and purified in any known separation and purification method of, for example, concentration, concentration under reduced pressure, crystallization, solvent extraction, reprecipitation, chromatography; or not isolated and purified, it may be subjected to the next step.

(Step 7)

This step includes the following:

(Step 7-1) for producing a compound (I-1 1) of the invention by reacting a compound (9) and a compound

(10) $W-Y_4$ in the presence of a base, or (Step 7-2) for producing a compound (I-2) of the invention by reacting a compound (9) and a compound (10-1) $Wp-Y_4$ (wherein p indicates a protective group for the amino group in formula (II-1), (II-2) or (II-3)) in the presence of a base, followed by removing the protective group of the amino group.

The amount of the compound (10) or (10-1) to be used in this step may be generally from 1 equivalent to an excessive equivalent, preferably from 1 equivalent to 1.5 equivalents relative to 1 equivalent of the compound (9).

When a compound (10-1) is used in the reaction with the compound (9), then the amino-protective group may be removed according to a method described in literature (for example, *Protective Groups in Organic Synthesis*, written by T. W. Green, 2nd Ed., by John Wiley & Sons, 1991), or a method similar to it, or a combination of the method with an ordinary method.

The base to be used in this step includes, for example, inorganic bases such as sodium hydroxide, potassium hydroxide, sodium hydrogencarbonate, sodium carbonate, potassium carbonate, cesium carbonate; and organic bases such as triethylamine, diisopropylamine.

The amount of the base to be used may be generally from 1 equivalent to an excessive equivalent, preferably from 1 equivalent to an excessive equivalent relative to 1 equivalent of the compound (9).

The reaction temperature may be generally from 0° C. to 200° C., preferably from room temperature to the boiling point of the solvent used in the reaction.

The reaction time may be generally from 5 minutes to 7 days, preferably from 1 hour to 24 hours.

The reaction solvent to be used in this step is not specifically defined and may be any one not interfering with the reaction. Concretely, it includes, for example, tetrahydrofuran, dioxane, dimethylformamide.

Thus obtained, the compound (I-2) of the invention may be isolated and purified in any known separation and purification method of, for example, concentration, concentration under reduced pressure, crystallization, solvent extraction, reprecipitation, chromatography.

The compounds (I-2) of the invention may also be produced according to the following method:

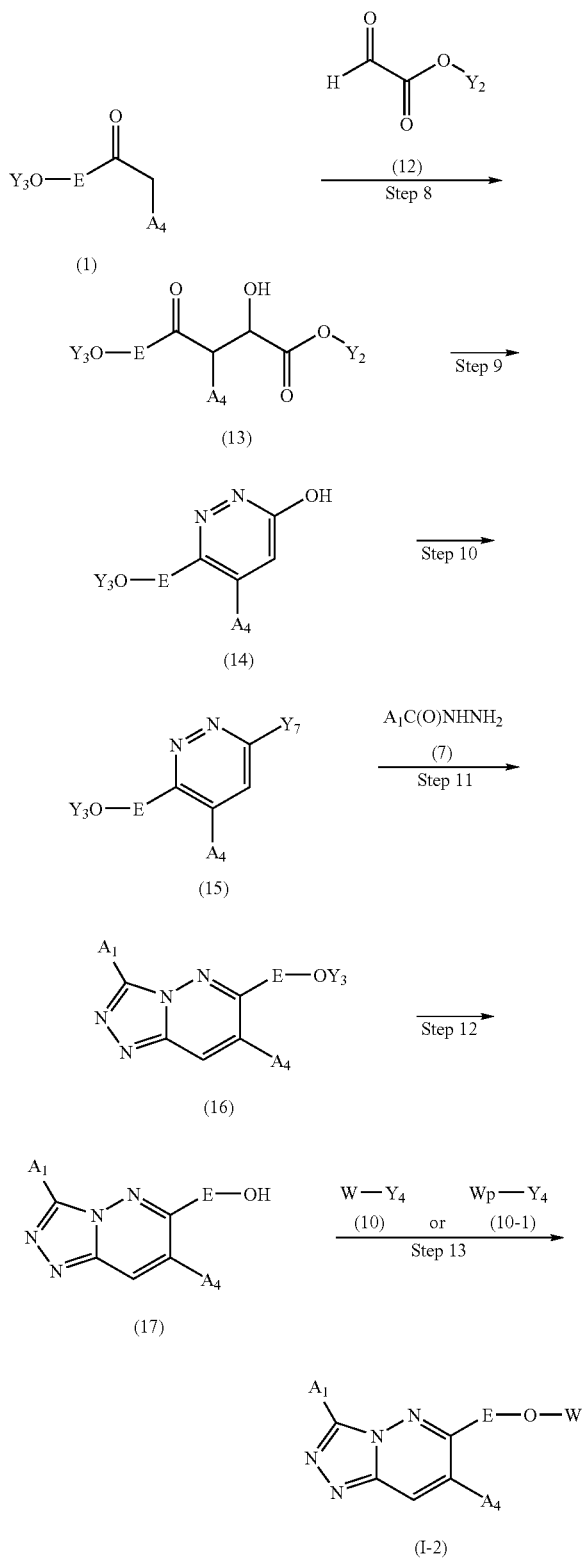

[In the formulae, $Y^7$ represents a leaving group, and the other symbols have the same meanings as above.]

(Step 8)

This step is to produce a compound (13) by reacting the compound (1) with a compound (12) in the presence of a base.

The reaction in this step may be effected in the same manner as in the step 1, or according to a method similar to it, or according to a combination of the method with an ordinary method.

Thus obtained, the compound (13) may be isolated and purified in any known separation and purification method of, for example, concentration, concentration under reduced pressure, crystallization, solvent extraction, reprecipitation, chromatography; or not isolated and purified, it may be subjected to the next step.

(Step 9)

This step is to produce a compound (14) by reacting the compound (13) with hydrazine.

The reaction in this step may be effected in the same manner as in the step 2, or according to a method similar to it, or according to a combination of the method with an ordinary method.

Thus obtained, the compound (14) may be isolated and purified in any known separation and purification method of, for example, concentration, concentration under reduced pressure, crystallization, solvent extraction, reprecipitation, chromatography; or not isolated and purified, it may be subjected to the next step.

(Step 10)

This step is to produce a compound (15) by converting the hydroxyl group of the compound (14) into a leaving group $Y^7$.

$Y^7$ is a leaving group, for example, a halogen atom such as a chlorine atom.

In case where $Y^7$ is a chlorine atom, the compound (14) may be reacted with phosphorus oxychloride whereby the hydroxyl group of the compound (14) may be converted into a chlorine atom.

The amount of phosphorus oxychloride to be used in this step may be generally from 1 equivalent to an excessive equivalent, preferably from 10 to 20 equivalents relative to 1 equivalent of the compound (14).

The reaction temperature may be generally from 0° C. to 200° C., preferably from 50° C. to the boiling point of the solvent used in the reaction.

The reaction time may be generally from 5 minutes to 7 days, preferably from 1 hour to 24 hours.

When phosphorus oxychloride is used in this step, then the reaction may be effected in the absence of a solvent. However, a reaction solvent may be used. The reaction solvent usable herein is not specifically defined and may be any one not interfering with the reaction. Concretely, it includes, for example, chloroform, methylene chloride, carbon tetrachloride.

Thus obtained, the compound (26) may be isolated and purified in any known separation and purification method of, for example, concentration, concentration under reduced pressure, crystallization, solvent extraction, reprecipitation, chromatography; or not isolated and purified, it may be subjected to the next step.

(Step 11)

This step is to produce a compound (16) by reacting the compound (15) with a hydrazide derivative (7) $A_1C(O)NHNH_2$.

The hydrazide derivative (7) to be used in this step may be a commercially-available one, or may be produced by reacting a compound, $A_1C(O)OY_5$ (wherein the symbols have the same meanings as above) with hydrazine in a solvent such as ether according to a method generally employed in the field of organic chemistry.

The amount of the hydrazide derivative (7) to be used in this step may be generally from 1 equivalent to an excessive equivalent, preferably from 1.5 equivalents to 2.0 equivalents relative to 1 equivalent of the compound (15).

The reaction temperature may be generally from 0° C. to 200° C., preferably from 100° C. to the boiling point of the solvent used in the reaction.

The reaction time may be generally from 5 minutes to 24 hours, preferably from 5 hours to 14 hours.

The reaction solvent to be used in this step is not specifically defined and may be any one not interfering with the reaction. Concretely, it includes, for example, xylene, toluene, dioxane.

Thus obtained, the compound (16) may be isolated and purified in any known separation and purification method of, for example, concentration, concentration under reduced pressure, solvent extraction, crystallization, reprecipitation, chromatography; or not isolated and purified, it may be subjected to the next step.

(Step 12)

This step is to produce a compound (17) by removing $Y_3$ from the compound (16).

The reaction in this step may be effected in the same manner as in the step 6, or according to a method similar to it, or according to a combination of the method with an ordinary method.

Thus obtained, the compound (17) may be isolated and purified in any known separation and purification method of, for example, concentration, concentration under reduced pressure, crystallization, solvent extraction, reprecipitation, chromatography; or not isolated and purified, it may be subjected to the next step.

(Step 13)

This step includes the following:

(Step 13-1) for producing a compound (I-2) of the invention by reacting the compound (17) and a compound (10) W—$Y_4$ in the presence of a base, or (Step 13-2) for producing a compound (I-2) of the invention by reacting the compound (17) and a compound (10-1) Wp—$Y_4$ (wherein p indicates a protective group for the amino group in formula (II-1), (II-2) or (II-3)) in the presence of a base, followed by removing the protective group of the amino group of the compound (10-1).

The reaction in the step 13-1 may be effected in the same manner as in the step 7-1, or according to a method similar to it, or according to a combination of the method with an ordinary method; and the reaction in the step 13-2 may be effected in the same manner as in the step 7-2, or according to a method similar to it, or according to a combination of the method with an ordinary method.

Thus obtained, the compound (I-2) of the invention may be isolated and purified in any known separation and purification method of, for example, concentration, concentration under reduced pressure, crystallization, solvent extraction, reprecipitation, chromatography.

The compounds (I-3) of the invention may also be produced according to the following method:

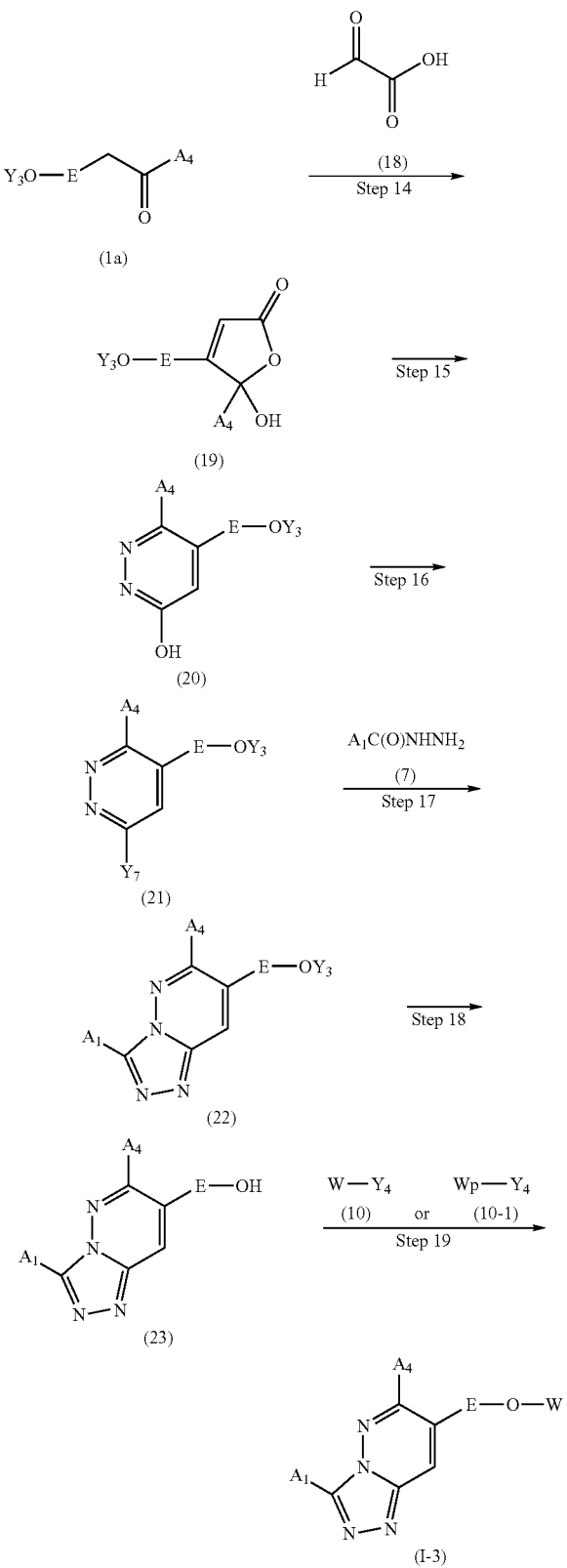

[In the formulae, the symbols have the same meanings as above.]

(Step 14)

This step is to produce a compound (19) by reacting a compound (1a) with glyoxylic acid (18).

The compound (1a) to be used in this step is concretely, for example, 4-methoxyphenylacetone.

The amount of glyoxylic acid (18) to be used in this step may be generally from 1 equivalent to an excessive equivalent, preferably from 1.2 equivalents to 1.5 equivalents relative to 1 equivalent of the compound (1a).

The reaction temperature may be generally from 0° C. to 200° C., preferably from 10° C. to the boiling point of the solvent used in the reaction.

The reaction time may be generally from 1 hour to 24 hours, preferably from 5 hours to 15 hours.

The reaction solvent to be used in this step is not specifically defined and may be any one not interfering with the reaction. For example, it includes water, toluene, tetrahydrofuran, dioxane, dimethylformamide.

Thus obtained, the compound (19) may be isolated and purified in any known separation and purification method of, for example, concentration, concentration under reduced pressure, crystallization, solvent extraction, reprecipitation, chromatography; or not isolated and purified, it may be subjected to the next step.

(Step 15)

This step is to produce a compound (20) by reacting the compound (19) with hydrazine.

The reaction in this step may be effected in the same manner as in the step 2, or according to a method similar to it, or according to a combination of the method with an ordinary method.

Thus obtained, the compound (20) may be isolated and purified in any known separation and purification method of, for example, concentration, concentration under reduced pressure, crystallization, solvent extraction, reprecipitation, chromatography; or not isolated and purified, it may be subjected to the next step.

(Step 16)

This step is to produce a compound (21) by converting the hydroxyl group of the compound (20) into a leaving group $Y^7$.

The reaction in this step may be effected in the same manner as in the step 10, or according to a method similar to it, or according to a combination of the method with an ordinary method.

Thus obtained, the compound (21) may be isolated and purified in any known separation and purification method of, for example, concentration, concentration under reduced pressure, crystallization, solvent extraction, reprecipitation, chromatography; or not isolated and purified, it may be subjected to the next step.

(Step 17)

This step is to produce a compound (22) by reacting the compound (21) with a hydrazide derivative (7) $A^1C(O)NHNH_2$. The reaction in this step may be effected in the same manner as in the step 11, or according to a method similar to it, or according to a combination of the method with an ordinary method.

Thus obtained, the compound (22) may be isolated and purified in any known separation and purification method of, for example, concentration, concentration under reduced pressure, crystallization, solvent extraction, reprecipitation, chromatography; or not isolated and purified, it may be subjected to the next step.

(Step 18)

This step is to produce a compound (23) by removing $Y_3$ from the compound (22).

The reaction in this step may be effected in the same manner as in the step 6, or according to a method similar to it, or according to a combination of the method with an ordinary method.

Thus obtained, the compound (23) may be isolated and purified in any known separation and purification method of, for example, concentration, concentration under reduced pressure, crystallization, solvent extraction, reprecipitation, chromatography; or not isolated and purified, it may be subjected to the next step.

(Step 19)

This step includes the following:

(Step 19-1) for producing a compound (I-3) of the invention by reacting the compound (23) and a compound (10) $W-Y_4$ (wherein W and $Y_4$ have the same meanings as above) in the presence of a base, or (Step 19-2) for producing a compound (I-2) of the invention by reacting the compound (23) and a compound (10-1) $W_p-Y_4$ (wherein W, p and $Y_4$ have the same meanings as above) in the presence of a base, followed by removing the protective group of the amino group.

The reaction in the step 19-1 may be effected in the same manner as in the step 7-1, or according to a method similar to it, or according to a combination of the method with an ordinary method; and the reaction in the step 19-2 may be effected in the same manner as in the step 7-2, or according to a method similar to it, or according to a combination of the method with an ordinary method.

Thus obtained, the compound (I-3) of the invention may be isolated and purified in any known separation and purification method of, for example, concentration, concentration under reduced pressure, crystallization, solvent extraction, reprecipitation, chromatography.

The compounds (I-4) of the invention may be produced, for example, according to the following method:

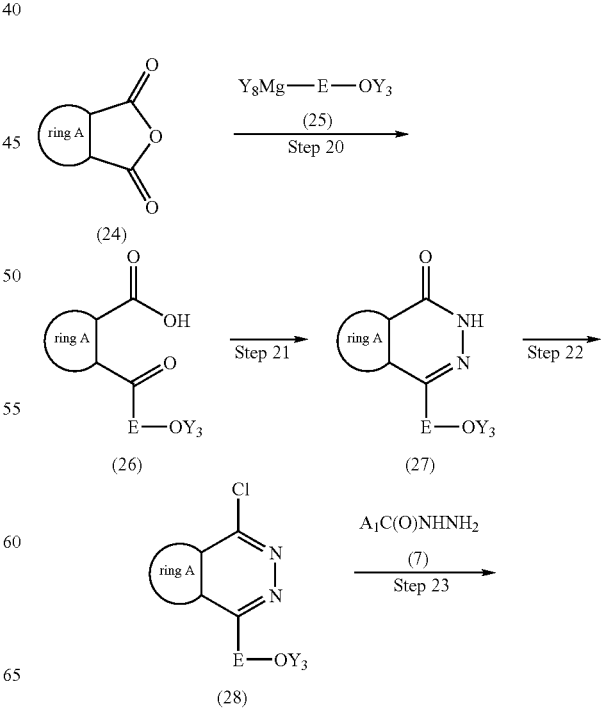

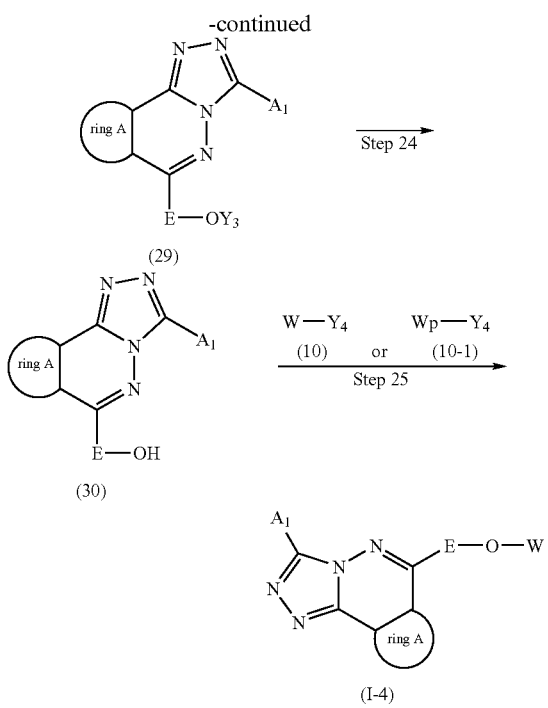

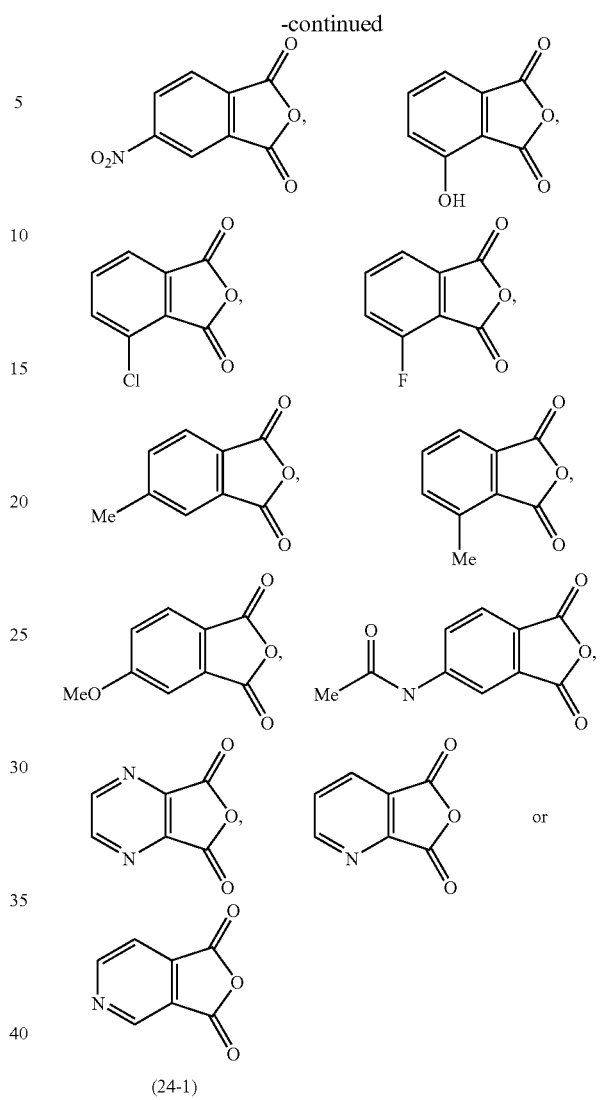

[In the formulae, $Y_8$ represents a halogen atom such as a bromine atom; and the other symbols have the same meanings as above.]

(Step 20)

This step is to produce a compound (26) by reacting a compound (24) with a compound (25).

The compound (25) to be used in this step is a Grignard reagent, which may be any one capable of producing the compound (26) in its reaction with the compound (24). Concretely, for example, it includes 4-methoxyphenylmagnesium bromide, 4-methoxyphenylmagnesium chloride, 4-methoxyphenylmagnesium iodide.

The amount of (25) to be used in this step may be generally from 1 equivalent to an excessive equivalent, preferably from 1.0 equivalent to 1.5 equivalents relative to 1 equivalent of the compound (24).

The reaction temperature may be generally from −50° C. to 200° C., preferably from 0° C. to the boiling point of the solvent used in the reaction.

The reaction time may be generally from 5 minutes to 7 days, preferably from 1 hour to 24 hours.

The reaction solvent to be used in this step is not specifically defined and may be any one not interfering with the reaction. For example, it includes diethyl ether, tetrahydrofuran.

The compound (24) to be used in this step includes, for example, those of a formula (24-1):

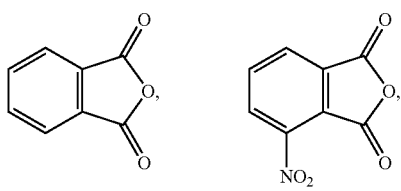

Thus obtained, the compound (26) may be isolated and purified in any known separation and purification method of, for example, concentration, concentration under reduced pressure, crystallization, solvent extraction, reprecipitation, chromatography; or not isolated and purified, it may be subjected to the next step.

(Step 21)

This step is to produce a compound (27) by reacting the compound (26) with hydrazine.

The reaction in this step may be effected in the same manner as in the step 2, or according to a method similar to it, or according to a combination of the method with an ordinary method.

Thus obtained, the compound (27) may be isolated and purified in any known separation and purification method of, for example, concentration, concentration under reduced pressure, crystallization, solvent extraction, reprecipitation, chromatography; or not isolated and purified, it may be subjected to the next step.

(Step 22)

This step is to produce a compound (28) by converting the oxo group of the compound (27) into a leaving group $Y^7$.

The reaction in this step may be effected in the same manner as in the step 10, or according to a method similar to it, or according to a combination of the method with an ordinary method.

In the step 22, when the oxo group is converted into a chorine atom, for example, phosphorus oxychloride may be used.

Regarding the reaction condition including the amount of phosphorus oxychloride to be used, the step 10 or a method similar to it or a combination of the method with an ordinary method may be referred to.

Thus obtained, the compound (28) may be isolated and purified in any known separation and purification method of, for example, concentration, concentration under reduced pressure, crystallization, solvent extraction, reprecipitation, chromatography; or not isolated and purified, it may be subjected to the next step.

(Step 23)

This step is to produce a compound (29) by reacting the compound (28) with a hydrazide derivative (7) $A_1C(O)NHNH_2$.

The reaction in this step may be effected in the same manner as in the step 11, or according to a method similar to it, or according to a combination of the method with an ordinary method.

Thus obtained, the compound (29) may be isolated and purified in any known separation and purification method of, for example, concentration, concentration under reduced pressure, solvent extraction, crystallization, reprecipitation, chromatography; or not isolated and purified, it may be subjected to the next step.

(Step 24)

This step is to produce a compound (30) by removing $Y_3$ from the step (29).

The reaction in this step may be effected through isolation and purification in the same manner as in the step 6, or according to a method similar to it, or according to a combination of the method with an ordinary method, or not through such isolation or purification Thus obtained, the compound (30) may be isolated and purified in any known separation and purification method of, for example, concentration, concentration under reduced pressure, crystallization, solvent extraction, reprecipitation, chromatography; or not isolated and purified, it may be subjected to the next step.

(Step 25)

This step includes the following:

(Step 25-1) for producing a compound (I-4) of the invention by reacting the compound (30) and a compound (10) W—$Y_4$ in the presence of a base, or (Step 25-2) for producing a compound (14) of the invention by reacting the compound (30) and a compound (10-1) Wp-$Y_4$ (wherein the symbols have the same meanings as above) in the presence of a base.

The reaction in the step 25-1 may be effected in the same manner as in the step 7-1, or according to a method similar to it, or according to a combination of the method with an ordinary method; and the reaction in the step 25-2 may be effected in the same manner as in the step 7-2, or according to a method similar to it, or according to a combination of the method with an ordinary method.

Thus obtained, the compound (I-4) of the invention may be isolated and purified in any known separation and purification method of, for example, concentration, concentration under reduced pressure, crystallization, solvent extraction, reprecipitation, chromatography.

The compounds of formula (I) of the invention may be readily isolated and purified through ordinary separation and purification. The method includes, for example, solvent extraction, recrystallization, reprecipitation, column chromatography, preparative thin-layer chromatography.

These compounds may be formed into pharmaceutically-acceptable salts or esters in any ordinary method, or on the contrary, their salts or esters may also be converted into free compounds in any ordinary method.

The nitrogen-containing condensed hetero-aromatic derivatives of the invention may be in the form of pharmaceutically-acceptable salts thereof, and such salts may be produced in any ordinary method using the compounds of formula (I). Their acid-addition salts include, for example, hydrohalides (e.g., hydrofluorides, hydrofluorides, hydrobromides, hydroiodides), inorganic acid salts (e.g., nitrates, perchlorates, sulfates, phosphates, carbonates), lower alkylsulfonates (e.g., methanesulfonates, trifluoromethanesulfonates, ethanesulfonates), arylsulfonates (e.g., benzenesulfonates, p-toluenesulfonates), organic acid salts (e.g., fumarates, succinates, citrates, tartrates, oxalates, maleates), and salts with amino acids (e.g., glutamates, aspartates).

Their base-addition salts include, for example, salts with alkali metals (e.g., sodium salts, potassium salts), salts with alkaline earth metals (e.g., calcium salts, magnesium salts), ammonium salts, salts with organic bases (e.g., guanidine, triethylamine, dicyclohexylamine). Further, the compounds of the invention may be in the form of hydrates or solvates of their free compounds or salts.

The compounds of formula (I) and their pharmaceutically-acceptable salts may be administered orally or parenterally.

In clinical use of the compounds of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into solid preparations (e.g., tablets, capsules, granules, powders and suppositories) and liquid preparations (e.g., syrups, elixirs, injections). These preparations can be produced in any method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto. The preparations may contain the compound of the invention in an amount of from 1.0 to 100% by weight, preferably from 1.0 to 60% by weight of the preparation.

The compounds of the invention may be formulated into preparations, for example, according to the following Formulation Examples.

Formulation Example 1

10 parts of the compound of Example 1 to be described hereinunder, 15 parts of heavy magnesium oxide and 75 parts of lactose were uniformly mixed to prepare a powdery or granular preparation having a particle size of at most 350 μm. The preparation is encapsulated to give capsules.

Formulation Example 2

45 parts of the compound of Example 1 to be described hereinunder, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 μm.

Formulation Example 3

A granular preparation was prepared in the same manner as in Formulation Example 2. 96 parts of the granular preparation is mixed with 3 parts of calcium stearate, and shaped under compression into tablets having a diameter of 10 mm.

Formulation Example 4

90 parts of the granular preparation obtained according to the method of Formulation Example 2 was mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

These preparations may contain any other therapeutically-effective drug, as described below.

In their use, the compounds of the invention may be combined with any other drug effective for treatment (prevention or therapy) of metabolic disorders or dietary disorders. The individual ingredients to be combined may be administered at different times or at the same time, either as one preparation or as divided different preparations. The combination of the compound of the invention with any other drug effective for treatment of metabolic disorders or dietary disorders includes, in principle, combinations thereof with any and every drug effective for treatment of metabolic disorders or dietary disorders.

The compounds of the invention may also be combined with one any other drug effective for hypertension, obesity-related hypertension, hypertension-related disorders, cardiomegaly, left ventricle hypertrophy, metabolic disorders, obesity, obesity-related disorders (these are hereinafter referred to as "co-medicines"). Such co-medicines may be administered at the same time or at different times or successively in order in prevention or treatment of the above-mentioned disorders. When the compound of the invention is used simultaneously with one or more co-medicines, then it may be in a drug composition for one-dose administration. However, in such combination therapy, the composition containing the compound of the invention and the co-medicine may be administered to subjects simultaneously, or separately or successively. The composition and the co-medicine may be packed separately. They may be administered at different times.

The dose of the co-medicine may depend on the clinical use thereof, and may be suitably determined in accordance with the administration subject, the administration route, the diseases and the combination. The form of the co-medicine for administration is not specifically defined, and it may be combined with the compound of the invention when they are administered. The administration mode includes, for example, the following: (1) A compound of the invention is combined with a co-medicine to give a single preparation for single administration; (2) a compound of the invention and a co-medicine are separately formulated into different two preparations, and the two preparations are simultaneously administered in one administration route; (3) a compound of the invention and a co-medicine are separately formulated into different two preparations, and they are administered at different times in one and the same administration route; (4) a compound of the invention and a co-medicine are separately formulated into different two preparations, and they are administered at the same time in two different administration routes; (5) a compound of the invention and a co-medicine are separately formulated into different two preparations, and they are administered at different times in different administration routes (for example, a compound of the invention and a co-medicine are administered in that order, or in an order contrary to this). The blend ratio of the compound of the invention and the co-medicine may be suitably determined depending on the administration subject, the administration route, and the disease for the administration.

The co-medicines usable in the invention includes therapeutical medicines for diabetes, therapeutical medicines for hyperlipemia, therapeutical medicines for hypertension, and medicines for obesity. Two or more such co-medicines may be combined in any desired ratio.

The therapeutical medicines for diabetes includes, for example, the following:

1) PPAR (peroxisome proliferator-activated receptor)-γ agonists such as glitazones (e.g., ciglitazone, darglitazone, englitazone, isaglitazone (MCC-555), pioglitazone, rosiglitazone, troglitazone, BRL49653, CLX-0921, 5-BTZD), GW-0207, LG-100641, LY-300512;

2) biguanides such as metformin, buformin, phenformin;

3) protein tyrosine phosphatase 1B inhibitors;

4) sulfonylureas such as acetohexamide, chloropropamide, diabinese, glibenclamide, glipizide, glyburide, glimepiride, gliclazide, glipentide, gliquidone, glisolamide, trazamide, tolubutamide;

5) meglitinides such as repaglinide, nateglinide;

6) α-glucoside hydrolase inhibitors such as acarbose, adiposine, camiglibose, emiglitate, miglitol, voglibose, pradimicin-Q, salbostatin, CKD-711, MDL-25,673, MDL-73,945, MOR14;

7) α-amylase inhibitors such as tendamistat, trestatin, A13688;

8) insulin secretion promoters such as linoglide, A-4166;

9) fatty acid oxidation inhibitors such as clomoxir, etomoxir;

10) A2 antagonists such as midaglizole, isaglidole, deriglidole, idazoxan, earoxan, fluparoxan;

11) insulin or insulin mimetix such as biota, LP-100, novalapid, insulin determir, insulin lispro, insulin glargine, insulin zinc, Lys-Pro-insulin, GLP-1 (73-7), GLP1 (7-36)-NH$_2$;

12) non-thiazolidinediones such as JT-501, farglitazar;

13) PPARα/γ dual-agonists such as CLX-0940, GW-1536, GW-1929, GW-2433, KPR-297, L-796449, LR-90, and SB219994;

14) other insulin sensitizes, and

15) VPAC2 receptor agonists.

The therapeutical medicines for hyperlipemia include, for example, the following:

1) bile acid absorption promoters such as cholesterylamine, colesevelem, colestipol, crosslinked dextran dialkylaminoalkyl derivatives, Colestid®, LoCholest®, Questran®;

2) HMG-CoA reductase inhibitors such as atorvastatin, itavastatin, fluvastatin, lovastatin, pravastatin, rivastatin, rosuvastatin, simvastatin, ZD-4522;

3) HMG-CoA synthase inhibitors;

4) cholesterol absorption inhibitors such as snatol ester, β-sitosterol, sterol glucoside, ezetimibe;

5) ACAT (acyl-CoA.cholesterol acyltransacylase) inhibitors such as avasimibe, eflucimibe, KY-505, SMP-709;

6) CETP inhibitors such as JTT705, torcetrapib, CP532632, BAY-63-2149, SC-591, SC-795;

7) squalane synthesis inhibitors;

8) antioxidants such as probucol;

9) PPARα agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid®, Lopid®, Tricor®);

10) FXR receptor antagonists such as GW-4064, SR-103912;

11) LXR receptor agonists such as GW3965, T9013137, XTCO-179628;

12) lipoprotein synthesis inhibitors such as niacin;

13) renin-angiotensin system inhibitors;

14) PPARδ partial agonists;

15) bile acid reabsorption inhibitors such as BARA1453, SC435, PHA384640, S435, AZD7706;

16) PPARδ agonists such as GW501516, GW590735;

17) triglyceride synthesis inhibitors;

18) MTTP (microsomic triglyceride transportation) inhibitors such as inplitapide, LAB687, CP346086;

19) transcription modifying factors;

20) squalane epoxidase inhibitors;

21) LDL (low-density lipoprotein) receptor derivatives, 22) platelet agglutination inhibitors;

23) 5-LO (5-lipoxygenase)/FLAP (5-lipoxygenase activated protein) inhibitors; and 24) niacin receptor agonists.

The therapeutical medicines for hypertension include, for example, the following:

1) thiazide diuretics such as chlorothialidon, chlorothiazide, dichlorofenamide, hydrofluorothiazide, indapamide, hydrochlorothiazide; loop diuretics such as bumetanide, ethacrynic acid, flosemide, tolusemide; sodium diuretics such as amyloride, triamuteren; aldosterone antagonist diuretics such as spironolactone, epilenone;

2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tertatolol, tilisolol, timolol;

3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil;

4) angiotensin converting enzymes such as benazepril, captopril, cilazapril, delapril, enalapril, fosinopril, imidapril, rosinopril, moexipril, quinapril, quinaprilat, ramipril, perindopril, perindropril, quanipril, spirapril, tenocapril, trandolapril, zofenopril;

5) neutral endopeptidase inhibitors such as omapatrilat, cadoxatril, ecadotril, fosidotril, sampatrilat, AVE7688, ER4030;

6) endothelin antagonists such as tezosentan, A308165, YM62899;

7) vasodilators such as hydraladine, clonidine, minoxidil, nicotinyl alcohol;

8) angiotensin II receptor antagonists such as candesartan, eporsartan, iribesartan, Losartan, pratosartan, tasosartan, telmisartan, balsartan, EXP-3137, F16828K, RNH6270;

9) α/β adrenalin blockers such as nipradilol, arotinolol, amoslalol;

10) α1 blockers such as terazosin, urapidil, prazosin, bunazosin, trimazosin, doxazosin, naphthopidil, indolamin, WHIP164, XEN010;

11) α2 agonists such as lofexidine, tiamenidine, moxonidine, rilmenidine, guanobenz; and 12) aldosterone inhibitors.

The anti-obesity medicines include, for example, the following:

1) 5HT (serotonin) transporter inhibitors such as paroxetine, fluoxetine, fenfluramine, fluvoxamine, sertraline, imipramine;

2) NE (norepinephrine) transporter inhibitors such as GW320659, desipramine, talsupram, nomifensin;

3) CB-1 (cannabinoid-1 receptor) antagonists/inverse-agonists such as limonabant (Sanofi Synthelabo), SR-147778 (Sanofi Synthelabo), BAY-65-2520 (Bayer), SLV-319 (Sorbei), as well as compounds disclosed in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, EP-658546;

4) glerin antagonists such as compounds disclosed in WO01/87355, WO02/08250;

5) histamine (H3) receptor antagonists/inverse-agonists such as thioperamide, 3-(1H-imidazol-4-yl)propyl-N-(pentenyl) carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., *Pharmazie,* 56: 927-32 (2001), benzophenone derivatives (Sasse, A. et al., *Arch. Pharm.* (Weinheim) 334: 45-52 (2001)), substituted N-phenylcarbamates (Reidemeister, S. et al., *Pharmazie,* 55: 83-6 (2000)), proxyfen derivatives (Sasse, A. et al., *J. Med. Chem.,* 43: 3335-43 (2000));

6) MCH-1R (melamine concentration hormone receptor 1) antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027, JP-A 2001-226269;

7) MCH-2R (melamine concentration hormone receptor 2) agonists/antagonists;

8) NPY1 (neuropeptide Y Y1) antagonists such as BIBP3226, J-115814, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173, WO01/89528;

9) NPY5 (neuropeptide Y Y5) antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 340, 683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., *J. Med. Chem.,* 43:4288-4312 (2000);

10) reptins such as human recombinant reptin (PEG-OB, Hoffman La Roche), recombinant methionylreptin (Amgen);

11) reptin derivatives such as compounds disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, WO96/23518, WO96/23519, WO96/23520;

12) opioid antagonists such as narmefen (Revex®), 3-methoxynartorexon, naloxone, nartolexon, compounds disclosed in WO00/21509;

13) aurexin antagonists such as SB-334867A, and other compounds disclosed in WO01/96302, WO01/68609, WO02/51232, WO02/51838, WO03/023561;

14) BRS3 (bonbesin receptor subtype-3) agonists;

15) CCK-A (cholecystokinin A) agonists such as AR-R15849, GI-181771, JMV-180, A-71378, A-71623, SR-146131, and other compounds disclosed in U.S. Pat. No. 5,739,106;

16) CNTF (ciliary neurotrophic factors) such as GI-181771 (Glaxo-Smith Kline), SR146131 (Sanofi Synthelabo), butabindide, PD170,292, PD149164 (Pfizer);

17) CNTF derivatives such as axokine (Regeneron), and other compounds disclosed in WO94/09134, WO98/22128, WO99/43813;

18) GHS (growth hormone secretion receptor) agonists such as $NN_7O_3$, hexarelin, MK-0677, SM-130686, CP424,391, L-692,429, L-163,255, and compounds disclosed in U.S. Pat. No. 6,358,951, US Patent Application Nos. 2002/049196, 2002/022637, WO01/56592, WO02/32888;

19) 5HT2c (serotonin receptor-2c) agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456, WO02/40457;

20) Mc3r (melanocortin-3 receptor) agonists;

21) Mc4r (melanocortin-4 receptor) agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847;

22) monoamine re-uptake inhibitors such as sibutramine (Meridia®/Reductil®) and its salts, and other derivatives disclosed in U.S. Pat. No. 4,746,680, U.S. Pat. No. 4,806,570, U.S. Pat. No. 5,436,272, US Patent Application No. 2002/0006964, WO01/27068, WO01/62341;

23) serotonin re-uptake inhibitors such as dexfenfluramine, fluoxetine, and other compounds disclosed in U.S. Pat. No. 6,365,633, WO01/27060, WO01/162341;

24) GLP1 (glucagon-like peptide-1) agonists;

25) Topiramate (Topimax®);

26) phytopharm compound 57 (e.g., CP644,673);

27) ACC2 (acetyl CoA carboxylase-2) inhibitors;

28) β3 (adrenalin receptor-3) agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, Trecadrine, Zeneca D7114, SR59119A, and other compounds disclosed in U.S. Pat. No. 5,705,515, U.S. Pat. No. 5,451,677, WO01/74782, WO02/32897;

29) DGAT1 (diacylglycerol acyltransferase-1) inhibitors;

30) DGAT2 (diacylglycerol acyltransferase-2) inhibitors,

31) FAS (fatty acid synthesis) inhibitors such as Cerulenin, C75;

32) PDE (phosphodiesterase) inhibitors such as theophylliine, pentoxifylline zaprinast, sildenafil, amrinone, milrinone, cilostamide, rolipram, cilomilast;

33) thyroid hormone-β agonists such as KB-2611 (KaroBio BMS), and other compounds disclosed in WO02/15845, JP-A 2000-256190;

34) UCP (uncoupling protein)-1, 2, or 3 activators such as such as phytanic acid, 4-[(E)-2-(5,6,7,8-tetrahydro-5,5,8,8-tetramethyl-2-naphthalenyl)-1-propenyl]benzoic acid (TT-NPB), retinoic acid, and other compounds disclosed in WO99/00123;

35) acylestrogens such as oleoylestrone (disclosed in del Mar-Grasa, M. et al., *Obesity Research*, 9:202-9 (2001)), 36) glucocorticoid antagonists;

37) 11β HSD1 (11-β-hydroxysteroid dehydrogenase-1) inhibitors such as BVT3498, BVT2733, and other compounds disclosed in WO01/90091, WO01/90090, WO01/90092;

38) SCD1 (stearoyl-CoA desaturase-1) inhibitors;

39) DPIV (dipeptidyl peptidase-IV) inhibitors such as isoleucine thiazolidide, valine pyrrolidide, NVP-DPP728, AF237, P93/01, TSL225, TMC-2A/2B/2C, FE999011, P9310/K364, VIP0177, SDZ274444, and other compounds disclosed in WO03/004498, WO03/004496, EP1258476, WO02/083128, WO02/062764, WO03/000250, WO03/002530, WO03/002531, WO03/002553, WO03/002593, WO03/000180, WO03/000181;

40) lipase inhibitors such as tetrahydroliptatin (Orlistat/Xenical®), Triton WR1339, RHC80267, lipstatin, teasaponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438, U.S. Pat. No. 4,242,453;

41) fatty acid transporter inhibitors;

42) dicarboxylate transporter inhibitors;

43) glucose transporter inhibitors;

44) phosphate transporter inhibitors;

45) melanocortin agonists such as melanotan II, and other compounds disclosed in WO99/64002 and WO00/746799;

46) melanin concentration hormone antagonists;

47) galanin antagonists;

48) CCK antagonists;

49) corticotropin release hormones;

50) PDE3 (phosphodiesterase 3B) agonists.

The compounds of the invention may be combined with one or more of the above-mentioned co-medicines. The combination of the compound of the invention with one or more co-medicines selected from a group consisting of medicines for diabetes and medicines for hyperlipemia is useful for prevention or remedy of metabolic disorders. In particular, a combination of the compound of the invention with a medicine for hypertension and a medicine for obesity along with a medicine for diabetes or a medicine for hyperlipemia is useful for prevention or remedy of metabolic disorders owing to the synergistic effect thereof.

When the compounds of the invention are used in clinical sites, then the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions.

Ordinary physicians, veterinarians and clinicians may readily determine the effective dose necessary for retarding, inhibiting or stopping the development of diseases.

EXAMPLES

The invention is described more concretely with reference to the following Examples, which, however, do not whatsoever restrict the invention.

For the thin-layer chromatography of the compounds in the Examples, used was a plate of Silicagel $60F_{245}$ (Merck); and for detection, used was a UV detector. Wakogel™ C-300 (Wako Pure Chemicals) was used for the column silica gel; and LC-SORB™ SP-B-ODS (Chemco) or YMC-GEL™ ODS-AQ 120-S50 (Yamamura Chemical Laboratories) was for the reversed-phase column silica gel. Mass spectrum was determined according to an electrospray ionization (ESI) process, using QuattroII (Micromass).

In NMR spectrometry in a heavy dimethylsulfoxide solution, dimethylsulfoxide was used for the internal standard. Using Gemini-200 (200 MHz; Varian), Gemini-300 (300 MHz; Varian), Mercury 400 (400 MHz; Varian) or Inova 400 (400 MHz; Varian), the sample was analyzed for the total δ value in ppm.

The meanings of the abbreviations in the following Examples are mentioned below.

i-Bu: isobutyl group n-Bu: n-butyl group t-Bu: t-butyl group

Me: methyl group

Et: ethyl group

Ph: phenyl group i-Pr: isopropyl group n-Pr: n-propyl group $CDCl_3$: heavy chloroform $CD_3OD$: heavy methanol DMSO-d6: heavy dimethylsulfoxide The meanings of the abbreviations in nuclear magnetic resonance spectra are mentioned below.

s: singlet d: doublet dd: double-doublet t: triplet m: multiplet br: broad q: quartet J: coupling constant Hz: hertz

Example 1

2-[4-(3-piperidin-1-ylpropoxy)-phenyl]-3aH-pyrazolo[1,5-d][1,2,4]triazine

Production of ethyl 4-(4-methoxyphenyl)-2,4-dioxobutyrate

With cooling with ice, 4.00 g (0.10 mol) of 65% oily sodium hydride was added to a DMF solution (200 ml) of 7.51 g (0.05 mol) of 4'-methoxyacetophenone and 8.77 g (0.06 mol) of diethyl oxalate, and stirred overnight at 100° C. in a nitrogen atmosphere. Aqueous 2 N hydrochloric acid solution was added to the reaction liquid, extracted with ethyl acetate, and the organic layer was washed with saturated saline water, dried and then concentrated under reduced pressure. Thus concentrated under reduced pressure, the resulting residue was purified through silica gel column chromatography (hexane/ethyl acetate=2/1) to obtain 12.52 g (yield: 100%) of ethyl 4-(4-methoxyphenyl)-2,4-dioxobutyrate as a yellow solid.

Production of ethyl 5-(4-methoxyphenyl)-2H-pyrazole-3-carboxylate 1.52 ml (31.28 mmol) of hydrazine was added to an ethanol solution (50 ml) of 7.12 g (28.44 mmol) of the obtained ethyl 4-(4-methoxyphenyl)-2,4-dioxobutyrate, and then the reaction liquid was stirred at 60° C. for 4 hours. The reaction liquid was concentrated under reduced pressure, and the resulting solid was washed with diethyl ether to obtain 6.76 g (yield: 96%) of ethyl 5-(4-methoxyphenyl)-2H-pyrazole-3-carboxylate as a white solid.

Production of [5-(4-methoxyphenyl)-2H-pyrazol-3-yl]-methanol

With cooling with ice, 890 mg (18.8 mmol) of lithium aluminium hydride was added to a tetrahydrofuran solution (30 ml) of 2.31 g (9.4 mmol) of the obtained ethyl 5-(4-methoxyphenyl)-2H-pyrazole-3-carboxylate, and the reaction liquid was stirred for 1 hour with cooling with ice. Aqueous 2 N sodium hydroxide solution was added to the reaction liquid, extracted with ethyl acetate, and the organic layer was washed with saturated saline water. This was dried with anhydrous sodium sulfate, and concentrated under reduced pressure to obtain 1.67 g (yield: 87%) of [5-(4-methoxyphenyl)-2H-pyrazol-3-yl]-methanol as a white solid.

Production of 5-(4-methoxyphenyl)-2H-pyrazole-3-carbaldehyde 4.06 g (41.0 mmol) of manganese dioxide was added to a chloroform solution (30 ml) of 1.67 g (8.20 mmol) of the obtained [5-(4-methoxyphenyl)-2H-pyrazol-3-yl]-methanol, and stirred at 80° C. for 8 hours. The reaction liquid was filtered through Celite, and concentrated under reduced pressure to obtain 762 mg (yield: 44%) of 5-(4-methoxyphenyl)-2H-pyrazole-3-carbaldehyde as a white solid.

Production of 2-(4-methoxyphenyl)-pyrazole[1,5-d][1,2,4]triazine 66 mg (1.10 mmol) of formohydrazide and 151 mg (1.10 mmol) of triethylamine hydrochloride were added to a xylene solution (5 ml) of 202 mg (1.00 mmol) of the obtained 5-(4-methoxyphenyl)-2H-pyrazole-3-carbaldehyde, and stirred under reflux for 2 hours. Water was added to the reaction liquid, extracted with ethyl acetate, and the organic layer was washed with saturated saline water. This was dried with anhydrous sodium sulfate, and concentrated under reduced pressure to obtain 200 mg of a crude product of 2-(4-methoxyphenyl)-pyrazole[1,5-d][1,2,4]triazine.

Production of 4-pyrazolo[1,5-d][1,2,4]triazin-2-yl-phenol 4 ml of a dichloromethane solution of 1 M boron tribromide (4.00 mol) was added to a chloroform solution (4 ml) of 200 mg of the obtained 2-(4-methoxyphenyl)-pyrazole[1,5-d][1,2,4]triazine, and stirred overnight at room temperature. Water was added to the reaction liquid, extracted with chloroform, and the organic layer was washed with saturated saline water. This was dried with anhydrous sodium sulfate, and concentrated under reduced pressure to obtain 124 mg of a crude product of 4-pyrazolo[1,5-d][1,2,4]triazin-2-yl-phenol.

Production of the Entitled Compound 1-3-(Chlorophenyl)-piperidine hydrochloride and 53 mg (0.28 mmol) of potassium carbonate were added to 53 mg (0.25 mmol) of the obtained 4-pyrazolo[1,5-d][1,2,4]triazin-2-yl-phenol, and stirred at 80° C. for 2 hours.

The reaction liquid was concentrated under reduced pressure, and the resulting residue was purified through silica gel column chromatography (chloroform/methanol=10/1) to obtain 12 mg (yield: 14%) of the entitled compound as a white solid.

$^1$HNMR (CDCl$_3$) δ: 1.50 (m, 4H), 1.62 (m, 6H), 2.10 (m, 2H), 2.50 (m, 4H), 6.95 (m, 1H), 7.00 (dd, 2H, J=2.8, 8.8 Hz), 7.89 (dd, 2H, J=2.8 Hz, 8.8 Hz), 9.29 (d, 1H, J=5.6 Hz), 9.43 (s, 1H)

ESI-MS (m/e): 338[+H]$^+$

Example 2

2-[4-(1-Cyclopentyl-piperidin-4-4]oxy)phenyl]-3aH-pyrazolo[1,5-d][1,2,4]triazine trifluoroacetate

Production of 2-[4-(piperidin-4-yloxy)phenyl]-3aH-pyrazolo[1,5-d][1,2,4]triazine hydrochloride In the same manner as in Example 1 or according to a method similar to it or according to a combination of the method with an ordinary method, but using 4-pyrazolo[1,5-d][1,2,4]triazin-2-yl-phenol obtained in Example 1 and 1-tert-butoxycarbonyl-4-chloro-piperidine obtained in Reference Example 1, 2-[4-(1-tert-butoxycarbonyl-4-yloxy)phenyl]-3aH-pyrazolo-[1,5-d][1,2,4]triazine was obtained. Next, the Boc group of 2-[4-(1-tert-butoxycarbonyl-4-yloxy)phenyl]-3aH-pyrazolo-1,5-d][1,2,4]triazine was removed according to a method described in literature (for example, *Protective Groups in Organic Synthesis*) or a method similar to it to obtain 2-[4-(piperidin-4-yloxy)phenyl]-3aH-pyrazolo[1,5-d][1,2,4]triazine hydrochloride.

Production of the Entitled Compound

20 μl (0.24 mmol) of cyclopentanone, 16 mg (0.12 mmol) of zinc chloride and 20 mg (0.3 mmol) of sodium borocyanide were added to a methanol solution (5 ml) of 66 mg (0.2 mmol) of 2-[4-(1-cyclopentyl-piperidin-4-yloxy)phenyl]-3aH-pyrazolo[1,5-d][1,2,4]triazine hydrochloride, and stirred overnight at room temperature. The reaction mixture was concentrated under reduced pressure, and the residue was extracted with chloroform. The organic layer was washed with saturated saline water, dried with anhydrous sodium sulfate, and concentrated under reduced pressure, and the resulting residue was purified through reversed-phase HPLC (acetonitrile/$H_2O$=10% to 95%, gradient) to obtain the entitled compound (4 mg, 4%).

$^1$HNMR (CDCl$_3$) δ: 1.23 (m, 2H), 1.60 (br, 5H), 2.10 (m, 6H), 2.50 (m, 2H), 2.85 (br, 2H), 4.47 (m, 1H), 6.95 (m, 1H), 7.02 (dd, 2H, J=2.7, 8.6 Hz), 7.92 (dd, 2H, J=2.7 Hz, 8.6 Hz), 9.27 (d, 1H, J=5.6 Hz), 9.42 (s, 1H)

ESI-MS (m/e): 364 [M+H]$^+$

Example 3

3-Methyl-2-[4-(3-piperidin-1-ylpropoxy)-phenyl]-3aH-pyrazolo[1,5-d][1,2,4]triazine The compound of Example 3 can be produced in the same manner as in Example 1 or according to a method similar to it or according to a combination of the method with an ordinary method, but using 4'-methoxypropiophenone in place of 4'-methoxyacetophenone.

$^1$HNMR (CDCl$_3$) δ: 1.62 (br, 6H), 2.0 (m, 2H), 2.42 (m, 4H), 2.45 (m, 2H), 2.53 (s, 3H), 4.09 (m, 2H), 7.03 (d, 2H, J=9.2 Hz), 7.74 (d, 2H, J=8.8 Hz), 9.24 (d, 1H, J=2.0 Hz), 9.37 (d, 1H, J=2.4 Hz)

ESI-MS (m/e): 352 [M+H]$^+$

Example 4

3-Ethyl-2-[4-(3-piperidin-1-ylpropoxy)-phenyl]-3aH-pyrazolo[1,5-d][1,2,4]triazine The compound of Example 4 was obtained as a colorless oily substance in the same manner as in Example 1 or according to a method similar to it or according to a combination of the method with an ordinary method, but using 4'-methoxybutyrophenone in place of 4'-methoxyacetophenone.

$^1$HNMR (CDCl$_3$) δ: 1.34 (t, 3H, J=7.6 Hz), 1.40 (m, 2H), 1.62 (br, 4H), 2.00 (m, 2H), 2.40 (m, 6H), 2.98 (m, 2H), 4.05 (m, 2H), 7.08 (dd, 2H, J=2.8, 8.4 Hz), 7.67 (dd, 2H, J=2.8, 8.4 Hz), 9.27 (d, 1H, J=2.4 Hz), 9.37 (d, 1H, J=2.4 Hz)

ESI-MS (m/e): 366 [M+H]$^+$

Example 5

7-Methyl-2-[4-(3-piperidin-1-ylpropoxy)-phenyl-3aH-pyrazolo[1,5-d][1,2,4]triazine The compound of Example 5 can be produced in the same manner as in Example 1 or according to a method similar to it or according to a combination of the method with an ordinary method, but using 5-(4-methoxyphenyl)-2H-pyrazole-3-carbaldehyde obtained in Example 1 and acetohydrazide in place of formylhydrazide.

$^1$HNMR (CDCl$_3$) δ: 1.61 (br, 6H), 2.03 (m, 2H), 2.41 (m, 4H), 2.49 (t, 2H, J=7.6 Hz), 3.04 (s, 3H), 4.05 (m, 2H), 6.99 (s, 1H), 7.00 (dd, 2H, J=2.0, 6.8 Hz), 7.92 (dd, 2H, J=2.0, 6.8 Hz), 9.23 (s, 1H)

ESI-MS (m/e): 352 [M+H]$^+$

Example 6

7-(5-Methyl-isoxazol-3-yl)-2-[4-(3-piperidin-1-ylpropoxy)-phenyl]-3aH-pyrazolo[1,5-d][1,2,4]triazine The compound of Example 6 was obtained as a white solid in the same manner as in Example 1 or according to a method similar to it or according to a combination of the method with an ordinary method, but using 5-(4-methoxyphenyl)-2H-pyrazole-3-carbaldehyde obtained in Example 1 and 5-methylisoxazole-3-carbohydrazide in place of formylhydrazide.

$^1$HNMR (CDCl$_3$) δ: 1.60 (br, 6H), 2.05 (m, 2H), 2.50 (m, 6H), 2.63 (s, 3H), 4.08 (t, 2H, J=6.4 Hz), 7.00 (d, 2H, J=8.8 Hz), 7.10 (s, 2H), 7.96 (dd, 2H, J=2.4, 7.2 Hz), 9.35 (s, 1H)

ESI-MS (m/e): 419 [M+H]$^+$

Example 7

7-Phenyl-2-[4-(3-piperidin-1-ylpropoxy)-phenyl]-3aH-pyrazolo[1,5-d][1,2,4]triazine The compound of Example 7 was obtained as white solid in the same manner as in Example 1 or according to a method similar to it or according to a combination of the method with an ordinary method, but using 5-(4-methoxyphenyl)-2H-pyrazole-3-carbaldehyde obtained in Example 1 and benzohydrazide in place of formylhydrazide.

$^1$HNMR (CDCl$_3$) δ: 1.50 (br, 2H), 1.65 (br, 4H), 2.05 (m, 2H), 2.50 (m, 6H), 4.08 (t, 2H, J=6.4 Hz), 6.99 (d, 2H, J=8.8 Hz), 7.06 (s, 1H), 7.62 (m, 3H), 7.93 (d, 2H, J=8.4 Hz), 8.61 (dd, 2H, J=1.2, 7.6 Hz), 9.28 (s, 1H)

ESI-MS (m/e): 414 [M+H]$^+$

Example 8

3-Methyl-7-phenyl-2-[4-(3-piperidin-1-ylpropoxy)-phenyl]-3aH-pyrazolo[1,5-d][1,2,4]triazine The compound of Example 8 was obtained as white solid in the same manner as in Example 1 or according to a method similar to it or according to a combination of the method with an ordinary method, but using 4'-methoxypropiophenone in place of 4'-methoxyacetophenone and benzohydrazide in place of formylhydrazide.

$^1$HNMR (CDCl$_3$) δ: 1.50 (m, 2H), 1.60 (br, 4H), 2.05 (m, 2H), 2.50 (m, 6H), 2.52 (s, 3H), 4.08 (t, 2H, J=6.4 Hz), 7.00 (d, 2H, J=8.8 Hz), 7.04 (s, 1H), 7.60 (m, 3H), 7.96 (d, 2H, J=8.8 Hz), 8.60 (d, 2H, J=7.6 Hz)

ESI-MS (m/e): 428 [M+H]$^+$

Example 9

3-Methyl-2-[4-(3-piperidin-1-ylpropoxy)-phenyl]-7-(pyridin-3-yl)-3aH-pyrazolo[1,5-d][1,2,4]triazine The compound of Example 9 was obtained as white solid in the same manner as in Example 1 or according to a method similar to it or according to a combination of the method with an ordinary method, but using 4'-methoxypropiophenone in place of 4'-methoxyacetophenone and nicotinylhydrazide in place of formylhydrazide.

$^1$HNMR (CDCl$_3$) δ: 1.60 (br, 6H), 2.02 (m, 2H), 2.42 (m, 6H), 2.58 (s, 3H), 4.08 (t, 2H, J=6.4 Hz), 7.02 (d, 2H, J=2.4 Hz), 7.52 (m, 1H), 7.79 (d, 2H, J=2.4 Hz), 8.81 (m, 1H), 8.94 (m, 1H), 9.25 (s, 1H), 9.89 (s, 1H)

ESI-MS (m/e): 429 [M+H]$^+$

Example 10

6-[4-(3-piperidin-1-ylpropoxy)phenyl]-[1,2,4]triazolo[4,3-b]pyridazine

Production of ethyl 2-hydroxy-4-(4-methoxyphenyl)-4-oxo-butyrate 15.02 g (0.10 mol) of 4'-methoxyacetophenone and a 45% toluene solution (25 ml) of ethyl glyoxalate were stirred overnight at 100° C. The reaction liquid was concentrated under reduced pressure, and the resulting residue was purified through silica gel column chromatography (hexane/ethyl acetate=2/1) to obtain 20.62 g (yield: 82%) of ethyl 2-hydroxy-4-(4-methoxyphenyl)-4-oxo-butyrate as a yellow oily substance.

Production of 6-(4-methoxyphenyl)-pyridazin-3-ol 4.91 ml (98.0 mmol) of hydrazine was added to an ethanol solution (50 ml) of 20.62 g (82.0 mmol) of the obtained ethyl 2-hydroxy-4-(4-methoxyphenyl)-4-oxo-butyrate, and the reaction liquid was stirred at 60° C. for 4 hours. The reaction liquid was concentrated under reduced pressure, and the resulting solid was washed with diethyl ether to obtain 16.18 g (yield: 80%) of 6-(4-methoxyphenyl)-pyridazin-3-ol as a white solid.

Production of 3-chloro-6-(4-methoxyphenyl)-pyridazine

With cooling with ice, 50 ml of phosphorus oxychloride was added to 10.00 g (49.5 mmol) of the obtained 6-(4-methoxyphenyl)-pyridazin-3-ol, and the reaction liquid was stirred under reflux for 6 hours. Water was added to the reaction liquid, extracted with chloroform, and the organic layer was washed with saturated saline water. This was dried with anhydrous sodium sulfate, and concentrated under reduced pressure to obtain 4.41 g (yield: 40%) of 3-chloro-6-(4-methoxyphenyl)-pyridazine as a white solid.

Production of 6-(4-methoxyphenyl)-[1,2,4]triazole[4,3-b]pyridazine 1.80 g (30.0 mmol) of formohydrazine and 4.13 g (30.0 mmol) of triethylamine hydrochloride were added to a xylene solution (5 ml) of 4.41 g (20.0 mmol) of the obtained 3-chloro-6-(4-methoxyphenyl)-pyridazine, and stirred under reflux for 2 hours. Water was added to the reaction liquid, extracted with ethyl acetate, and the organic layer was washed with saturated saline water. This was dried with anhydrous sodium sulfate, concentrated under reduced pressure, and the resulting residue was purified through silica gel column chromatography (hexane/ethyl acetate=1/2) to obtain 1.23 g (yield: 27%) of 6-(4-methoxyphenyl)-[1,2,4]triazole[4,3-b]pyridazine.

Production of 4-[1,2,4]triazolo[4,3-b]pyridazin-6-yl-phenol 1.5 ml of a dichloromethane solution of 1 M boron tribromide (1.50 mol) was added to a chloroform solution (4 ml) of 107 mg (0.47 mmol) of the obtained 6-(4-methoxyphenyl)-[1,2,4]triazole[4,3-b]pyridazine, and stirred overnight at room temperature. Water was added to the reaction liquid, extracted with chloroform, and the organic layer was washed with saturated saline water. This was dried with anhydrous sodium sulfate, and concentrated under reduced pressure to obtain 90 mg of a crude product of 4-[1,2,4]triazolo[4,3-b]pyridazin-6-yl-phenol.

Production of the Entitled Compound 95 mg (0.48 mmol) of 1-(3-chloropropyl)-piperidine hydrochloride and 66 mg (0.48 mmol) of potassium carbonate were added to 34 mg (0.16 mmol) of the obtained 4-[1,2,4]triazolo[4,3-b]pyridazin-6-yl-phenol, and stirred at 80° C. for 2 hours.

The reaction liquid was concentrated under reduced pressure, and the resulting residue was purified through silica gel column chromatography (chloroform/methanol=10/1) to obtain 6 mg (yield: 10%) of the entitled compound as a white solid.

$^1$HNMR (CDCl$_3$) δ: 1.60 (br, 6H), 2.00 (m, 2H), 2.42 (m, 6H), 4.10 (t, 2H, J=6.0 Hz), 7.05 (d, 2H, J=8.8 Hz), 7.56 (d, 1H, J=9.6 Hz), 7.92 (d, 2H, J=9.2 Hz), 8.14 (d, 1H, J=9.2 Hz), 9.11 (s, 1H)

ESI-MS (m/e): 338 [M+H]$^+$

Example 11

7-Methyl-6-[4-(3-piperidin-1-ylpropoxy)-phenyl]-[1,2,4]triazolo[4,3-b]pyridazine The compound of Example 11 was obtained as a white solid in the same manner as in Example 10 or according to a method similar to it or according to a combination of the method with an ordinary method, but using 4'-methoxypropiophenone in place of 4'-methoxyacetophenone.

$^1$HNMR (CDCl$_3$) δ: 1.58 (br, 8H), 2.07 (br, 2H), 2.39 (s, 3H), 2.50 (m, 4H), 4.10 (t, 2H, J=6.4 Hz), 7.04 (d, 2H, J=8.4 Hz), 7.45 (d, 2H, J=8.4 Hz), 7.93 (s, 1H), 9.04 (s, 1H)

ESI-MS (m/e): 352 [M+H]$^+$

Example 12

3-Methyl-6-[4-(3-piperidin-1-ylpropoxy)-phenyl]-[1,2,4]triazolo[4,3-b]pyridazine The compound of Example 12 was obtained as a white solid in the same manner as in Example 10 or according to a method similar to it or according to a combination of the method with an ordinary method, but using 3-chloro-6-(4-methoxyphenyl)-pyridazine obtained in Example 10 and acetohydrazide in place of formylhydrazide.

$^1$HNMR (CDCl$_3$) δ: 1.60 (br, 8H), 2.10 (m, 2H), 2.50 (m, 4H), 2.86 (s, 3H), 4.10 (t, 2H, J=6.4 Hz), 7.03 (d, 2H, J=9.6 Hz), 7.49 (d, 1H, J=9.6 Hz), 7.93 (d, 2H, J=8.4 Hz), 8.05 (d, 1H, J=10.0 Hz)

ESI-MS (m/e): 352 [M+H]$^+$

Example 13

6-[4-(3-Piperidin-1-ylpropoxy)-phenyl]-3-trifluoromethyl-[1,2,4]triazolo[4,3-b]pyridazine The compound of Example 13 was obtained as a white solid in the same manner as in Example 10 or according to a method similar to it or according to a combination of the method with an ordinary method, but using 3-chloro-6-(4-methoxyphenyl)-pyridazine obtained in Example 10 and trifluoroacetohydrazide in place of formylhydrazide.

$^1$HNMR (CDCl$_3$) δ: 1.60 (br, 8H), 2.05 (m, 2H), 2.40 (m, 4H), 4.10 (t, 2H, J=6.4 Hz), 7.04 (d, 2H, J=8.8 Hz), 7.71 (d, 1H, J=9.6 Hz), 7.95 (d, 2H, J=8.0 Hz), 8.20 (d, 1H, J=10.0 Hz)

ESI-MS (m/e): 406 [M+H]$^+$

Example 14

3-Tert-butyl-6-[4-(3-piperidin-1-ylpropoxy)-phenyl]-[1,2,4]triazolo[4,3-b]pyridazine The compound of Example 14 was obtained as a colorless oily substance in the same manner as in Example 10 or according to a method similar to it or according to a combination of the method with an ordinary method, but using 3-chloro-6-(4-methoxyphenyl)-pyridazine obtained in Example 10 and pivalohydrazide in place of formylhydrazide.

$^1$HNMR (CDCl$_3$) δ: 1.60 (br, 8H), 1.68 (s, 9H), 2.10 (m, 2H), 2.50 (m, 4H), 4.10 (t, 2H, J=6.0 Hz), 7.03 (d, 2H, J=8.8 Hz), 7.47 (d, 1H, J=9.6 Hz), 7.90 (d, 2H, J=9.2 Hz), 8.07 (d, 1H, J=9.6 Hz)

ESI-MS (m/e): 394 [M+H]$^+$

Example 15

3-Phenyl-6-[4-(3-piperidin-1-ylpropoxy)-phenyl]-[1,2,4]triazolo[4,3-b]pyridazine The compound of Example 15 was obtained as a white solid in the same manner as in Example 10 or according to a method similar to it or according to a combination of the method with an ordinary method, but using 3-chloro-6-(4-methoxyphenyl)-pyridazine obtained in Example 10 and benzohydrazide in place of formylhydrazide.

$^1$HNMR (CDCl$_3$) δ: 1.60 (br, 8H), 2.03 (m, 2H), 2.45 (m, 4H), 4.11 (t, 2H, J=6.4 Hz), 7.07 (d, 2H, J=8.8 Hz), 7.57 (m, 4H), 7.97 (d, 2H, J=8.8 Hz), 8.19 (d, 1H, J=10.0 Hz), 8.88 (d, 2H, J=7.2 Hz)

ESI-MS (m/e): 414 [M+H]$^+$

Example 16

6-[4-(3-Piperidin-1-ylpropoxy)-phenyl]-3-(pyridin-2-yl)-[1,2,4]triazolo[4,3-b]pyridazine The compound of Example 16 was obtained as a yellow solid in the same manner as in Example 10 or according to a method similar to it or according to a combination of the method with an ordinary method, but using 3-chloro-6-(4-methoxyphenyl)-pyridazine obtained in Example 10 and 2-picolinohydrazide in place of formylhydrazide.

$^1$HNMR (CDCl$_3$) δ: 1.60 (br, 8H), 2.05 (m, 2H), 2.45 (m, 4H), 4.10 (t, 2H, J=6.8 Hz), 7.05 (d, 2H, J=8.8 Hz), 7.45 (m, 1H), 7.61 (d, 1H, J=10.0 Hz), 7.91 (d, 1H, J=7.6 Hz), 7.98 (d, 2H, J=8.8 Hz), 8.21 (d, 1H, J=10.0 Hz), 8.51 (d, 1H, J=6.4 Hz), 8.89 (dd, 1H, J=1.6, 4.4 Hz)

ESI-MS (m/e): 415 [M+H]$^+$

Example 17

6-[4-(3-Piperidin-1-ylpropoxy)-phenyl]-3-(pyridin-3-yl)-[1,2,4]triazolo[4,3-b]pyridazine The compound of Example 17 was obtained as a white solid in the same manner as in Example 10 or according to a method similar to it or according to a combination of the method with an ordinary method, but using 3-chloro-6-(4-methoxyphenyl)-pyridazine obtained in Example 10 and nicotinohydrazide in place of formylhydrazide.

$^1$HNMR (CDCl$_3$) δ: 1.60 (br, 8H), 2.05 (m, 2H), 2.42 (m, 4H), 4.11 (t, 2H, J=6.4 Hz), 7.06 (d, 2H, J=10.0 Hz), 7.52 (m, 1H), 7.62 (d, 1H, J=10.0 Hz), 7.97 (d, 2H, J=10.0 Hz), 8.20 (d, 1H, J=10.0 Hz), 8.75 (dd, 1H, J=2.0, 4.8 Hz), 8.83 (d, 1H, J=8.0 Hz), 9.86 (s, 1H)

ESI-MS (m/e): 415 [M+H]$^+$

Example 18

7-Methyl-3-phenyl-6-[4-(3-piperidin-1-ylpropoxy)-phenyl]-[1,2,4]triazolo[4,3-b]pyridazine The compound of Example 18 was obtained as a yellow oily substance in the same manner as in Example 10 or according to a method similar to it or according to a combination of the method with an ordinary method, but using 4'-methoxypropiophenone in place of 4'-methoxyacetophenone and using 3-chloro-6-(4-methoxyphenyl)-pyridazine obtained in Example 10 and benzohydrazide in place of formylhydrazide.

$^1$HNMR (CDCl$_3$) δ: 1.60 (br, 8H), 2.05 (m, 2H), 2.42 (s, 3H), 2.50 (m, 4H), 4.11 (t, 2H, J=6.0 Hz), 7.06 (d, 2H, J=8.8 Hz), 7.48 (m, 5H), 7.98 (s, 1H), 8.53 (d, 2H, J=8.4 Hz)

ESI-MS (m/e): 428 [M+H]$^+$

Example 19

6-Methyl-7-[4-(3-Piperidin-1-ylpropoxy)-phenyl]-[1,2,4]triazolo[4,3-b]pyridazine Production of 5-hydroxy-4-(4-methoxyphenyl)-5-methyl-5H-furan-2-one 16.42 g (0.10 mol) of 4-methoxyphenylacetone and an aqueous solution of 45% glyoxylic acid (19.4 ml, 0.11 mol) were stirred overnight at 100° C. The reaction liquid was concentrated under reduced pressure to obtain a crude product of 5-hydroxy-4-(4-methoxyphenyl)-5-methyl-5H-furan-2-one.

Production of 5-(4-methoxyphenyl)-6-methyl-pyridazin-3-ol 5.27 ml (105.0 mmol) of hydrazine was added to an ethanol solution (50 ml) of the obtained crude product of 5-hydroxy-4-(4-methoxyphenyl)-5-methyl-5H-furan-2-one, and the reaction liquid was stirred at 60° C. for 4 hours. The reaction liquid was concentrated under reduced pressure, and the resulting solid was washed with diethyl ether to obtain 9.66 g (yield: 45%) of 5-(4-methoxyphenyl)-6-methyl-pyridazin-3-ol as a white solid.

Production of 6-chloro-4-(4-methoxyphenyl)-3-methyl-pyridazine

With cooling with ice, 30 ml of phosphorus oxychloride was added to 5.92 g (27.4 mmol) of the obtained pyridazine compound, and the reaction liquid was stirred under reflux for 6 hours. Water was added to the reaction liquid, extracted with chloroform, and the organic layer was washed with saturated saline water. This was dried with anhydrous sodium sulfate, and concentrated under reduced pressure to obtain 3.91 g (yield: 61%) of 6-chloro-4-(4-methoxyphenyl)-3-methyl-pyridazine as a whites solid.

Production of 7-(4-methoxyphenyl)-6-methyl-[1,2,4]triazolo[4,3-b]pyridazine 135 mg (2.25 mmol) of formohydrazide and 310 mg (2.25 mmol) of triethylamine hydrochloride were added to a xylene solution (5 ml) of 352 mg (1.5 mmol) of the obtained 6-chloro-4-(4-methoxyphenyl)-3-methyl-pyridazine, and stirred under reflux for 2 hours. Water was added to the reaction liquid, extracted with ethyl acetate, and the organic layer was washed with saturated saline water. This was dried with anhydrous sodium sulfate, concentrated under reduced pressure, and the resulting residue was purified through silica gel column chromatography (hexane/ethyl acetate=1/2) to obtain 75 mg (yield: 21%) of 7-(4-methoxyphenyl)-6-methyl-[1,2,4]triazolo[4,3-b]pyridazine.

Production of 4-(6-methyl-[1,2,4]triazolo[4,3-b]pyridazin-7-yl)-phenol 1.5 ml (1.41 mol) of a dichloromethane solution of 1 M boron tribromide was added to a chloroform solution (4 ml) of 107 mg (0.47 mmol) of the obtained 7-(4-methoxyphenyl)-6-methyl-[1,2,4]triazolo[4,3-b]pyridazine, and stirred overnight at room temperature. Water was added to the reaction liquid, extracted with chloroform, and the organic layer was washed with saturated saline water. This was dried with anhydrous sodium sulfate, and concentrated under reduced pressure to obtain 68 mg of a crude product of 4-(6-methyl-[1,2,4]triazolo[4,3-b]pyridazin-7-yl)-phenol.

Production of Entitled Compound 89 mg (0.45 mmol) of 1-(3-chlorophenyl)-piperidine hydrochloride and 124 mg (0.90 mmol) of potassium carbonate were added to 68 mg (0.3 mmol) of the obtained 4-(6-methyl-[1,2,4]triazolo[4,3-b]pyridazin-7-yl)-phenol, and stirred at 80° C. for 2 hours.

The reaction liquid was concentrated under reduced pressure, and the resulting residue was purified through silica gel column chromatography (chloroform/methanol=10/1) to obtain 79 mg (yield: 75%) of the entitled compound as a white solid.

$^1$HNMR (CDCl$_3$) δ: 1.60 (br, 8H), 2.05 (m, 2H), 2.42 (s, 3H), 2.50 (m, 4H), 4.11 (t, 2H, J=6.0 Hz), 7.06 (d, 2H, J=8.8 Hz), 7.48 (m, 2H), 7.98 (s, 1H), 8.53 (d, 1H, J=8.4 Hz)

ESI-MS (m/e): 352 [M+H]$^+$

Example 20

3,6-Dimethyl-7-[4-(3-piperidin-1-ylpropoxy)-phenyl]-[1,2,4]triazolo[4,3-b]pyridazine The compound of Example 20 was obtained as a white solid in the same manner as in Example 19 or according to a method similar to it or according to a combination of the method with an ordinary method, but using 6-chloro-4-(4-methoxyphenyl)-3-methyl-pyridazine obtained in Example 19 and acetohydrazide in place of formylhydrazide.

$^1$HNMR (CDCl$_3$) δ: 1.60 (br, 8H), 2.05 (m, 2H), 2.45 (m, 4H), 2.48 (s, 3H), 2.82 (s, 3H), 4.07 (t, 2H, J=6.0 Hz), 6.84 (d, 2H, J=8.8 Hz), 7.26 (d, 2H, J=8.8 Hz), 7.64 (s, 1H)

ESI-MS (m/e): 366 [M+H]$^+$

Example 21

6-Methyl-3-phenyl-[4-(3-piperidin-1-ylpropoxy)-phenyl]-[1,2,4]triazolo[4,3-b]pyridazine The compound of Example 21 was obtained as a pale yellow solid in the same manner as in Example 19 or according to a method similar to it or according to a combination of the method with an ordinary method, but using 6-chloro-4-(4-methoxyphenyl)-3-methyl-pyridazine obtained in Example 19 and benzohydrazide in place of formylhydrazide.

$^1$HNMR (CDCl$_3$) δ: 1.60 (br, 8H), 2.05 (m, 2H), 2.45 (m, 4H), 2.61 (s, 3H), 4.08 (t, 2H, J=6.8 Hz), 7.02 (d, 2H, J=6.4 Hz), 7.29 (d, 2H, J=6.4 Hz), 7.50 (m, 3H), 7.89 (s, 1H), 8.52 (d, 2H, J=7.2 Hz)

ESI-MS (m/e): 428 [M+H]$^+$

Example 22

6-[4-(3-piperidin-1-ylpropoxy)-phenyl]-pyrido[3,2-d][1,2,4]triazolo[4,3-b]pyridazine Production of mixture of 8-(4-methoxyphenyl)-6H-pyrido[2,3-d]pyridazin-5-one and 5-(4-methoxyphenyl)-7H-pyrido[2,3-d]pyridazin-8-one 0.45 mg (8.9 mmol) of hydrazine was added to an ethanol solution (20 ml) of 1.91 g (7.4 mmol) of a mixture of 2-(4-methoxybenzoyl)-nicotinic acid and 3-(4-methoxybenzoyl)-pyridine-2-carboxylic acid, obtained according to the method described in Bioorganic & Medicinal Chemistry, Vol. 10, pp. 2461-2470 (2002), and the reaction liquid was stirred at 60° C. for 4 hours. The reaction liquid was concentrated under reduced pressure. The resulting solid was washed with diethyl ether to obtain 1.58 g (yield: 84%) of a mixture of 8-(4-methoxyphenyl)-6H-pyrido[2,3-d]pyridazin-5-one and 5-(4-methoxyphenyl)-7H-pyrido[2,3-d]pyridazin-8-one as a white solid.

Production of mixture of 5-chloro-8-(4-methoxyphenyl)-pyrido[2,3-d]pyridazine and 8-chloro-5-(4-methoxyphenyl)-pyrido[2,3-d]pyridazine With cooling with ice, 25 ml of phosphorus oxychloride was added to 5.05 g (20 mmol) of the obtained mixture of 8-(4-methoxyphenyl)-6H-pyrido[2,3-d]pyridazin-5-one and 5-(4-methoxyphenyl)-7H-pyrido[2,3-d]pyridazin-8-one, and the reaction liquid was stirred under reflux for 6 hours. Water was added to the reaction liquid, extracted with chloroform, and the organic layer was washed with saturated saline water. This was dried with anhydrous sodium sulfate, and concentrated under reduced pressure to obtain 1.72 g (yield: 86%) of a mixture of 5-chloro-8-(4-methoxyphenyl)-pyrido[2,3-d]pyridazine and 8-chloro-5-(4-methoxyphenyl)-pyrido[2,3-d]pyridazine as a white solid.

Production of mixture of 6-(4-methoxyphenyl-pyrido[3,2-d][1,2,4]triazolo[4,3-b]pyridazine and 6-(4-methoxyphenyl)-pyrido[2,3-d[1,2,4]triazolo[4,3-b]pyridazine 91 mg (1.5 mmol) of formohydrazide and 206 mg (1.5 mmol) of triethylamine hydrochloride were added to a xylene solution (5 ml) of 272 mg (1.0 mmol) of the obtained mixture of 5-chloro-8-(4-methoxyphenyl)-pyrido[2,3-d]pyridazine and 8-chloro-5-(4-methoxyphenyl)-pyrido[2,3-d]pyridazine, and stirred under reflux for 2 hours. Water was added to the reaction mixture, extracted with ethyl acetate, and the organic layer was washed with saturated saline water. This was dried with anhydrous sodium sulfate, and concentrated under reduced pressure to obtain a mixture of 6-(4-methoxyphenyl)-pyrido[3,2-d][1,2,4]triazolo[4,3-b]pyridazine and 6-(4-methoxyphenyl)-pyrido[2,3-d][1,2,4]triazolo[4,3-b]pyridazine.

Production of 4-(pyrido[3,2-d][1,2,4]triazolo[4,3-b] pyridazin-6-yl)-phenol and 4-(pyrido[2,3-d][1,2,4] triazolo[4,3-b]pyridazin-6-yl)-phenol 1.5 ml (1.5 mmol) of a dichloromethane solution of 1 M boron trifluoride was added to a chloroform solution (4 ml) of the obtained mixture of 6-(4-methoxyphenyl)-pyrido[3,2-d][1,2,4]triazolo[4,3-b]pyridazine and 6-(4-methoxyphenyl)-pyrido[2,3-d][1,2,4]triazolo[4,3-b]pyridazine, and stirred overnight at room temperature. Water was added to the reaction liquid, extracted with chloroform, and the organic layer was washed with saturated saline water. This was dried with anhydrous sodium sulfate, and concentrated under reduced pressure to obtain 101 mg of a crude product of 4-(pyrido[3,2-d][1,2,4]triazolo[4,3-b]pyridazin-6-yl)-phenol and 4-(pyrido[2,3-d][1,2,4]triazolo[4,3-b]pyridazin-6-yl)-phenol.

Production of the Entitled Compound 115 mg (0.58 mmol) of 1-(3-chlorophenyl)-piperidine hydrochloride and 158 mg (1.14 mmol) of potassium carbonate were added to 101 mg (0.38 mmol) of the obtained crude product of 4-(pyrido[3,2-d][1,2,4]triazolo[4,3-b]pyridazin-6-yl)-phenol and 4-(pyrido[2,3-d][1,2,4]triazolo[4,3-b]pyridazin-6-yl)-phenol, and stirred at 80° C. for 2 hours.

The reaction liquid was concentrated under reduced pressure, and the resulting residue was purified through silica gel column chromatography (chloroform/methanol=10/1) to obtain 5 mg (yield: 34%) of the entitled compound as a white solid.

$^1$HNMR (CDCl$_3$) δ: 1.60 (br, 8H), 2.10 (m, 2H), 2.50 (m, 4H), 4.12 (t, 2H, J=6.4 Hz), 7.07 (d, 2H, J=8.8 Hz), 7.82 (m, 1H), 7.99 (m, 2H), 9.04 (d, 1H, J=8.4 Hz), 9.08 (s, 1H), 9.12 (m, 1H)

ESI-MS (m/e): 389 [M+H]$^+$

Example 23

3-Phenyl-6-[4-(3-piperidin-1-ylpropoxy)-phenyl]-pyrido[2,3-d][1,2,4]triazolo[4,3-b]pyridazine The compound of Example 23 was obtained as a white solid in the same manner as in Example 22 or according to a method similar to it or according to a combination of the method with an ordinary method, but using 8-chloro-5-(4-methoxyphenyl)-pyrido[2,3-d]pyridazine obtained in Example 22 and benzohydrazide in place of formylhydrazide.

$^1$HNMR (CDCl$_3$) δ: 1.60 (br, 8H), 2.10 (m, 2H), 2.60 (m, 4H), 4.15 (t, 2H, J=6.0 Hz), 7.11 (d, 2H, J=8.8 Hz), 7.52 (m, 3H), 7.65 (m, 3H), 8.30 (d, 1H, J=6.8 Hz), 8.52 (dd, 2H, J=2.0, 6.0 Hz), 9.21 (m, 1H)

ESI-MS (m/e): 465 [M+H]$^+$

Example 24

3-Phenyl-6-[6-(3-piperidin-1-ylpropyl)-pyridin-3-ylmethoxy]-[1,2,4]triazolo[3,4-a]phthalazine Production of 6-chloro-3-phenyl-[1,2,4]triazolo[3,4-a]phthalazine 128 μl (1.1 mmol) of benzoyl chloride was added to a xylene solution (10 ml) of 194 mg (1.0 mmol) of (4-chlorophthalazin-1-yl)-hydrazine and 182 μl (1.3 mmol) of triethylamine, and stirred overnight under reflux. Aqueous saturated sodium hydrogencarbonate solution was added to the reaction liquid, and extracted with chloroform. The organic layer was washed with saturated saline solution, dried and concentrated under reduced pressure to obtain 208 mg (yield: 74%) of 6-chloro-3-phenyl-[1,2,4]triazolo[3,4-a]phthalazine as a yellow solid.

Production of the Entitled Compound 53 mg (0.24 mmol) of [6-(2-piperidin-1-yl-ethyl)-pyridin-3-yl]-methanol and 10 mg (0.20 mol) of 65% oily sodium hydride were added to a dimethylformamide (3 ml) solution of 56 mg (0.20 mmol) of the obtained 6-chloro-3-phenyl-[1,2,4]triazolo[3,4-a]phthalazine, and then stirred overnight in a nitrogen atmosphere at 80° C. Aqueous 2 N hydrochloric acid solution was added to the reaction liquid, extracted with ethyl acetate, and the organic layer was washed with saturated saline water, dried and then concentrated under reduced pressure. After thus concentrated under reduced pressure, the resulting residue was purified through silica gel column chromatography (hexane/ethyl acetate=2/1) to obtain 6 mg (yield: 65%) of the entitled compound as a yellow solid.

$^1$HNMR (CDCl$_3$) δ: 1.60 (br, 6H), 2.52 (m, 4H), 2.78 (m, 2H), 3.07 (m, 2H), 5.58 (s, 2H), 7.25 (m, 1H), 7.55 (m, 3H), 7.78 (m, 2H), 7.94 (t, 1H, J=7.6 Hz), 8.20 (d, 1H, J=8.0 Hz), 8.37 (d, 2H, J=8.4 Hz), 8.70 (m, 2H)

ESI-MS (m/e): 465 [M+H]$^+$

Example 25

3-Phenyl-6-[4-(3-piperidin-1-ylpropoxy)-phenyl]-[1,2,4]triazolo[3,4-a]phthalazine Production of 2-(4-methoxyphenyl)-benzoic acid 100 ml (0.11 mol) of a diethyl ether solution of 1 M 4-methoxyphenylmagnesium bromide was dropwise added to a tetrahydrofuran solution (200 ml) of 14.81 g (0.10 mol) of phthalic anhydride at −78° C., and stirred overnight at room temperature. Aqueous 1 N hydrochloric acid solution was added to the reaction liquid, extracted with chloroform, and the organic layer was washed with saturated saline water. This was dried with anhydrous sodium sulfate, then the reaction liquid was concentrated under reduced pressure, and the resulting residue was purified through silica gel column chromatography (hexane/ethyl acetate=1/2) to obtain 25.63 g (yield: 100%) of 2-(4-methoxyphenyl)-benzoic acid as a yellow oily substance.

Production of 4-(4-methoxyphenyl)-2H-phthalazin-1-on 4.10 ml (81.2 mmol) of hydrazine was added to an ethanol solution (100 ml) of 17.33 g (67.6 mmol) of the obtained 2-(4-methoxyphenyl)-benzoic acid, and the reaction liquid was stirred at 60° C. for 4 hours. The reaction liquid was concentrated under reduced pressure, and the resulting solid was washed with diethyl ether to obtain 9.46 g (yield: 55%) of 4-(4-methoxyphenyl)-2H-phthalazin-1-on as a white solid.

Production of 1-chloro-4-(4-methoxyphenyl)-phthalazine

With cooling with ice, 25 ml of phosphorus oxychloride was added to 95.05 g (20 mmol) of the obtained 4-(4-methoxyphenyl)-2H-phthalazin-1-on, and the reaction liquid was stirred under reflux for 6 hours. Water was added to the reaction liquid, extracted with chloroform, and the organic layer was washed with saturated saline water. This was dried with anhydrous sodium sulfate, and concentrated under reduced pressure to obtain 4.00 g (yield: 74%) of 1-chloro-4-(4-methoxyphenyl)-phthalazine as a white solid.

Production of 6-(4-methoxyphenyl)-3-phenyl-[1,2,4]triazolo[3,4-a]phthalazine 163 mg (1.2 mmol) of benzohydrazide and 165 mg (1.2 mmol) of triethylamine hydrochloride were added to a xylene solution (5 ml) of 271 mg (1.0 mmol) of the obtained 1-chloro-4-(4-methoxyphenyl)-phthalazine, and then stirred under reflux for 2 hours. Water was added to the reaction liquid, extracted with ethyl acetate, and the organic layer was washed with saturated saline water. This was dried with anhydrous sodium sulfate, and concentrated under reduced pressure to obtain 350 mg of a crude product of 6-(4-methoxyphenyl)-3-phenyl-[1,2,4]triazolo[3,4-a]phthalazine.

Production of 4-(3-phenyl-[1,2,4]triazolo[3,4-a]phthalazin-6-yl)-phenol 1.5 ml (1.5 mmol) of a dichloromethane solution of 1 M boron trifluoride was added to a chloroform solution (4 ml) of 305 mg of the obtained 6-(4-methoxyphenyl)-3-phenyl-[1,2,4]triazolo[3,4-a]phthalazine, and stirred overnight at room temperature. Water was added to the reaction liquid, extracted with chloroform, and the organic layer was washed with saturated saline water. This was dried with anhydrous sodium sulfate, and concentrated under reduced pressure to obtain 400 mg of a crude product of 4-(3-phenyl-[1,2,4]triazolo[3,4-a]phthalazin-6-yl)-phenol.

Production of the Entitled Compound 30 mg (0.15 mmol) of 1-(3-chlorophenyl)-piperidine hydrochloride and 42 mg (0.30 mmol) of potassium carbonate were added to 35 mg (0.1 mmol) of the obtained 4-(3-phenyl-[1,2,4]triazolo[3,4-a]phthalazin-6-yl)-phenol, and stirred at 80° C. for 2 hours.

The reaction liquid was concentrated under reduced pressure, and the resulting residue was purified through silica gel column chromatography (chloroform/methanol=10/1) to obtain 10 mg (yield: 22%) of the entitled compound as a white solid.

$^1$HNMR (CDCl$_3$) δ: 1.60 (br, 8H), 2.14 (m, 2H), 2.60 (m, 4H), 4.15 (t, 2H, J=6.4 Hz), 7.09 (d, 2H, J=8.4 Hz), 7.48 (m, 3H), 7.64 (d, 2H, J=8.8 Hz), 7.73 (t, 1H, J=8.0 Hz), 7.94 (m, 2H), 8.49 (d, 2H, J=6.8 Hz), 8.80 (d, 1H, J=8.0 Hz)

ESI-MS (m/e): 464 [M+H]$^+$

Example 26

6-[4-(3-Piperidin-1-ylpropoxy)-phenyl]-3-(pyridin-3-yl)-[1,2,4]triazolo[3,4-a]phthalazine The compound of Example 26 was obtained as a yellow solid in the same manner as in Example 25 or according to a method similar to it or according to a combination of the method with an ordinary method, but using 1-chloro-4-(4-methoxyphenyl)-phthalazine obtained in Example 25 and nicotinohydrazide.

$^1$HNMR (CDCl$_3$) δ: 1.60 (br, 8H), 2.12 (m, 2H), 2.45 (m, 4H), 4.10 (m, 2H), 7.02 (d, 1H, J=8.8 Hz), 7.10 (d, 1H, J=8.8 Hz), 7.46 (m, 2H), 7.64 (d, 1H, J=8.8 Hz), 7.75 (m, 2H), 7.98 (m, 2H), 8.70 (d, 1H, J=8.8 Hz), 8.79 (m, 2H)

ESI-MS (m/e): 465 [M+H]$^+$

Example 27

6-[4-(3-Piperidin-1-ylpropoxy)-phenyl]-3-(pyridin-2-yl)-[1,2,4]triazolo[3,4-a]phthalazine The compound of Example 27 was obtained in the same manner as in Example 25 or according to a method similar to it or according to a combination of the method with an ordinary method, but using 1-chloro-4-(4-methoxyphenyl)-phthalazine obtained in Example 25 and 2-picolinohydrazide.

$^1$HNMR (CDCl$_3$) δ: 1.60 (br, 8H), 2.07 (m, 2H), 2.50 (m, 4H), 4.13 (t, 2H, J=6.0 Hz), 7.09 (m, 2H), 7.39 (m, 1H), 7.65 (m, 2H), 7.75 (d, 1H, J=8.4 Hz), 7.85 (d, 1H, J=7.6 Hz), 7.97 (m, 2H), 8.47 (d, 1H, J=7.6 Hz), 8.85 (d, 2H, J=8.0 Hz)

ESI-MS (m/e): 465 [M+H]$^+$

Example 28

3-Phenyl-6-[4-(3-piperidin-1-ylpropoxy)-phenyl]-pyrido[3,2-d][1,2,4]triazolo[4,3-b]pyridazine The compound of Example 28 was obtained as a pale yellow solid in the same manner as in Example 22 or according to a method similar to it or according to a combination of the method with an ordinary method, but using 5-chloro-8-(4-methoxyphenyl)-pyrido[2,3-d]pyridazine obtained in Example 22 and benzohydrazide in place of formylhydrazide.

$^1$HNMR (CDCl$_3$) δ: 1.60 (br, 8H), 2.05 (m, 2H), 2.4 (m, 4H), 4.12 (t, 2H, J=6.8 Hz), 7.09 (d, 2H, J=9.2 Hz), 7.52 (m, 3H), 7.80 (m, 1H), 8.05 (d, 2H, J=8.8 Hz), 8.52 (dd, 2H, J=1.6, 8.0 Hz), 9.06 (dd, 1H, J=2.0, 8.0 Hz), 9.11 (m, 1H)

ESI-MS (m/e): 465 [M+H]$^+$

Example 29

6-[4-(3-Piperidin-1-ylpropoxy)-phenyl-pyrido[2,3-d][1,2,4]triazolo[4,3-b]pyridazine The compound of Example 29 was obtained as a white solid in the same manner as in Example 22 or according to a method similar to it or according to a combination of the method with an ordinary method, but using 5-chloro-8-(4-methoxyphenyl)-pyrido-[2,3-d]pyridazine obtained in Example 22.

$^1$HNMR (CDCl$_3$) δ: 1.60 (br, 8H), 2.10 (m, 2H), 2.50 (m, 4H), 4.25 (m, 2H), 7.09 (d, 2H, J=8.8 Hz), 7.60 (d, 1H, J=8.4 Hz), 7.69 (m, 2H), 8.27 (d, 1H, J=8.0 Hz), 9.11 (s, 1H), 9.22 (d, 1H, J=6.0 Hz)

ESI-MS (m/e): 389 [M+H]$^+$

Example 30

3-Methyl-6-[4-(3-piperidin-1-ylpropoxy)-phenyl]-pyrido[3,2-d][1,2,4]triazolo[4,3-b]pyridazine The compound of Example 30 was obtained as a white solid in the same manner as in Example 22 or according to a method similar to it or according to a combination of the method with an ordinary method, but using 5-chloro-8-(4-methoxyphenyl)-pyrido-[2,3-d]pyridazine obtained in Example 22 and acetohydrazide in place of formylhydrazide.

$^1$HNMR (CDCl$_3$) δ: 1.60 (br, 8H), 2.05 (m, 2H), 2.50 (m, 4H), 2.86 (s, 3H), 4.12 (t, 2H, J=6.4 Hz), 7.07 (d, 2H, J=8.8 Hz), 7.78 (m, 1H), 7.98 (d, 2H, J=8.8 Hz), 8.97 (dd, 1H, J=1.6, 8.0 Hz), 9.08 (m, 1H)

ESI-MS (m/e): 403 [M+H]$^+$

Example 31

3-Methyl-6-[4-(3-piperidin-1-ylpropoxy)-phenyl]-pyrido[2,3-d][1,2,4]triazolo[4,3-b]pyridazine The compound of Example 31 was obtained as a white solid in the same manner as in Example 22 or according to a method similar to it or according to a combination of the method with an ordinary method, but using 8-chloro-5-(4-methoxyphenyl)-pyrido-[2,3-d]pyridazine obtained in Example 22 and acetohydrazide in place of formylhydrazide.

$^1$HNMR (CDCl$_3$) δ: 1.60 (br, 8H), 2.05 (m, 2H), 2.50 (m, 4H), 2.87 (s, 3H), 4.11 (t, 2H, J=6.4 Hz), 7.11 (d, 2H, J=8.4 Hz), 7.57 (d, 2H, J=8.4 Hz), 7.64 (m, 1H), 8.25 (d, 1H, J=8.4 Hz), 9.17 (dd, 1H, J=2.0, 4.8 Hz)

ESI-MS (m/e): 403 [M+H]$^+$

Example 32

6-[4-(3-Piperidin-1-ylpropoxy)phenyl]-[1,2,4]triazolo[3,4-a]phthalazine

The compound of Example 32 was obtained as a white solid in the same manner as in Example 25 or according to a method similar to it or according to a combination of the method with an ordinary method, but using 1-chloro-4-(4-methoxyphenyl)-phthalazine obtained in Example 25 and formylhydrazide in place of benzohydrazide.

$^1$HNMR (CDCl$_3$) δ: 1.60 (br, 8H), 2.05 (m, 2H), 2.50 (m, 4H), 4.12 (t, 2H, J=6.0 Hz), 7.09 (d, 2H, J=8.8 Hz), 7.58 (d, 2H, J=8.8 Hz), 7.74 (t, 1H, J=7.2 Hz), 7.96 (m, 2H), 8.75 (d, 1H, J=8.0 Hz), 9.03 (s, 1H)

ESI-MS (m/e): 388 [M+H]$^+$

Example 33

3-Methyl-6-[4-(3-piperidin-1-ylpropoxy)phenyl]-[1,2,4]triazolo[3,4-a]phthalazine The compound of Example 33 was obtained in the same manner as in Example 25 or according to a method similar to it or according to a combination of the method with an ordinary method, but using 1-chloro-4-(4-methoxyphenyl)-phthalazine obtained in Example 25 and acetohydrazide in place of benzohydrazide.

$^1$HNMR (CDCl$_3$) δ: 1.60 (br, 8H), 2.05 (m, 2H), 2.50 (m, 4H), 2.84 (s, 3H), 4.14 (t, 2H, J=6.0 Hz), 7.10 (d, 2H, J=8.4 Hz), 7.61 (d, 2H, J=8.8 Hz), 7.72 (t, 1H, J=7.6 Hz), 7.93 (m, 2H), 8.73 (d, 1H, J=7.6 Hz)

ESI-MS (m/e): 402 [M+H]$^+$

Example 34

6-[4-(3-Piperidin-1-ylpropoxy)phenyl]-3-trifluoromethyl-[1,2,4]triazolo[3,4-a]phthalazine The compound of Example 34 was obtained as a pale yellow solid in the same manner as in Example 25 or according to a method similar to it or according to a combination of the method with an ordinary method, but using 1-chloro-4-(4-methoxyphenyl)-phthalazine obtained in Example 25 and trifluoroacetohydrazide in place of benzohydrazide.

$^1$HNMR (CDCl$_3$) δ: 1.60 (br, 8H), 2.10 (m, 2H), 2.50 (m, 4H), 4.13 (t, 2H, J=6.4 Hz), 7.09 (d, 2H, J=8.8 Hz), 7.61 (d, 2H, J=8.8 Hz), 7.84 (m, 1H), 8.00 (t, 1H, J=8.4 Hz), 8.05 (d, 1H, J=7.6 Hz), 8.81 (d, 1H, J=8.4 Hz)

ESI-MS (m/e): 456 [M+H]$^+$

Example 35

3-tert-butyl-6-[4-(3-piperidin-1-ylpropoxy)phenyl]-[1,2,4]triazolo[3,4-a]phthalazine The compound of Example 35 was obtained as a yellow solid in the same manner as in Example 25 or according to a method similar to it or according to a combination of the method with an ordinary method, but using 1-chloro-4-(4-methoxyphenyl)-phthalazine obtained in Example 25 and pivalohydrazide in place of benzohydrazide.

$^1$HNMR (CDCl$_3$) δ: 1.60 (br, 8H), 1.65 (s, 9H), 2.10 (m, 2H), 2.50 (m, 4H), 4.13 (t, 2H, J=6.0 Hz), 7.08 (d, 2H, J=8.8 Hz), 7.60 (d, 2H, J=8.8 Hz), 7.71 (m, 1H), 7.87 (t, 1H, J=6.8 Hz), 7.93 (d, 1H, J=8.0 Hz), 8.72 (d, 1H, J=8.4 Hz)

ESI-MS (m/e): 444 [M+H]$^+$

Example 36

6-[4-(1-Cyclopentyl-piperidin-4-yloxy)phenyl]-[1,2,4]triazolo[4,3-b]pyridazine The compound of Example 36 was obtained as a pale yellow solid in the same manner as in Example 10 and Example 2 or according to a method similar to it or according to a combination of the method with an ordinary method, but using 4-[1,2,4]triazolo[4,3-b]pyridazin-6-yl-phenol obtained in Example 10.

$^1$HNMR (CDCl$_3$) δ: 1.26 (br, 2H), 1.63 (br, 5H), 1.91 (m, 4H), 2.10 (m, 2H), 2.43 (br, 1H), 2.59 (br, 1H), 2.85 (br, 2H), 4.47 (br, 1H), 7.04 (d, 2H, J=9.5 Hz), 7.55 (d, 1H, J=9.5 Hz), 7.91 (d, 2H, J=8.8 Hz), 8.14 (d, 1H, J=9.5 Hz), 9.10 (s, 1H)

ESI-MS (m/e): 364 [m+H]$^+$

Example 37

6-[4-(1-Cyclobutyl-piperidin-4-yloxy)phenyl]-[1,2,4]triazolo[4,3-b]pyridazine The compound of Example 37 was obtained as a pale yellow solid in the same manner as in Example 10 and Example 2 or according to a method similar to it or according to a combination of the method with an ordinary method, using 4-[1,2,4]triazolo[4,3-b]pyridazin-6-yl-phenol obtained in Example 10 and using cyclobutanone in place of cyclopentanone used in Example 2.

$^1$HNMR (CDCl$_3$) δ: 1.74 (m, 2H), 1.89 (m, 4H), 2.05 (m, 4H), 2.22 (br, 2H), 2.59 (br, 1H), 2.64 (m, 1H), 2.77 (m, 1H), 4.45 (br, 1H), 7.03 (d, 2H, J=8.8 Hz), 7.55 (d, 1H, J=9.5 Hz), 7.90 (d, 2H, J=8.8 Hz), 8.13 (d, 1H, J=9.5 Hz), 9.10 (s, 1H)
ESI-MS (m/e): 350 [M+H]$^+$

Example 38

6-[4-(1-Cyclopentyl-piperidin-4-yloxy)phenyl]-3-methyl-[1,2,4]triazolo[4,3-b]pyridazine The compound of Example 38 was obtained as a pale yellow solid in the same manner as in Example 10 and Example 2 or according to a method similar to it or according to a combination of the method with an ordinary method, but using 3-chloro-6-(4-methoxyphenyl)-pyridazine obtained in Example 10 and acetohydrazide in place of formylhydrazide.
$^1$HNMR (CDCl$_3$) δ: 1.43 (br, 2H), 1.65 (br, 4H), 1.88 (m, 4H), 2.05 (m, 2H), 2.38 (br, 2H), 2.52 (br, 1H), 2.83 (br, 2H), 2.86 (s, 3H), 4.44 (br, 1H), 7.05 (d, 2H, J=9.2 Hz), 7.51 (d, 1H, J=9.6 Hz), 7.94 (d, 2H, J=8.8 Hz), 8.08 (d, 1H, J=10.0 Hz)
ESI-MS (m/e): 378 [M+H]$^+$

Example 39

6-[4-(1-Cyclopentyl-piperidin-4-yloxy)phenyl]-7-methyl-[12.4]triazolo[4,3-b]pyridazine The compound of Example 39 was obtained as a pale yellow solid in the same manner as in Example 10 and Example 2 or according to a method similar to it or according to a combination of the method with an ordinary method, but using 4'-methoxypropiophenone in place of 4'-methoxyacetophenone.
$^1$HNMR (CDCl$_3$) δ: 1.44 (m, 2H), 1.56 (m, 2H), 1.71 (m, 2H), 1.90 (m, 4H), 2.05 (m, 2H), 2.40 (s, 3H), 2.30 (br, 2H), 2.55 (m, 1H), 2.84 (br, 2H), 4.42 (br, 1H), 7.04 (d, 2H, J=8.4 Hz), 7.45 (d, 2H, J=8.8 Hz), 7.94 (s, 1H), 9.05 (s, 1H)
ESI-MS (m/e): 378 [M+H]$^+$

Example 40

7-[4-(3-Piperidin-1-ylpropoxy)-phenyl]-[1,2,4]triazolo[4,3-b]pyridazine

The compound of Example 40 was obtained as a yellow solid in the same manner as in Example 19 or according to a method similar to it or according to a combination of the method with an ordinary method, but using 4-methoxyphenylacetaldehyde in place of 4-methoxyphenylacetone.
$^1$HNMR (CDCl$_3$) δ: 1.50 (br, 8H), 2.06 (m, 2H), 2.50 (m, 4H), 4.10 (t, 2H, J=6.0 Hz), 7.07 (d, 2H, J=8.4 Hz), 7.60 (d, 2H, J=8.8 Hz), 8.14 (d, 1H, J=1.2 Hz), 8.65 (d, 1H, J=2.0 Hz), 9.10 (s, 1H)
ESI-MS (m/e): 338 [M+H]$^+$

Example 41

7-[4-(1-Cyclopentyl-piperidin-4-yloxy)phenyl]-3-methyl-[1,2,4]triazolo[4,3-b]pyridazine The compound of Example 41 was obtained as a white solid in the same manner as in Example 19 and Example 2 or according to a method similar to it or according to a combination of the method with an ordinary method, but using 4-methoxyphenylacetaldehyde in place of 4-methoxyphenylacetone and acetohydrazide in place of formylhydrazide.
$^1$HNMR (CDCl$_3$) δ: 1.44 (br, 2H), 1.61 (br, 4H), 1.90 (m, 4H), 2.05 (m, 2H), 2.39 (br, 2H), 2.55 (br, 1H), 2.83 (br, 2H), 2.84 (s, 3H), 4.42 (br, 1H), 7.06 (d, 2H, J=9.2 Hz), 7.58 (d, 2H, J=9.2 Hz), 8.07 (d, 1H, J=2.4 Hz), 8.62 (d, 1H, J=2.4 Hz)
ESI-MS (m/e): 378 [M+H]$^+$

Example 42

7-[4-(1-Cyclopentyl-piperidin-4-yloxy)phenyl]-6-methyl-[1,2,4]triazolo[4,3-b]pyridazine The compound of Example 42 was obtained as a pale yellow oily substance in the same manner as in Example 19 and Example 2 or according to a method similar to it or according to a combination of the method with an ordinary method.
$^1$HNMR (CDCl$_3$) δ: 1.26 (m, 2H), 1.47 (m, 2H), 1.57 (m, 2H), 1.72 (m, 2H), 1.90 (m, 4H), 2.08 (m, 2H), 2.42 (br, 1H), 2.50 (s, 3H), 2.86 (br, 2H), 4.42 (br, 1H), 7.02 (d, 2H, J=8.8 Hz), 7.27 (d, 2H, J=8.4 Hz), 7.86 (d, 1H, J=4.8 Hz), 9.04 (s, 1H)
ESI-MS (m/e): 378 [M+H]

Example 43

7-[4-(1-Cyclopentyl-piperidin-4-yloxy)phenyl]-3,6-dimethyl-[1,2,4]triazolo[4,3-b]pyridazine The compound of Example 43 was obtained as a pale yellow oily substance in the same manner as in Example 19 and Example 2 or according to a method similar to it or according to a combination of the method with an ordinary method, but using acetohydrazide in place of formylhydrazide.
$^1$HNMR (CDCl$_3$) δ: 1.57 (m, 4H), 1.73 (m, 2H), 1.92 (m, 4H), 2.11 (m, 2H), 2.35 (m, 1H), 2.50 (s, 3H), 2.62 (m, 2H), 2.83 (s, 3H), 2.87 (m, 2H), 4.42 (br, 1H), 7.01 (d, 2H, J=8.8 Hz), 7.26 (d, 2H, J=8.4 Hz), 7.79 (s, 1H)
ESI-MS (m/e): 392 [M+H]$^+$

Example 44

7-[4-(1-Cyclopentyl-piperidin-4-yloxy)phenyl]-[1,2,4]triazolo[4,3-b]pyridazine

The compound of Example 44 was obtained as a yellow solid in the same manner as in Example 19 and Example 2 or according to a method similar to it or according to a combination of the method with an ordinary method, but using 4-methoxyphenylacetaldehyde in place of 4-methoxyphenylacetone.
$^1$HNMR (CDCl$_3$) δ: 1.43 (br, 2H), 1.62 (br, 5H), 1.90 (m, 4H), 2.05 (m, 2H), 2.38 (br, 1H), 2.55 (br, 1H), 2.83 (br, 2H), 4.42 (br, 1H), 7.07 (d, 2H, J=8.4 Hz), 7.59 (d, 2H, J=8.4 Hz), 8.14 (d, 1H, J=1.6 Hz), 8.65 (d, 1H, J=2.0 Hz), 9.10 (s, 1H)
ESI-MS (m/e): 364 [M+H]$^+$

Example 45

7-[4-(1-Cyclobutyl-piperidin-4-yloxy)-phenyl]-[1,2,4]triazolo[4,3-b]pyridazine

The compound of Example 45 was obtained as a yellow solid in the same manner as in Example 19 and Example 2 or according to a method similar to it or according to a combination of the method with an ordinary method, but using 4-methoxyphenylacetaldehyde in place of 4-methoxyphenylacetone and cyclobutanone in place of cyclopentanone.

¹HNMR (CDCl₃) δ: 1.70 (m, 2H), 1.88 (m, 4H), 2.05 (m, 4H), 2.19 (br, 2H), 2.65 (m, 2H), 2.76 (m, 1H), 4.43 (br, 1H), 7.07 (d, 2H, J=8.8 Hz), 7.59 (d, 2H, J=8.8 Hz), 8.14 (d, 1H, J=1.6 Hz), 8.65 (d, 1H, J=2.0 Hz), 9.10 (s, 1H)
ESI-MS (m/e): 350 [M+H]$^+$

Example 46

6-[4-(1-Cyclopentyl-piperidin-4-yloxy)-phenyl]-[1,2,4]triazolo[3,4-a]phthalazine The compound of Example 46 was obtained as a white solid in the same manner as in Example 25 and Example 2 or according to a method similar to it or according to a combination of the method with an ordinary method, but using formylhydrazide in place of benzohydrazide.
¹HNMR (CDCl₃) δ: 1.44 (br, 2H), 1.69 (br, 4H), 1.91 (m, 4H), 2.08 (m, 2H), 2.40 (br, 2H), 2.56 (br, 1H), 2.85 (br, 2H), 4.45 (br, 1H), 7.10 (d, 2H, J=8.6 Hz), 7.58 (d, 2H, J=9.8 Hz), 7.76 (d, 1H, J=7.0 Hz), 7.96 (q, 2H, J=7.3 Hz), 8.76 (d, 1H, J=7.8 Hz), 9.06 (s, 1H)
ESI-MS (m/e): 414 [M+H]$^+$

Example 47

6-[4-(1-Cyclopentyl-piperidin-4-yloxy)-phenyl]-3-methyl-[1,2,4]triazolo[3,4-a]phthalazine The compound of Example 47 was obtained as a pale yellow solid in the same manner as in Example 25 or according to a method similar to it or according to a combination of the method with an ordinary method, but using acetohydrazide in place of benzohydrazide.
¹HNMR (CDCl₃) δ: 1.60 (m, 4H), 1.72 (m, 2H), 1.90 (m, 4H), 2.08 (m, 2H), 2.40 (br, 2H), 2.56 (m, 1H), 2.84 (s, 3H), 2.86 (br, 1H), 3.73 (m, 1H), 4.46 (br, 1H), 7.09 (d, 2H, J=8.6 Hz), 7.60 (d, 2H, J=8.6 Hz), 7.72 (t, 1H, J=7.8 Hz), 7.92 (q, 2H, J=7.3 Hz), 8.72 (d, 1H, J=7.8 Hz)
ESI-MS (m/e): 428 [M+H]$^+$

Example 48

6-[4-(3-Pyrrolidin-1-ylpropoxy)phenyl]-[1,2,4]triazolo[4,3-b]pyridazine

The compound of Example 48 was obtained as a pale yellow solid in the same manner as in Example 10 or according to a method similar to it or according to a combination of the method with an ordinary method, but using 1-(3-chloropropyl)pyrrolidine in place of 1-(3-chloropropyl)piperidine.
¹HNMR (CDCl₃) δ: 1.86 (br, 6H), 2.12 (m, 2H), 2.42 (m, 4H), 4.14 (t, 2H, J=6.0 Hz), 7.05 (d, 2H, J=9.2 Hz), 7.57 (d, 1H, J=10.0 Hz), 7.92 (d, 2H, J=8.4 Hz), 8.15 (d, 1H, J=9.2 Hz), 9.11 (s, 1H)
ESI-MS (m/e): 324 [M+H]$^+$

Example 49

3-Methyl-7-[4-(3-piperidin-1-ylpropoxy)phenyl]-[1,2,4]triazolo[4,3-b]pyridazine

The compound of Example 49 was obtained as a pale yellow solid in the same manner as in Example 10 or according to a method similar to it or according to a combination of the method with an ordinary method, but using 3-chloro-6-(4-methoxyphenyl)-pyridazine obtained in Example 10 and acetohydrazide in place of formylhydrazide.

¹HNMR (CDCl₃) δ: 1.50 (br, 6H), 2.04 (m, 4H), 2.50 (m, 4H), 2.84 (s, 3H), 4.09 (t, 2H, J=6.4 Hz), 7.06 (d, 2H, J=9.2 Hz), 7.58 (d, 2H, J=8.8 Hz), 8.07 (d, 1H, J=2.0 Hz), 8.62 (d, 1H, J=2.0 Hz)
ESI-MS (m/e): 352 [M+H]$^+$

Example 50

7-[4-(1-Cyclobutyl-piperidin-4-yloxy)phenyl]-3-methyl-[1,2,4]triazolo[4,3-b]pyridazine The compound of Example 50 was obtained as a white solid in the same manner as in Example 19 and Example 2 or according to a method similar to it or according to a combination of the method with an ordinary method, but using 4-methoxyphenylacetaldehyde in place of 4-methoxyphenylacetone, acetohydrazide in place of formylhydrazide, and cyclobutanone in place of cyclopentanone.
¹HNMR (CDCl₃) δ: 1.74 (m, 2H), 1.93 (m, 4H), 2.05 (m, 4H), 2.21 (m, 2H), 2.65 (br, 2H), 2.77 (m, 1H), 2.84 (s, 3H), 4.42 (br, 1H), 7.06 (d, 2H, J=8.8 Hz), 7.58 (d, 1H, J=8.8 Hz), 8.07 (d, 2H, J=2.0 Hz), 8.62 (d, 1H, J=2.0 Hz)
ESI-MS (m/e): 364 [M+H]$^+$

Example 51

6-[4-(1-Cyclobutyl-piperidin-4-yloxy)phenyl]-3-methyl-[1,2,4]triazolo[4,3-b]pyridazine The compound of Example 51 was obtained as a pale yellow solid in the same manner as in Example 10 and Example 2 or according to a method similar to it or according to a combination of the method with an ordinary method, but using 3-chloro-6-(4-methoxyphenyl)-pyridazine obtained in Example 10, acetohydrazide in place of formylhydrazide, and cyclobutanone in place of cyclopentanone.
¹HNMR (CDCl₃) δ: 1.72 (m, 2H), 1.90 (m, 4H), 2.06 (m, 4H), 2.20 (br, 2H), 2.64 (m, 2H), 2.76 (m, 1H), 2.86 (s, 3H), 4.44 (br, 1H), 7.05 (d, 2H, J=9.2 Hz), 7.51 (d, 2H, J=9.6 Hz), 7.94 (d, 1H, J=8.4 Hz), 8.08 (d, 1H, J=10.0 Hz)
ESI-MS (m/e): 364 [M+H]$^+$

Example 52

6-[4-(1-Cyclobutyl-piperidin-4-yloxy)phenyl]-[1,2,4]triazolo[3,4-a]phthalazine

The compound of Example 52 was obtained as a white solid in the same manner as in Example 25 and Example 2 or according to a method similar to it or according to a combination of the method with an ordinary method, but using formylhydrazide in place of benzohydrazide, and cyclobutanone in place of cyclopentanone.
¹HNMR (CDCl₃) δ: 1.62 (br, 2H), 1.90 (br, 4H), 2.05 (m, 4H), 2.21 (m, 2H), 2.67 (br, 2H), 2.77 (br, 1H), 4.47 (br, 1H), 7.09 (d, 2H, J=8.6 Hz), 7.59 (d, 2H, J=8.6 Hz), 7.76 (q, 1H, J=6.3 Hz), 7.96 (q, 2H, J=7.0 Hz), 8.76 (d, 1H, J=7.8 Hz), 9.06 (s, 1H)
ESI-MS (m/e): 400 [M+H]$^+$

Example 53

6-[4-(1-Cyclobutyl-piperidin-4-yloxy)phenyl]-7-methyl-[1,2,4]triazolo[4,3-b]pyridazine The compound of Example 53 was obtained as a pale yellow solid in the same manner as in Example 2 and Example 10 or according to a method similar to it or according to a combination of the method with an ordinary method, but using 4'-methoxypropiophenone in place of 4'-methoxyacetophenone and using cyclobutanone in place of cyclopentanone used in Example 10 and Example 2.

$^1$HNMR (CDCl$_3$) δ: 1.70 (m, 2H), 1.90 (m, 4H), 2.05 (m, 4H), 2.20 (br, 2H), 2.40 (s, 3H), 2.65 (br, 2H), 2.76 (m, 1H), 4.43 (br, 1H), 7.04 (d, 2H, J=8.4 Hz), 7.45 (d, 2H, J=8.8 Hz), 7.94 (s, 1H), 9.05 (s, 1H)

ESI-MS (m/e): 364 [M+H]$^+$

Example 54

7-[4-(1-Cyclobutyl-piperidin-4-yloxy)phenyl]-6-methyl-[1,2,4]triazolo[4,3-b]pyridazine The compound of Example 54 was obtained as a pale yellow oily substance in the same manner as in Example 42 or according to a method similar to it or according to a combination of the method with an ordinary method, but using cyclobutanone in place of cyclopentanone.

$^1$HNMR (CDCl$_3$) δ: 1.73 (m, 4H), 1.91 (m, 4H), 2.06 (m, 4H), 2.24 (m, 1H), 2.50 (s, 3H), 2.68 (m, 1H), 2.79 (m, 1H), 4.41 (br, 1H), 7.02 (d, 2H, J=8.8 Hz), 7.27 (d, 2H, J=8.4 Hz), 7.86 (d, 1H, J=4.4 Hz), 9.04 (s, 1H)

ESI-MS (m/e): 364 [M+H]$^+$

Example 55

7-[4-(1-Cyclobutyl-piperidin-4-yloxy)phenyl]-3,6-dimethyl-[1,2,4]triazolo[4,3-b]pyridazine The compound of Example 55 was obtained as a pale yellow oily substance in the same manner as in Example 43 or according to a method similar to it or according to a combination of the method with an ordinary method, but using cyclobutanone in place of cyclopentanone.

$^1$HNMR (CDCl$_3$) δ: 1.70 (m, 2H), 1.90 (m, 4H), 2.05 (m, 4H), 2.19 (m, 2H), 2.50 (s, 3H), 2.66 (m, 2H), 2.77 (m, 1H), 2.83 (s, 3H), 4.40 (br, 1H), 7.02 (d, 2H, J=8.8 Hz), 7.26 (d, 2H, J=8.4 Hz), 7.79 (s, 1H)

ESI-MS (m/e): 378 [M+H]$^+$

Example 56

6-[4-(1-Cyclobutyl-piperidin-4-yloxy)phenyl]-3-methyl-[1,2,4]triazolo[3,4-a]phthalazine The compound of Example 56 was obtained as a white solid in the same manner as in Example 47 or according to a method similar to it or according to a combination of the method with an ordinary method, but using cyclobutanone in place of cyclopentanone.

$^1$HNMR (CDCl$_3$) δ: 1.73 (m, 2H), 1.93 (m, 4H), 2.07 (m, 4H), 2.24 (m, 2H), 2.67 (m, 2H), 2.79 (m, 1H), 2.84 (s, 3H), 4.48 (br, 1H), 7.09 (d, 2H, J=8.6 Hz), 7.60 (d, 2H, J=8.6 Hz), 7.71 (t, 1H, J=7.8 Hz), 7.92 (q, 2H, J=7.0 Hz), 8.72 (d, 1H, J=7.8 Hz)

ESI-MS (m/e): 414 [M+H]$^+$

Example 57

6-{-4-[3-(2,6-dimethylpiperidin-1-yl}propoxyl-phenyl}-[1,2,4]triazolo[4,3-b]pyridazine The compound of Example 57 was obtained as a pale yellow oily substance in the same manner as in Example 10 or according to a method similar to it or according to a combination of the method with an ordinary method, but using 1-(3-chloropropyl)-2,6-dimethylpiperidine hydrochloride in place of 1-(3-chloropropyl)piperidine hydrochloride.

$^1$HNMR (CDCl$_3$) δ: 1.16 (6H, d, J=6.3 Hz), 1.25-1.37 (2H, m), 1.53-1.65 (4H, m), 1.91-1.98 (2H, m), 2.48 (2H, br), 2.94-3.00 (2H, m), 4.03 (2H, t, J=5.9 Hz), 7.04 (2H, d, J=8.6 Hz), 7.57 (1H, d, J=10.2 Hz), 7.93 (2H, d, J=8.6 Hz), 8.15 (1H, d, J=10.2 Hz), 9.11 (1H, s)

ESI-MS (m/e): 366 [M+H]$^+$

Example 58

6-{-4-[3-(2,5-dimethylpyrrolidin-1-yl)propoxy]-phenyl}-1-[1,2,4]triazolo[4,3-b]pyridazine The compound of Example 58 was obtained as a white solid in the same manner as in Example 10 or according to a method similar to it or according to a combination of the method with an ordinary method, but using 1-(3-chloropropyl)-2,5-dimethylpyrrolidine hydrochloride in place of 1-(3-chloropropyl)piperidine hydrochloride.

$^1$HNMR (CDCl$_3$) δ: 0.99 (6H, d, J=6.2 Hz), 1.36-1.42 (2H, m), 1.70 (2H, br), 1.95-2.10 (2H, m), 2.55-2.63 (1H, m), 2.74-2.83 (1H, m), 3.03-3.12 (2H, m), 4.08-4.15 (2H, m), 7.06 (2H, d, J=9.0 Hz), 7.57 (1H, d, J=9.8 Hz), 7.92 (2H, d, J=9.0 Hz), 8.14 (1H, d, J=9.8 Hz), 9.11 (1H, s)

ESI-MS (m/e): 352 [M+H]$^+$

Example 59

N-methyl-6-[4-(3-piperidin-1-ylpropoxy)-phenyl]-[1,2,4]triazolo[4,3-b]pyridazine-3-carboxamide Production of ethyl 6-(4-methoxyphenyl)[1,2,4]triazolo[4,3-b]pyridazine-3-carboxylate 2.09 ml (15.0 mmol) of triethylamine and 1.23 ml (11.0 mmol) of ethyloxalyl chloride were added to a dioxane solution (20 ml) of 2.16 g (10.0 mmol) of 3-hydrazino-6-(4-methoxyphenyl)pyridazine, obtained according to the method described in *Journal of Medicinal Chemistry*, Vol. 30, pp. 239-249 (1987), and the reaction liquid was stirred at 60° C. for 4 hours. The reaction liquid was concentrated under reduced pressure, and acetic acid (10 ml) was added to the resulting residue and stirred at 120° C. for 2 hours. The reaction liquid was concentrated under reduced pressure, and the resulting residue was purified through silica gel column chromatography (hexane/ethyl acetate=1/4) to obtain 615 mg (yield: 21%) of ethyl 6-(4-methoxyphenyl)[1,2,4]triazolo[4,3-b]pyridazine-3-carboxylate.

Production of 6-(4-hydroxyphenyl)-N-methyl[1,2,4]triazolo[4,3-b]pyridazine-3-carboxamide Methylamine/methanol solution (3 ml) was added to a methanol solution of 307 mg (0.97 mmol) of ethyl 6-(4-methoxyphenyl)[1,2,4]triazolo[4,3-b]pyridazine-3-carboxylate, and stirred at room temperature for 14 hours. The reaction liquid was concentrated under reduced pressure, and 2 ml (2.00 mol) of a dichloromethane solution of 1 M boron tribromide was added to a chloroform solution (4 ml) of the resulting residue, and stirred overnight at room temperature. Water was added to the reaction liquid, extracted with chloroform, and the organic layer was washed with saturated saline water. This was dried with anhydrous sodium sulfate, and concentrated under reduced pressure to obtain 65 mg of a crude product of 6-(4-hydroxyphenyl)-N-methyl[1,2,4]triazolo[4,3-b]pyridazine-3-carboxamide.

Production of the Entitled Compound 96 mg (0.48 mol) of 1-(3-chlorophenyl)-piperidine hydrochloride and 66 mg (0.48 mmol) of potassium carbonate were added to 65 mg (0.24 mmol) of 6-(4-hydroxyphenyl)-N-methyl[1,2,4]triazolo[4,3-b]pyridazine-3-carboxamide, and stirred at 80° C. for 2 hours.

The reaction liquid was concentrated under reduced pressure, and the resulting residue was purified through silica gel column chromatography (chloroform/methanol=10/1) to obtain 61 mg (yield: 64%) of the entitled compound as a white solid.

$^1$HNMR (CDCl$_3$) δ: 1.41-1.49 (2H, m), 1.58-1.63 (5H, m), 1.99-2.06 (2H, m), 2.42 (3H, s), 2.50 (2H, t, J=7.4 Hz), 3.16 (3H, d, J=5.1 Hz), 4.11 (2H, t, J=6.3 Hz), 7.06 (2H, d, J=9.0 Hz), 7.69 (1H, d, J=9.8 Hz), 7.83 (1H, br), 7.99 (2H, d, J=9.0 Hz), 8.23 (1H, d, J=9.8 Hz)

ESI-MS (m/e): 395 [M+H]$^+$

Example 60

3-(Piperidin-1-ylcarbonyl)-6-[4-(3-piperidin-1-ylpropoxy)-phenyl]-[1,2,4]triazolo[4,3-b]pyridazine The compound of Example 60 was obtained as a pale yellow solid in the same manner as in Example 59 or according to a method similar to it or according to a combination of the method with an ordinary method, but using ethyl 6-(4-methoxyphenyl)[1,2,4]triazolo[4,3-b]pyridazine-3-carboxylate obtained in Example 59 and using piperidine in place of methylamine.

$^1$HNMR (CDCl$_3$) δ: 1.42-1.81 (14H, m), 2.00-2.10 (2H, m), 2.40-2.58 (4H, m), 3.65 (2H, t, J=5.3 Hz), 3.87 (2H, t, J=5.1 Hz), 4.10 (2H, t, J=6.5 Hz), 7.02 (2H, d, J=9.0 Hz), 7.62 (1H, d, J=9.8 Hz), 7.96 (2H, d, J=9.0 Hz), 8.16 (1H, d, J=9.8 Hz).

ESI-MS (m/e): 449 [M+H]$^+$

Example 61

6-[4-(3-Methylpiperidin-1-ylpropoxy)-phenyl]-[1,2,4]triazolo[4,3-b]pyridazine

The compound of Example 61 was obtained as a white solid in the same manner as in Example 10 or according to a method similar to it or according to a combination of the method with an ordinary method, but using 1-(3-chloropropyl)-2-methylpiperidine hydrochloride in place of 1-(3-chloropropyl)piperidine hydrochloride.

$^1$HNMR (CDCl$_3$) δ: 1.08 (3H, d, J=6.3 Hz), 1.22-1.33 (2H, m), 1.55-1.68 (4H, m), 1.95-2.02 (2H, m), 2.15-2.21 (1H, m), 2.26-2.35 (1H, m), 2.47-2.54 (1H, m), 2.85-2.94 (2H, m), 4.09 (2H, br), 7.05 (2H, d, J=9.0 Hz), 7.57 (1H, d, J=9.8 Hz), 7.92 (2H, d, J=9.0 Hz), 8.14 (1H, d, J=9.8 Hz), 9.11 (1H, d, J=0.8 Hz)

ESI-MS (m/e): 352 [M+H]$^+$

Example 62

6-(4-{3-[(3S)-3-fluoropyrrolidin-1-yl]propoxy}-phenyl)-[1,2,4]triazolo[4,3-b]pyridazine The compound of Example 62 was obtained as a white solid in the same manner as in Example 10 or according to a method similar to it or according to a combination of the method with an ordinary method, but using (3S)-1-(3-chloropropyl)-3-fluoropyrrolidine hydrochloride in place of 1-(3-chloropropyl)piperidine hydrochloride.

$^1$HNMR (CDCl$_3$) δ: 1.60 (2H, d, J=10.9 Hz), 2.00-2.07 (2H, m), 2.40-2.47 (1H, m), 2.66-2.71 (2H, m), 2.87-2.92 (1H, m), 3.49 (3H, s), 4.13 (2H, t, J=6.4 Hz), 7.05 (2H, d, J=9.0 Hz), 7.57 (1H, d, J=9.8 Hz), 7.93 (2H, d, J=9.0 Hz), 8.15 (1H, dd, J=9.8, 0.8 Hz), 9.11 (1H, s)

ESI-MS (m/e): 342 [M+H]$^+$

Example 63

6-{4-[3-(3-methylpiperidin-1-yl)propoxy]-phenyl}-[1,2,4]triazolo[4,3-b]pyridazine The compound of Example 63 was obtained as a white solid in the same manner as in Example 10 or according to a method similar to it or according to a combination of the method with an ordinary method, but using 1-(3-chloropropyl)-3-methylpiperidine hydrochloride in place of 1-(3-chloropropyl)piperidine hydrochloride.

$^1$HNMR (CDCl$_3$) δ: 0.87 (3H, d, J=6.3 Hz), 1.53-1.76 (5H, m), 1.76-1.90 (2H, m), 1.99-2.06 (2H, m), 2.50 (2H, m), 2.86 (2H, t, J=13.5 Hz), 4.10 (2H, t, J=6.5 Hz), 7.05 (2H, d, J=9.0 Hz), 7.57 (1H, d, J=9.8 Hz), 7.92 (2H, d, J=9.0 Hz), 8.14 (1H, d, J=9.8 Hz), 9.11 (1H, s)

ESI-MS (m/e): 352 [M+H]$^+$

Example 64

6-{4-[3-(4-fluoropiperidin-1-yl)propoxy]-phenyl}-[1,2,4]triazolo[4,3-b]pyridazine The compound of Example 64 was obtained as a white solid in the same manner as in Example 10 or according to a method similar to it or according to a combination of the method with an ordinary method, but using 1-(3-chloropropyl)-4-fluoropiperidine hydrochloride in place of 1-(3-chloropropyl)piperidine hydrochloride.

$^1$HNMR (CDCl$_3$) δ: 1.81-2.05 (7H, m), 2.37-2.47 (2H, m), 2.52-2.66 (4H, m), 4.11 (2H, t, J=6.3 Hz), 7.05 (2H, d, J=9.0 Hz), 7.57 (1H, d, J=9.8 Hz), 7.93 (2H, d, J=9.0 Hz), 8.15 (1H, dd, J=9.8, 0.8 Hz), 9.11 (1H, s)

ESI-MS (m/e): 356 [M+H]$^+$

Example 65

6-{4-[3-(3-fluoropiperidin-1-yl)propoxy]-phenyl}-[1,2,4]triazolo[4,3-b]pyridazine The compound of Example 65 was obtained as a white solid in the same manner as in Example 10 or according to a method similar to it or according to a combination of the method with an ordinary method, but using 1-(3-chloropropyl)-3-fluoropiperidine hydrochloride in place of 1-(3-chloropropyl)piperidine hydrochloride.

$^1$HNMR (CDCl$_3$) δ: 1.52-1.71 (2H, m), 1.81-2.06 (7H, m), 2.47-2.60 (4H, m), 4.09-4.16 (2H, m), 7.05 (2H, d, J=9.0 Hz), 7.57 (1H, d, J=9.8 Hz), 7.92 (2H, d, J=9.0 Hz), 8.14 (1H, dd, J=9.8, 0.8 Hz), 9.11 (1H, s).

ESI-MS (m/e): 356 [M+H]$^+$

Example 66

6-(4-{3-[(2R)-(2-methylpyrrolidin-1-yl]propoxy)-phenyl}-[1,2,4]triazolo[4,3-b]pyridazine The compound of Example 66 was obtained as a white solid in the same manner as in Example 10 or according to a method similar to it or according to a combination of the method with an ordinary method, but using (2R)-1-(3-chloropropyl)-2-methylpyrrolidine hydrochloride in place of 1-(3-chloropropyl)piperidine hydrochloride.

$^1$HNMR (CDCl$_3$) δ: 1.10 (3H, d, J=6.3 Hz), 1.38-1.48 (1H, m), 1.67-1.83 (2H, m), 1.89-2.34 (6H, m), 2.98-3.02 (1H, m), 3.17-3.12 (1H, m), 4.10-4.15 (2H, m), 7.06 (2H, d, J=9.0 Hz), 7.57 (1H, d, J=10.2 Hz), 7.92 (2H, d, J=9.0 Hz), 8.15 (1H, d, J=10.2 Hz), 9.11 (1H, s)

ESI-MS (m/e): 338 [M+H]$^+$

Example 67

6-(4-{3-[(2S)-(2-methylpyrrolidin-1-yl]propoxy)-phenyl-}-[1,2,4]triazolo[4,3-b]pyridazine The compound of Example 67 was obtained as a white solid in the same manner as in Example 10 or according to a method similar to it or according to a combination of the method with an ordinary method, but using (2S)-1-(3-chloropropyl)-2-methylpyrrolidine hydrochloride in place of 1-(3-chloropropyl)piperidine hydrochloride.

$^1$HNMR (CDCl$_3$) δ: 1.10 (3H, d, J=6.3 Hz), 1.38-1.48 (1H, m), 1.67-1.83 (2H, m), 1.89-2.34 (6H, m), 2.98-3.03 (1H, m), 3.14-3.19 (1H, m), 4.10-4.15 (2H, m), 7.06 (2H, d, J=9.0 Hz), 7.57 (1H, d, J=10.2 Hz), 7.92 (2H, d, J=9.0 Hz), 8.15 (1H, d, J=10.2 Hz), 9.11 (1H, s)

ESI-MS (m/e): 338 [M+H]$^+$

Example 68

N,N-dimethyl-6-(4-{3-[(2R)-(2-methylpyrrolidin-1-yl]propoxy)-phenyl}-[1,2,4]triazolo[3,4-a]phthalazine-3-carboxamide The compound of Example 68 was obtained as a white solid in the same manner as in Example 59 or according to a method similar to it or according to a combination of the method with an ordinary method, but using 1-hydrazino-4-(4-methoxyphenyl)phthalazine in place of 3-hydrazino-6-(4-methoxyphenyl)pyridazine.

$^1$HNMR (CDCl$_3$) δ: 1.17 (2H, d, J=5.9 Hz), 1.44-1.54 (1H, m), 1.70-2.47 (8H, m), 3.02-3.11 (1H, m), 3.23 (3H, s), 3.29 (3H, s), 4.09-4.19 (1H, dm), 7.08 (2H, d, J=8.6 Hz), 7.64 (2H, d, J=9.0 Hz), 7.77-7.81 (1H, m), 7.94-8.02 (2H, m), 8.79 (1H, d, J=7.8 Hz)

ESI-MS (m/e): 459 [M+H]$^+$

Example 69

6-[4-(3-piperidin-1-ylpropoxy)-phenyl-pyrido[3,4-d][1,2,4]triazolo[4,3-b]pyridazine Production of 1-(4-methoxyphenyl)-3H-pyrido[3,4-d]pyridazin-4-on 7.51 ml (150.0 mmol) of hydrazine was added to an ethanol solution (200 ml) of 12.86 g (50.0 mmol) of 4-(4-methoxyphenyl)nicotinic acid obtained according to the method described in Bioorganic & Medicinal Chemistry, Vol. 10, pp. 2461-2470, (2002), and the reaction liquid was stirred at 60° C. for 4 hours. The reaction liquid was concentrated under reduced pressure, and the resulting solid was washed with diethyl ether to obtain 9.32 g (yield: 74%) of 1-(4-methoxyphenyl)-3H-pyrido[3,4-d]pyridazin-4-on as a white solid.

Production of 4-chloro-1-(4-methoxyphenyl)-pyrido[3,4-d]pyridazine

With cooling with ice, 2.5 ml of phosphorus oxychloride was added to 2.53 g (10.0 mmol) of 1-(4-methoxyphenyl)-3H-pyrido[3,4-d]pyridazin-4-on, and the reaction liquid was stirred under reflux for 6 hours. Water was added to the reaction liquid, extracted with chloroform, and the organic layer was washed with saturated saline water. This was dried with anhydrous sodium chloride, and concentrated under reduced pressure to obtain 2.50 g (yield: 92%) of 4-chloro-1-(4-methoxyphenyl)-pyrido[3,4-d]pyridazine as a brown solid.

Production of 6-(4-methoxyphenyl)-pyrido[3,4-d][1,2,4]triazolo[4,3-b]pyridazine 240 mg (4.0 mmol) of formohydrazide and 551 mg (4.0 mmol) of triethylamine hydrochloride were added to a xylene solution (10 ml) of 543 mg (2.0 mmol) of 4-chloro-1-(4-methoxyphenyl)-pyrido[3,4-d]pyridazine, and then stirred under reflux for 2 hours. Water was added to the reaction liquid, extracted with chloroform, and the organic layer was washed with saturated saline water. This was dried with anhydrous sodium sulfate, and then concentrated under reduced pressure to obtain 417 mg of a crude product of 6-(4-methoxyphenyl)-pyrido[3,4-d][1,2,4]triazolo[4,3-b]pyridazine.

Production of 4-(pyrido[3,4-d][1,2,4]triazolo[4,3-b]pyridazin-6-yl)-phenol 4.0 ml (4.0 mmol) of a dichloromethane solution of 1 M boron tribromide was added to a chloroform solution (10 ml) of 417 mg of 6-(4-methoxyphenyl)-pyrido[3,4-d][1,2,4]triazolo[4,3-b]pyridazine, and then stirred overnight at room temperature. Water was added to the reaction liquid, extracted with chloroform, and the organic layer was washed with saturated saline water. This was dried with anhydrous sodium sulfate, and concentrated under reduced pressure to obtain 421 mg of 4-(pyrido[3,4-d][1,2,4]triazolo[4,3-b]pyridazin-6-yl)-phenol.

Production of the Entitled Compound 115 mg (0.58 mmol) of 1-(3-chloropropyl)piperidine hydrochloride and 158 mg (1.14 mmol) of potassium carbonate were added to 101 mg (0.38 mmol) of 4-(pyrido[3,4-d][1,2,4]triazolo[4,3-b]pyridazin-6-yl)-phenol, and stirred at 80° C. for 2 hours.

The reaction liquid was concentrated under reduced pressure, and the resulting residue was purified through silica gel column chromatography (chloroform/methanol=10/1) to obtain 90 mg (yield: 59%) of the entitled compound as a pale yellow solid.

$^1$HNMR (CDCl$_3$) δ: 1.47 (2H, d, J=5.1 Hz), 1.59-1.64 (4H, m), 2.02-2.09 (2H, m), 2.36-2.54 (6H, m), 4.14 (2H, t, J=6.5 Hz), 7.13 (2H, d, J=8.6 Hz), 7.63 (2H, d, J=8.6 Hz), 7.82 (1H, t, J=3.1 Hz), 9.02 (1H, d, J=5.5 Hz), 9.12 (1H, s), 10.11 (1H, s)

ESI-MS (m/e): 389 [M+H]$^+$

Example 70

6-[4-(3-pyrrolidin-1-ylpropoxy)-phenyl]-pyrido[3,4-d][1,2,4]triazolo[4,3-b]pyridazine The compound of Example 70 was obtained as a pale yellow solid in the same manner as in Example 69 or according to a method similar to it or according to a combination of the method with an ordinary method, but using 1-(3-chloropropyl)pyrrolidine hydrochloride in place of 1-(3-chloropropyl)piperidine hydrochloride.

$^1$HNMR (CDCl$_3$) δ: 1.80-1.84 (4H, m), 2.05-2.12 (2H, m), 2.57 (4H, s), 2.68 (2H, t, J=7.4 Hz), 4.16 (2H, t, J=6.5 Hz), 7.14 (2H, d, J=9.0 Hz), 7.63 (2H, d, J=9.0 Hz), 7.81 (1H, dd, J=5.5, 0.8 Hz), 9.02 (1H, d, J=5.5 Hz), 9.12 (1H, s), 10.12 (1H, d, J=0.8 Hz) ESI-MS (m/e): 375 [M+H]$^+$

Example 71

6-[4-{3-[(3S)-3-methylpiperidin-1-yl]propoxy}-phenyl]-pyrido[3,4-d][1,2,4]triazolo[4,3-b]pyridazine The compound of Example 71 was obtained as a pale yellow solid in the same manner as in Example 22 or according to a method similar to it or according to a combination of the method with an ordinary method, but using (3S)-1-(3-chloropropyl)-3-methylpiperidine hydrochloride in place of 1-(3-chloropropyl)piperidine hydrochloride.

$^1$HNMR (CDCl$_3$) δ: 0.89 (3H, d, J=6.3 Hz), 1.53-1.78 (5H, m), 1.80-1.94 (2H, mz), 2.02-2.09 (2H, m), 2.53 (2H, t, J=7.2 Hz), 2.83-2.94 (2H, m), 4.15 (2H, d, J=6.7 Hz), 7.14 (2H, t, J=5.7 Hz), 7.63 (2H, d, J=8.6 Hz), 7.82 (1H, dd, J=5.5, 0.8 Hz), 10.11 (1H, s), 9.12 (1H, s), 9.02 (1H, d, J=5.5 Hz)
ESI-MS (m/e): 403 [M+H]$^+$

Example 72

3-Methyl-6-[4-(3-piperidin-1-ylpropoxy)-phenyl]-pyrido[3,4-d][1,2,4]triazolo[4,3-b]pyridazine The compound of Example 72 was obtained as a white solid in the same manner as in Example 69 or according to a method similar to it or according to a combination of the method with an ordinary method, but using 4-chloro-1-(4-methoxyphenyl)-pyrido[3,4-d]pyridazine obtained in Example 69 and acetohydrazide in place of formylhydrazide.

$^1$HNMR (CDCl$_3$) δ: 1.41-1.51 (2H, m), 1.56-1.64 (4H, m), 1.85 (2H, br), 2.02-2.09 (2H, m), 2.36-2.54 (3H, m), 2.88 (3H, s), 4.14 (2H, t, J=6.5 Hz), 7.13 (2H, d, J=9.0 Hz), 7.63 (2H, d, J=8.6 Hz), 7.78 (1H, t, J=3.3 Hz), 8.98 (1H, d, J=5.5 Hz), 10.07 (1H, s)
ESI-MS (m/e): 403 [M+H]$^+$

Example 73

3-Methyl-6-[4-(3-pyrrolidin-1-ylpropoxy)-phenyl]-pyrido[3,4-d][1,2,4]triazolo[4,3-b]pyridazine The compound of Example 73 was obtained as a pale yellow solid in the same manner as in Example 70 or according to a method similar to it or according to a combination of the method with an ordinary method, but using 4-chloro-1-(4-methoxyphenyl)-pyrido[3,4-d]pyridazine obtained in Example 69 and acetohydrazide in place of formylhydrazide.

$^1$HNMR (CDCl$_3$) δ: 1.78-1.86 (5H, m), 2.05-2.12 (2H, m), 2.57 (4H, br), 2.68 (2H, t, J=7.2 Hz), 2.86 (3H, s), 4.16 (2H, t, J=6.3 Hz), 7.13 (2H, d, J=8.6 Hz), 7.63 (2H, d, J=9.0 Hz), 7.78 (1H, dd, J=5.5, 0.8 Hz), 8.98 (1H, d, J=5.5 Hz), 10.08 (1H, d, J=0.8 Hz)
ESI-MS (m/e): 389 [M+H]$^+$

Example 74

3-Methyl-6-(4-{3-[(3S)-3-methylpiperidin-1-yl]propoxy}-phenyl]-pyrido[3,4-d][1,2,4]triazolo[4,3-b]pyridazine The compound of Example 74 was obtained as a pale yellow solid in the same manner as in Example 71 or according to a method similar to it or according to a combination of the method with an ordinary method, but using 4-chloro-1-(4-methoxyphenyl)-pyrido[3,4-d]pyridazine obtained in Example 69 and acetohydrazide in place of formylhydrazide.

$^1$HNMR (CDCl$_3$) δ: 0.89 (6H, d, J=6.7 Hz), 1.56-1.90 (7H, m), 2.03-2.09 (2H, m), 2.53 (2H, t, J=7.4 Hz), 2.86 (3H, s), 2.83-2.94 (2H, m), 4.08-4.16 (2H, m), 7.13 (2H, d, J=8.6 Hz), 7.63 (2H, d, J=8.6 Hz), 7.78 (1H, d, J=5.5 Hz), 8.98 (1H, d, J=5.5 Hz), 10.08 (1H, s)
ESI-MS (m/e): 417 [M+H]$^+$

Example 75

6-(4-{3-[(2R)-2-methylpyrrolidin-1-yl]propoxy}-phenyl]-pyrido[3,4-d][1,2,4]triazolo[4,3-b]pyridazine The compound of Example 75 was obtained as a pale yellow solid in the same manner as in Example 69 or according to a method similar to it or according to a combination of the method with an ordinary method, but using (2R)-1-(3-chloropropyl)-2-methylpyrrolidine hydrochloride in place of 1-(3-chloropropyl)piperidine hydrochloride.

$^1$HNMR (CDCl$_3$) δ: 1.12 (3H, d, J=6.3 Hz), 1.40-2.36 (10H, m), 3.21 (1H, t, J=7.4 Hz), 4.16 (2H, t, J=6.3 Hz), 7.14 (2H, d, J=8.6 Hz), 7.63 (2H, d, J=8.6 Hz), 7.82 (1H, d, J=5.5 Hz), 9.03 (1H, d, J=5.5 Hz), 9.12 (1H, s), 10.11 (1H, s)
ESI-MS (m/e): 389 [M+H]$^+$

Example 76

3-Methyl-6-(4-{3-[(2R)-2-methylpyrrolidin-1-yl]propoxy}-phenyl]-pyrido[3,4-d][2,4]triazolo[4,3-b]pyridazine The compound of Example 76 was obtained as a pale yellow solid in the same manner as in Example 72 or according to a method similar to it or according to a combination of the method with an ordinary method, but using (2R)-1-(3-chloropropyl)-3-methylpiperidine hydrochloride in place of 1-(3-chloropropyl)piperidine hydrochloride.

$^1$HNMR (CDCl$_3$) δ: 1.10 (3H, dd, J=13.9, 6.1 Hz), 1.40-2.34 (10H, m), 2.86 (3H, s), 3.21 (1H, t, J=7.8 Hz), 4.15 (2H, q, J=7.3 Hz), 7.14 (2H, d, J=8.6 Hz), 7.63 (2H, d, J=8.2 Hz), 7.78 (1H, d, J=5.1 Hz), 8.98 (1H, d, J=5.9 Hz), 10.07 (1H, s).
ESI-MS (m/e): 403 [M+H]$^+$

Example 77

6-[4-(1-Isopropylpiperidin-4-yloxy)phenyl]pyrido[3,4-d][1,2,4]triazolo[4,3-b]pyridazine The compound of Example 77 was obtained as a white solid in the same manner as in Example 2 and Example 69 or according to a method similar to it or according to a combination of the method with an ordinary method, but using acetone in place of cyclopentanone.

$^1$HNMR (CDCl$_3$) δ: 1.09 (6H, d, J=6.3 Hz), 1.91 (2H, m), 2.09 (2H, m), 2.46 (2H, m), 2.76-2.84 (3H, m), 4.46 (1H, m), 7.13 (2H, d, J=8.6 Hz), 7.63 (2H, d, J=8.6 Hz), 7.83 (1H, d, J=5.5 Hz), 9.03 (1H, d, J=5.5 Hz), 9.12 (1H, s), 10.11 (1H, s)

ESI-MS (m/e): 389 [M+H]$^+$

Example 78

6-[4-(1-Cyclobutylpiperidin-4-yloxy)phenyl]pyrido[3,4-d][1,2,4]triazolo[4,3-b]pyridazine The compound of Example 78 was obtained as a white solid in the same manner as in Example 2 and Example 69 or according to a method similar to it or according to a combination of the method with an ordinary method, but using cyclobutanone in place of cyclopentanone.

$^1$HNMR (CDCl$_3$) δ: 1.60-2.30 (1H, m), 2.60-2.80 (4H, m), 4.48 (1H, m), 7.14 (2H, d, J=7.8 Hz), 7.63 (2H, d, J=7.8 Hz), 7.83 (1H, d, J=5.5 Hz), 9.02 (1H, d, J=5.5 Hz), 9.12 (1H, s), 10.12 (1H, s)

ESI-MS (m/e): 401 [M+H]$^+$

Example 79

6-[4-(1-Cyclopentylpiperidin-4-yloxy)phenyl]pyrido[3,4-d][1,2,4]triazolo[4,3-b]pyridazine The compound of Example 79 was obtained as a white solid in the same manner as in Example 2 and Example 69 or according to a method similar to it or according to a combination of the method with an ordinary method, but using 4-chloro-1-(4-methoxyphenyl)-pyrido[3,4-d]pyridazine obtained in Example 69.

$^1$HNMR (CDCl$_3$) δ: 1.44-1.72 (7H, m), 1.80-2.20 (5H, m), 2.39 (2H, m), 2.45-2.58 (1H, m), 2.85 (2H, m), 4.48 (1H, s), 7.13 (2H, d, J=8.6 Hz), 7.62 (2H, d, J=8.6 Hz), 7.83 (1H, d, J=5.5 Hz), 9.03 (1H, d, J=5.5 Hz), 9.12 (1H, s), 10.12 (1H, s)

ESI-MS (m/e): 415 [M+H]$^+$

Example 80

6-[4-(1-Isopropylpiperidin-4-yloxy)phenyl]-3-methylpyrido[3,4-d][1,2,4]triazolo[4,3-b]pyridazine The compound of Example 80 was obtained as a white solid in the same manner as in Example 2 and Example 77 or according to a method similar to it or according to a combination of the method with an ordinary method, but using 4-chloro-1-(4-methoxyphenyl)-pyrido[3,4-d]pyridazine obtained in Example 69 and acetohydrazide in place of formylhydrazide.

$^1$HNMR (CDCl$_3$) δ: 1.10 (6H, d, J=6.3 Hz), 1.91 (2H, m), 2.10 (2H, m), 2.47 (2H, m), 2.82 (3H, m), 2.86 (3H, s), 4.46 (1H, s), 7.13 (2H, d, J=8.6 Hz), 7.63 (2H, d, J=8.6 Hz), 7.79 (1H, d, J=5.5 Hz), 8.98 (1H, d, J=5.9 Hz), 10.08 (1H, s)

ESI-MS (m/e): 403 [M+H]$^+$

Example 81

6-[4-(1-Cyclobutylpiperidin-4-yloxy)phenyl]-3-methylpyrido[3,4-d][1,2,4]triazolo[4,3-b]pyridazine The compound of Example 81 was obtained as a pale yellow solid in the same manner as in Example 2 and Example 78 or according to a method similar to it or according to a combination of the method with an ordinary method, but using 4-chloro-1-(4-methoxyphenyl)-pyrido[3,4-d]pyridazine obtained in Example 69 and acetohydrazide in place of formylhydrazide.

$^1$HNMR (CDCl$_3$) δ: 1.60-2.30 (1H, m), 2.59-2.79 (4H, m), 2.86 (3H, s), 4.48 (1H, s), 7.13 (2H, d, J=8.6 Hz), 7.63 (2H, d, J=8.6 Hz), 7.79 (1H, d, J=5.5 Hz), 8.98 (1H, d, J=5.5 Hz), 10.07 (1H, s)

ESI-MS (m/e): 415 [M+H]$^+$

Example 82

6-[4-(1-Cyclopentylpiperidin-4-yloxy)phenyl]-3-methylpyrido[3,4-d][1,2,4]triazolo[4,3-b]pyridazine The compound of Example 82 was obtained as a pale yellow solid in the same manner as in Example 2 and Example 79 or according to a method similar to it or according to a combination of the method with an ordinary method, but using 4-chloro-1-(4-methoxyphenyl)-pyrido[3,4-d]pyridazine obtained in Example 79 and acetohydrazide in place of formylhydrazide.

$^1$HNMR (CDCl$_3$) δ: 1.44-1.72 (7H, m), 1.80-2.20 (5H, m), 2.39 (2H, m), 2.45-2.58 (1H, m), 2.85 (2H, m), 2.86 (3H, s), 4.47 (1H, m), 7.13 (2H, d, J=8.6 Hz), 7.63 (2H, d, J=8.6 Hz), 7.79 (1H, d, J=5.5 Hz), 8.98 (1H, d, J=5.5 Hz), 10.07 (1H, s)

ESI-MS (m/e): 429 [M+H]$^+$

Example 83

3-Methyl-6-[4-(3-pyrrolidin-1-ylpropoxy)-phenyl-pyrido[3,2-d][1,2,4]triazolo[4,3-b]pyridazine The compound of Example 83 was obtained as a pale yellow solid in the same manner as in Example 30 or according to a method similar to it or according to a combination of the method with an ordinary method, but using 1-(3-chloropropyl)pyrrolidine hydrochloride in place of 1-(3-chloropropyl)piperidine hydrochloride.

$^1$HNMR (CDCl$_3$) δ: 1.81 (4H, s), 2.07 (2H, t, J=7.2 Hz), 2.56 (4H, s), 2.66 (2H, t, J=7.2 Hz), 2.88 (3H, s), 4.15 (2H, t, J=6.3 Hz), 7.09 (2H, d, J=9.0 Hz), 7.81 (1H, q, J=4.2 Hz), 8.01 (2H, d, J=8.6 Hz), 9.00 (1H, d, J=8.2 Hz), 9.11 (1H, d, J=3.1 Hz)

ESI-MS (n/e): 389 [M+H]$^+$

Example 84

3-Methyl-6-[4-(3-pyrrolidin-1-ylpropoxy)-phenyl]-pyrido[2,3-d][1,2,4]triazolo[4,3-b]pyridazine The compound of Example 84 was obtained as a pale yellow solid in the same manner as in Example 31 or according to a method similar to it or according to a combination of the method with an ordinary method, but using 1-(3-chloropropyl)pyrrolidine hydrochloride in place of 1-(3-chloropropyl)piperidine hydrochloride.

$^1$HNMR (CDCl$_3$) δ: 1.81 (4H, d, J=14.5 Hz), 2.09 (2H, t, J=7.4 Hz), 2.58 (4H, s), 2.69 (2H, t, J=7.4 Hz), 2.87 (3H, s), 4.16 (2H, t, J=6.3 Hz), 7.12 (2H, d, J=8.6 Hz), 7.67 (1H, q, J=4.3 Hz), 7.60 (2H, d, J=8.6 Hz), 8.28 (1H, d, J=8.2 Hz), 9.20 (1H, d, J=3.1 Hz)

ESI-MS (m/e): 389 [M+H]$^+$

Example 85

3-Methyl-6-(4-{3-[(3S)-3-methylpiperidin-1-yl]propoxy}-phenyl]-pyrido[3,2-d][1,2,4]triazolo[4,3-b]pyridazine The compound of Example 85 was obtained as a pale yellow solid in the same manner as in Example 30 or according to a method similar to it or according to a combination of the method with an ordinary method, but using (3S)-1-(3-chloropropyl)-3-methylpyrrolidine hydrochloride in place of 1-(3-chloropropyl)piperidine hydrochloride.

$^1$HNMR (CDCl$_3$) δ: 0.88 (3H, d, J=6.7 Hz), 1.55-1.89 (7H, m), 2.01-2.07 (2H, m), 2.51 (2H, t, J=7.4 Hz), 2.87 (3H, s), 2.80-2.90 (2H, m), 4.13 (2H, t, J=6.3 Hz), 7.09 (2H, d, J=8.6 Hz), 7.81 (1H, q, J=4.2 Hz), 8.01 (2H, d, J=8.6 Hz), 9.00 (1H, dd, J=8.2, 1.6 Hz), 9.11 (1H, q, J=2.0 Hz)

ESI-MS (m/e): 417 [M+H]$^+$

Example 86

3-Methyl-6-(4-{3-[(3S)-3-methylpiperidin-1-yl]propoxy}-phenyl]-pyrido[2,3-d][1,2,4]triazolo[4,3-b]pyridazine The compound of Example 86 was obtained as a pale yellow solid in the same manner as in Example 31 or according to a method similar to it or according to a combination of the method with an ordinary method, but using (3S)-1-(3-chloropropyl)-3-methylpyrrolidine hydrochloride in place of 1-(3-chloropropyl)piperidine hydrochloride.

$^1$HNMR (CDCl$_3$) δ: 0.89 (3H, d, J=6.3 Hz), 1.59-1.88 (7H, m), 2.05 (2H, q, J=7.0 Hz), 2.53 (2H, t, J=7.4 Hz), 2.87 (3H, s), 2.80-2.90 (2H, m), 4.14 (2H, t, J=6.3 Hz), 7.60 (2H, d, J=8.6 Hz), 7.12 (2H, d, J=8.6 Hz), 7.67 (1H, q, J=4.3 Hz), 8.28 (1H, d, J=8.2 Hz), 9.20 (1H, d, J=2.7 Hz)

ESI-MS (m/e): 417 [M+H]$^+$

Example 87

3-Methyl-6-(4-{3-[(2R)-3-methylpyrrolidin-1-yl]propoxy}-phenyl]-pyrido[3,2-d][1,2,4]triazolo[4,3-b]pyridazine The compound of Example 87 was obtained as a white solid in the same manner as in Example 30 or according to a method similar to it or according to a combination of the method with an ordinary method, but using (2R)-1-(3-chloropropyl)-2-methylpyrrolidine hydrochloride in place of 1-(3-chloropropyl)piperidine hydrochloride.

$^1$HNMR (CDCl$_3$) δ: 1.12 (3H, d, J=5.9 Hz), 1.39-2.53 (9H, m), 2.89 (3H, s), 3.02 (1H, dd, J=20.0, 7.8 Hz), 3.21 (1H, t, J=7.6 Hz), 4.11-4.16 (2H, m), 7.10 (2H, d, J=9.0 Hz), 7.81 (1H, q, J=4.2 Hz), 8.02 (2H, d, J=9.0 Hz), 9.00 (1H, dd, J=8.2, 1.6 Hz), 9.11 (1H, q, J=2.1 Hz)

ESI-MS (m/e): 403 [M+H]$^+$

Example 88

3-Methyl-6-(4-{3-[(2R)-3-methylpyrrolidin-1-yl]propoxy}-phenyl]-pyrido[2,3-d][1,2,4]triazolo[4,3-b]pyridazine The compound of Example 88 was obtained as a white solid in the same manner as in Example 30 or according to a method similar to it or according to a combination of the method with an ordinary method, but using (2R)-1-(3-chloropropyl)-2-methylpyrrolidine hydrochloride in place of 1-(3-chloropropyl)piperidine hydrochloride.

$^1$HNMR (CDCl$_3$) δ: 1.12 (3H, d, J=5.9 Hz), 1.42-2.43 (9H, m), 2.87 (3H, s), 3.03 (1H, dd, J=19.8, 8.0 Hz), 3.21 (1H, t, J=7.4 Hz), 4.16 (2H, t, J=6.3 Hz), 7.13 (2H, d, J=8.6 Hz), 7.61 (2H, d, J=8.6 Hz), 7.67 (1H, q, J=4.2 Hz), 8.28 (1H, d, J=7.8 Hz), 9.20 (1H, d, J=3.5 Hz)

ESI-MS (m/e): 403 [M+H]$^+$

Example 89

6-[4-(1-Isopropylpiperidin-4-yloxy)phenyl]-3-methylpyrido[3,2-d][1,2,4]triazolo[4,3-b]pyridazine The compound of Example 89 was obtained as a pale yellow solid in the same manner as in Example 2 and Example 77 or according to a method similar to it or according to a combination of the method with an ordinary method, but using 4-chloro-1-(4-methoxyphenyl)-pyrido[3,4-d]pyridazine obtained in Example 22 and acetohydrazide in place of formylhydrazide.

$^1$HNMR (CDCl$_3$) δ: 1.11 (6H, d, J=6.3 Hz), 1.93 (2H, br), 2.12 (2H, br), 2.49 (2H, br), 2.76-2.90 (3H, m), 2.88 (3H, s), 4.47 (1H, br), 7.09 (2H, d, J=9.0 Hz), 7.82 (1H, q, J=4.2 Hz), 8.02 (2H, d, J=9.0 Hz), 9.00 (1H, t, J=3.9 Hz), 9.11 (1H, d, J=2.7 Hz)

ESI-MS (m/e): 403 [M+H]$^+$

Example 90

6-[4-(1-Isopropylpiperidin-4-yloxy)phenyl]-3-methylpyrido[2,3-d][1,2,4]triazolo[4,3-b]pyridazine The compound of Example 90 was obtained as a pale yellow solid in the same manner as in Example 2 and Example 77 or according to a method similar to it or according to a combination of the method with an ordinary method, but using 8-chloro-5-(4-methoxyphenyl)-pyrido[2,3-d]pyridazine obtained in Example 22 and acetohydrazide in place of formylhydrazide.

$^1$HNMR (CDCl$_3$) δ: 1.10 (6H, d, J=6.3 Hz), 1.84-1.95 (2H, m), 2.04-2.14 (2H, m), 2.43-2.51 (2H, m), 2.77-2.89 (3H, m), 2.87 (3H, s), 4.45 (1H, br), 7.12 (2H, d, J=8.6 Hz), 7.60 (2H, d, J=8.6 Hz), 7.67 (1H, q, J=4.3 Hz), 8.29 (1H, dd, J=8.4, 1.4 Hz), 9.20 (1H, d, J=3.1 Hz)

ESI-MS (m/e): 403 [M+H]$^+$

Example 91

6-[4-(1-Cyclobutylpiperidin-4-yloxy)phenyl]-3-methylpyrido[3,2-d][1,2,4]triazolo[4,3-b]pyridazine The compound of Example 91 was obtained as a pale yellow solid in the same manner as in Example 2 and Example 78 or according to a method similar to it or according to a combination of the method with an ordinary method, but using 4-chloro-1-(4-methoxyphenyl)-pyrido[3,4-d]pyridazine obtained in Example 22 and acetohydrazide in place of formylhydrazide.

$^1$HNMR (CDCl$_3$) δ: 1.59-2.27 (12H, m), 2.65 (2H, br), 2.73-2.82 (1H, m), 2.88 (3H, s), 4.47 (1H, br), 7.08 (2H, d, J=7.4 Hz), 7.81 (1H, s), 8.01 (2H, d, J=8.2 Hz), 9.00 (1H, d, J=7.8 Hz), 9.11 (1H, s)

ESI-MS (m/e): 415 [M+H]$^+$

Example 92

6-[4-(1-Cyclobutylpiperidin-4-yloxy)phenyl]-3-methylpyrido[2,3-d][1,2,4]triazolo[4,3-b]pyridazine The compound of Example 92 was obtained as a pale yellow solid in the same manner as in Example 2 and Example 78 or according to a method similar to it or according to a combination of the method with an ordinary method, but using 8-chloro-5-(4-methoxyphenyl)-pyrido[2,3-d]pyridazine obtained in Example 22 and acetohydrazide in place of formylhydrazide.

$^1$HNMR (CDCl$_3$) δ: 1.65-2.31 (12H, m), 2.67 (2H, br), 2.75-2.82 (1H, m), 2.87 (3H, s), 4.49 (1H, s), 7.12 (2H, d, J=9.0 Hz), 7.60 (2H, d, J=8.6 Hz), 7.67 (1H, q, J=4.2 Hz), 8.29 (1H, dd, J=8.2, 1.6 Hz), 9.20 (1H, d, J=3.1 Hz)

ESI-MS (m/e): 415 [M+H]$^+$

Example 93

6-[4-(1-Cyclopentylpiperidin-4-yloxy)phenyl]-3-methylpyrido[3,2-d][1,2,4]triazolo[4,3-b]pyridazine The compound of Example 93 was obtained as a pale yellow solid in the same manner as in Example 2 and Example 79 or according to a method similar to it or according to a combination of the method with an ordinary method, but using 4-chloro-1-(4-methoxyphenyl)-pyrido[3,4-d]pyridazine obtained in Example 22 and acetohydrazide in place of formylhydrazide.

$^1$HNMR (CDCl$_3$) δ: 1.38-2.16 (12H, m), 2.88 (2H, br), 2.50-2.61 (1H, m), 2.84 (2H, br), 2.88 (3H, s), 4.46 (1H, br), 7.09 (2H, d, J=8.2 Hz), 7.82 (1H, dd, J=7.8, 4.7 Hz), 8.02 (2H, d, J=8.2 Hz), 9.00 (1H, d, J=7.8 Hz), 9.11 (1H, d, J=3.1 Hz)

ESI-MS (m/e): 429 [M+H]$^+$

Example 94

6-[4-(1-Cyclopentylpiperidin-4-yloxy)phenyl]-3-methylpyrido[2,3-d][1,2,4]triazolo[4,3-b]pyridazine The compound of Example 94 was obtained as a pale yellow solid in the same manner as in Example 2 and Example 79 or according to a method similar to it or according to a combination of the method with an ordinary method, but using 8-chloro-5-(4-methoxyphenyl)-pyrido[2,3-d]pyridazine obtained in Example 22 and acetohydrazide in place of formylhydrazide.

$^1$HNMR (CDCl$_3$) δ: 1.37-2.14 (12H, m), 2.40 (2H, br), 2.50-2.60 (1H, m), 2.78-2.88 (2H, m), 2.40 (3H, s), 4.47 (1H, br), 7.12 (2H, d, J=9.0 Hz), 7.60 (2H, d, J=8.6 Hz), 7.67 (1H, q, J=4.3 Hz), 8.29 (1H, t, J=4.9 Hz), 9.20 (1H, d, J=3.1 Hz)

ESI-MS (m/e): 429 [M+H]$^+$

Example 95

6-[4-(1-Isopropylpiperidin-4-yloxy)phenyl]pyrido[3,2-d][1,2,4]triazolo[4,3-b]pyridazine The compound of Example 95 was obtained as a pale yellow solid in the same manner as in Example 2 and Example 77 or according to a method similar to it or according to a combination of the method with an ordinary method, but using 4-chloro-1-(4-methoxyphenyl)-pyrido[3,4-d]pyridazine obtained in Example 22.

$^1$HNMR (CDCl$_3$) δ: 1.09 (6H, d, J=6.7 Hz), 1.85-1.95 (2H, m), 2.05-2.15 (2H, m), 2.40-2.50 (2H, m), 2.75-2.85 (3H, m), 4.45 (1H, br), 7.09 (2H, d, J=9.0 Hz), 7.85 (1H, q, J=4.2 Hz), 8.00 (2H, d, J=8.6 Hz), 9.04 (1H, dd, J=8.2, 1.6 Hz), 9.11 (1H, s), 9.15 (1H, t, J=2.2 Hz)

ESI-MS (m/e): 389 [M+H]$^+$

Example 96

6-[4-(1-Isopropylpiperidin-4-yloxy)phenyl]pyrido[2,3-d][1,2,4]triazolo[4,3-b]pyridazine The compound of Example 96 was obtained as a pale yellow solid in the same manner as in Example 2 and Example 79 or according to a method similar to it or according to a combination of the method with an ordinary method, but using 8-chloro-5-(4-methoxyphenyl)-pyrido[2,3-d]pyridazine obtained in Example 22.

$^1$HNMR (CDCl$_3$) δ: 1.10 (6H, d, J=6.7 Hz), 1.85-1.98 (2H, m), 2.05-2.15 (2H, m), 2.42-2.53 (2H, m), 2.78-2.90 (3H, m), 4.45 (1H, br), 7.13 (2H, d, J=8.6 Hz), 7.60 (2H, d, J=8.6 Hz), 7.72 (1H, q, J=4.3 Hz), 8.33 (1H, dd, J=8.4, 1.4 Hz), 9.14 (1H, s), 9.23 (1H, t, J=2.3 Hz)

ESI-MS (m/e): 389 [M+H]$^+$

Example 97

6-[4-(1-Cyclobutylpiperidin-4-yloxy)phenyl]pyrido[3,2-d][1,2,4]triazolo[4,3-b]pyridazine The compound of Example 97 was obtained as a pale yellow solid in the same manner as in Example 2 and Example 78 or according to a method similar to it or according to a combination of the method with an ordinary method, but using 4-chloro-1-(4-methoxyphenyl)-pyrido[3,4-d]pyridazine obtained in Example 22.

$^1$HNMR (CDCl$_3$) δ: 1.65-1.95 (6H, m), 2.00-2.12 (4H, m), 2.16-2.27 (2H, m), 2.60-2.70 (2H, m), 2.70-2.80 (1H, m), 4.48 (1H, br), 7.08 (2H, d, J=8.6 Hz), 7.85 (1H, q, J=4.2 Hz), 8.00 (2H, d, J=9.0 Hz), 9.04 (1H, dd, J=8.2, 1.6 Hz), 9.11 (1H, s), 9.15 (1H, dd, J=4.7, 1.6 Hz)

ESI-MS (m/e): 401 [M+H]$^+$

Example 98

6-[4-(1-Cyclobutylpiperidin-4-yloxy)phenyl]pyrido[2,3-d][1,2,4]triazolo[4,3-b]pyridazine The compound of Example 98 was obtained as a pale yellow solid in the same manner as in Example 2 and Example 78 or according to a method similar to it or according to a combination of the method with an ordinary method, but using 8-chloro-5-(4-methoxyphenyl)-pyrido[2,3-d]pyridazine obtained in Example 22.

$^1$HNMR (CDCl$_3$) δ: 1.65-2.00 (6H, m), 2.00-2.13 (4H, m), 2.16-2.30 (2H, m), 2.60-2.70 (2H, m), 2.72-2.80 (1H, m), 4.45 (1H, br), 7.12 (2H, d, J=8.6 Hz), 7.60 (2H, d, J=8.6 Hz), 7.71 (1H, q, J=4.3 Hz), 8.32 (1H, dd, J=8.4, 1.4 Hz), 9.13 (1H, s), 9.23 (1H, d, J=3.1 Hz)

ESI-MS (m/e): 401 [M+H]$^+$

Example 99

6-[4-(1-Cyclopentylpiperidin-4-yloxy)phenyl]pyrido[3,2-d][1,2,4]triazolo[4,3-b]pyridazine The compound of Example 99 was obtained as a pale yellow solid in the same manner as in Example 2 and Example 82 or according to a method similar to it or according to a combination of the method with an ordinary method, but using 4-chloro-1-(4-methoxyphenyl)-pyrido[3,4-d]pyridazine obtained in Example 22.

¹HNMR (CDCl₃) δ: 1.38-1.80 (3H, m), 1.83-1.98 (3H, m), 2.00-2.22 (2H, m), 2.30-2.60 (4H, m), 2.80-2.90 (3H, m), 3.00-3.04 (2H, m), 4.45 (1H, br), 7.09 (2H, d, J=8.6 Hz), 7.85 (1H, q, J=4.2 Hz), 8.00 (2H, d, J=9.0 Hz), 9.04 (1H, t, J=4.9 Hz), 9.11 (1H, s), 9.14 (1H, t, J=2.2 Hz)

ESI-MS (m/e): 415 [M+H]⁺

Example 100

6-[4-(1-Cyclopentylpiperidin-4-yloxy)phenyl]pyrido[2,3-d][1,2,4]triazolo[4,3-b]pyridazine The compound of Example 100 was obtained as a pale yellow solid in the same manner as in Example 2 and Example 87 or according to a method similar to it or according to a combination of the method with an ordinary method, but using 8-chloro-5-(4-methoxyphenyl)-pyrido[2,3-d]pyridazine obtained in Example 22.

¹HNMR (CDCl₃) δ: 1.38-1.78 (4H, m), 1.82-1.97 (4H, m), 1.97-2.22 (3H, m), 2.40 (1H, br), 2.62-2.50 (2H, m), 2.84 (2H, br), 3.02 (1H, s), 4.47 (1H, br), 7.13 (2H, d, J=8.6 Hz), 7.60 (2H, d, J=9.0 Hz), 7.71 (1H, q, J=4.3 Hz), 8.33 (1H, d, J=8.2 Hz), 9.14 (1H, s), 9.24 (1H, d, J=3.1 Hz)

ESI-MS (m/e): 415 [M+H]⁺

Example 101

6-[6-(3-Piperidin-1-ylpropoxy)pyridin-3-yl]-[1,2,4]triazolo[3,4-a]phthalazine

Production of 2-[(6-methoxypyridin-3-yl)carbonyl]benzoic acid 42.4 ml (110 mmol) of 2.59 M butyllithium was dropwise added to a tetrahydrofuran (200 ml) solution of 20.68 g (110 mmol) of 5-bromo-2-methoxypyridine at −78° C., and stirred overnight at room temperature. Aqueous 1 N hydrochloric acid solution was added to the reaction liquid, extracted with chloroform, and the organic layer was washed with saturated saline water. This was dried with anhydrous sodium sulfate, and the reaction liquid was concentrated under reduced pressure to obtain 28.0 g of a crude product of 2-[(6-methoxypyridin-3-yl)carbonyl]benzoic acid as a yellow oily substance.

Production of 4-(6-methoxypyridin-3-yl)-2H-phthalazin-1-on 24 ml (121 mmol) of hydrazine was added to an ethanol solution (200 ml) of 28.0 g of 2-[(6-methoxypyridin-3-yl)carbonyl]benzoic acid, and the reaction liquid was stirred at 60° C. for 4 hours. The reaction liquid was concentrated under reduced pressure, and the resulting solid was washed with diethyl ether to obtain 21.50 g (yield: 77%) of 4-(6-methoxypyridin-3-yl)-2H-phthalazin-1-on as a white solid.

Production of 1-chloro-4-(6-methoxypyridin-3-yl)-phthalazine

932 μl (10 mmol) of phosphorus oxychloride was added to a pyridine solution (5 ml) of 507 mg (2 mmol) of 4-(6-methoxypyridin-3-yl)-2H-phthalazin-1-on, and the reaction liquid was stirred at 120° C. for 30 minutes. This was concentrated under reduced pressure, aqueous saturated sodium hydrogencarbonate solution was added to the reaction liquid, extracted with chloroform, and the organic layer was washed with saturated saline water. This was dried with anhydrous sodium sulfate, and concentrated under reduced pressure to obtain 300 mg (yield: 55%) of 1-chloro-4-(6-methoxypyridin-3-yl)-phthalazine as a brown solid.

Production of 6-(6-methoxypyridin-3-yl)-[1,2,4]triazolo[3,4-a]phthalazine

100 μl (2 mmol) of hydrazine was added to an ethanol solution (10 ml) of 300 mg of 1-chloro-4-(6-methoxypyridin-3-yl)-phthalazine, and the reaction liquid was stirred at 60° C. for 4 hours. The reaction liquid was concentrated under reduced pressure, and formic acid (10 ml) was added to the resulting solid and stirred at 120° C. for 30 minutes. This was concentrated under reduced pressure, aqueous saturated sodium hydrogencarbonate solution was added to the reaction liquid, extracted with chloroform, and the organic layer was washed with saturated saline water. This was dried with anhydrous sodium sulfate, and concentrated under reduced pressure to obtain 141 mg (yield: 51%) of 6-(6-methoxypyridin-3-yl)-[1,2,4]triazolo[3,4-a]phthalazine as a brown solid.

Production of 5-[1,2,4]triazolo[3,4-a]phthalazin-6-ylpyridin-2-ol hydrobromide

47% hydrobromic acid was added to 141 mg of 6-(6-methoxypyridin-3-yl)-[1,2,4]triazolo[3,4-a]phthalazine, and refluxed for 4 hours. The reaction liquid was concentrated under reduced pressure, and ether was added to the resulting residue. The resulting solid was taken out through filtration to obtain 250 mg of 5-[1,2,4]triazolo[3,4-a]phthalazin-6-ylpyridin-2-ol hydrobromide as a brown solid.

Production of the Entitled Compound 38 mg (0.19 mmol) of 1-(3-chlorophenyl)-piperidin hydrochloride and 66 mg (0.48 mmol) of potassium carbonate were added to 56 mg (0.16 mmol) of 5-[1,2,4]triazolo[3,4-a]phthalazin-6-ylpyridin-2-ol, and stirred at 80° C. for 2 hours.

The reaction liquid was concentrated and the resulting residue was purified through silica gel column chromatography (chloroform/methanol=10/1) to obtain 20 mg (yield: 32%) of the entitled compound as a white solid.

¹HNMR (CDCl₃) δ: 1.40-1.55 (6H, m), 1.85 (1H, br), 2.00-2.07 (2H, m), 2.35-2.50 (5H, m), 4.15 (2H, t, J=6.7 Hz), 6.74 (1H, d, J=9.4 Hz), 7.66 (1H, dd, J=9.2, 2.5 Hz), 7.84 (1H, t, J=7.6 Hz), 8.02-7.96 (3H, m), 8.78 (1H, d, J=7.8 Hz), 9.01 (1H, s)

ESI-MS (m/e): 389 [M+H]⁺

Example 102

6-{6-[(3S)-3-piperidin-1-ylpropoxl]pyridin-3-yl]-[1,2,4]triazolo[3,4-a]phthalazine The compound of Example 102 was obtained as a white solid in the same manner as in Example 102 or according to a method similar to it or according to a combination of the method with an ordinary method, but using (3S)-1-(3-chloropropyl)-3-methylpiperidine hydrochloride in place of 1-(3-chloropropyl)piperidine hydrochloride.

¹HNMR (CDCl₃) δ: 0.77 (3H, d, J=5.9 Hz), 0.80-0.90 (1H, m), 1.40-1.75 (5H, m), 1.80-1.90 (1H, m), 2.01-2.07 (2H, m), 2.34 (2H, t, J=6.3 Hz), 2.70-2.83 (2H, m), 4.14 (2H, t, J=6.5 Hz), 6.74 (1H, d, J=9.4 Hz), 7.65 (1H, dd, J=9.2, 2.5 Hz), 7.84 (1H, t, J=7.8 Hz), 7.95-8.05 (3H, m), 8.78 (1H, d, J=7.8 Hz), 9.02 (1H, s)

ESI-MS (m/e): 403 [M+H]⁺

Reference Example 1

1-Tert-butyloxycarbonyl-4-chloro-piperidine

The compound of Reference Example 1 is obtained in the same manner as the method described in the above-mentioned literature (e.g., *Protective Groups in Organic Synthesis*, written by T. W. Green, 2nd Ed., John Wiley & Sons, 1991) or according to a method similar to it or according to a combination of the method with an ordinary method, but using 4-chloro-piperidine hydrochloride.

Pharmaceutical test examples with the compounds of Examples 1, 10, 19, 24, 30 and 69 are described below.

Pharmaceutical Test Example 1

Histamine Analogue-Binding Inhibition Test

A cDNA sequence coding for a human histamine-3 receptor [see International Laid-Open WO00/39164] was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see *Proceedings of the National Academy of Sciences of the United States of America*, Vol., 84, p. 7413 (1987)] to obtain histamine-3 receptor expression cells.

A membrane specimen prepared from the cells having expressed a histamine-3 receptor was incubated in an assay buffer (50 mM Tris buffer, 100 mM NaCl, 5 mM $MgCl_2$, pH 7.4) along with a test compound, 20 nM R-methylhistamine (histamine analogue, by Sigma), 10?M GDP (guanine nucleotide diphosphate, by Sigma), 200 pM [$^{35}S$]GTPγS (guanine nucleotide triphosphate analogue, by Amersham) and SPA resin (W heat germ agglutinin SPA beads, by Amersham) therein, on a 96-well optiplate (by Packard) at 25° C. for 3 hours, then centrifuged at 3,000 rpm, and the activity was determined with Topcount (by Packard). The non-specific binding was determined in the presence of 10 μM GTPγS (by Sigma), and the 50% inhibitory concentration ($IC_{50}$) of the test compound to the specific [$^{35}S$]GTPγS binding was calculated [see *British Journal of Pharmacology*, Vol. 135, p. 383 (2002)]. The results are shown below.

| Example No. | IC50(nM) |
|---|---|
| Example 1 | 6.8 |
| Example 10 | 1.8 |
| Example 19 | 1.4 |
| Example 24 | 10 |
| Example 30 | 0.1 |
| Example 69 | 0.23 |

As in the above, the compounds of Examples 1, 10, 19, 24, 30 and 69 strongly inhibited the binding of N-alpha-methyl-histamine (histamine analogue) to histamine-H3 receptor.

INDUSTRIAL APPLICABILITY

The invention provides novel substances having a histamine-H3 receptor antagonistic activity (activity to prevent histamine from binding to histamine-H3 receptor) or a histamine-H3 receptor inverse-agonistic activity (activity to inhibit the homeostatic activity of histamine-H3 receptor); or that is, novel substances acting as a histamine-H3 receptor agonist or antagonist in living bodies.

Nitrogen-containing condensed hetero-aromatic derivatives of formula (I) or their pharmaceutically-acceptable salts that the invention provides have a strong histamine-H3 receptor antagonistic or inverse-agonistic activity, and are useful for prevention or remedy of metabolic system diseases such as obesity, diabetes, hormone secretion disorder, hyperlipemia, gout, fatty liver; circulatory system diseases such as stenocardia, acute/congestive cardiac insufficiency, cardiac infarction, coronary arteriosclerosis, hypertension, nephropathy, electrolyte metabolism disorder; or central or peripheral nervous system diseases such as sleep disorder, various diseases accompanied by sleep disorder (e.g., idiopathic hypersomnnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, melancholia, anxiety, schizophrenia), bulimia, emotional disorder, epilepsy, delirium, dementia, attention deficit/hyperactivity disorder, memory disorder, Alzheimer's disease, Parkinson's disease, recognition disorder, motion disorder, paresthesia, dysosmia, morphine resistance, narcotic dependency, alcoholic dependency, tremor.

The invention claimed is:

1. A compound of the formula (I):

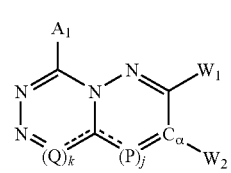

(I)

wherein:

$A_1$ represents a hydrogen atom, a group selected from a substituent group β optionally having 1 or 2 groups selected from a substituent group α, or a phenyl or heteroaryl group, which optionally have 1 or 2 groups selected from a substituent group γ;

j is 1, and the formula (III-1):

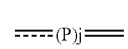

(III-1)

in the formula (I) represents a group of the formula:

wherein $A_2$ is selected from the definitions of $A_1$;

k is 0, and the formula (III-2):

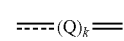

(III-2)

in the formula (I) represents a double bond;

one of $W_1$ and $W_2$ is $A_4$, wherein $A_4$ is a hydrogen atom or a lower alkyl group, and the other of $W_1$ and $W_2$ is E—O—W, or $W_1$ may be E—O—W and $A_2$—C=C—$W_2$ may together form a benzene ring or a heteroaryl ring having from 1 to 3 of the same or different hetero atoms selected from a group consisting of a nitrogen atom, a sulfur atom and an oxygen atom (the benzene ring and the heteroaryl ring may be substituted with a nitro group, a hydroxy group, a lower alkyl group, a halo-lower alkyl group, a halogen atom, a lower alkoxy group, an alkanoylamino group);

E represents a phenyl group optionally having from 1 to 3 groups selected from a substituent group δ, or a 5- or 6-membered monocyclic aromatic heterocyclic group having 1 to 3 of the same or different hetero atoms selected from a group consisting of a nitrogen atom, an oxygen atom and a sulfur atom, or represents a condensed-cyclic aromatic heterocyclic group that the monocyclic aromatic heterocyclic group forms together with an aryl group;

W represents the formula (II-1):

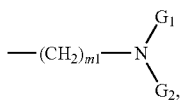

(II-1)

the formula (II-2):

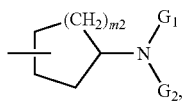

(II-2)

or the formula (II-3):

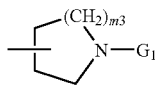

(II-3)

wherein $G_1$ and $G_2$ may be the same or different, each representing a lower alkyl group (the lower alkyl group may be further substituted with a halogen atom) or a cycloalkyl group, or $G_1$ and $G_2$ form, together with the nitrogen atom adjacent to $G_1$ and $G_2$, a 5- to 8-membered aliphatic hetero-ring (the hetero-ring may have, in the ring, 1 or 2 groups of a lower alkyl group optionally substituted with a halogen atom or a halogen atom) or a bicyclo-ring; m1 indicates an integer of from 2 to 4; m2 and m3 each indicate an integer of from 1 to 3; $(CH_2)m1$ in the formula (II-1) may be further substituted with a lower alkyl group having from 1 to 3 carbon atoms;

wherein substituent group α is selected from the group consisting of:

an amino group, a nitro group, a cyano group, a hydroxy group, a halogen atom, a lower alkylsulfonyl group, a lower alkyl group (the lower alkyl group may be substituted with a halogen atom), a lower cycloalkyl group (the lower cycloalkyl group may be substituted with a halogen atom), a lower alkoxy group (the lower alkoxy group may be substituted with a halogen atom), a lower cycloalkoxy group (the lower cycloalkoxy group may be substituted with a halogen atom), an aryloxy group, an alaryloxy group, an aryl group, a heteroaryl group, a mono-lower alkylcarbamoyl group, a di-lower alkylcarbamoyl group, a lower alkylcarboxamido group, an arylcarboxamido group, a heteroarylcarboxamido group, an alkanoyl group, and an alkylthio group;

wherein substituent group β is selected from the group consisting of:

an amino group, a lower alkylsulfonyl group, a lower alkyl group, a lower cycloalkyl group, a lower alkoxy group, a lower cycloalkoxy group, the lower alkyl group being optionally substituted with a halogen atom, a lower cycloalkyl group (the cycloalkyl group may be substituted with a halogen atom), a lower alkoxy group (the lower alkoxy group may be substituted with a halogen atom), a lower cycloalkoxy group (the lower cycloalkoxy group may be substituted with a halogen atom), a carbamoyl group, and a mono- or di-lower alkylcarbamoyl group;

wherein substituent group γ is selected from the group consisting of:

an amino group, a nitro group, a cyano group, a hydroxy group, a lower alkylsulfonyl group, a halogen atom, a lower alkyl group (the lower alkyl group may be substituted with a halogen atom), a lower cycloalkyl group (the lower alkyl group may be substituted with a halogen atom), a lower alkoxy group (the lower alkoxy group may be substituted with a halogen atom or a hydroxy group), a lower cycloalkoxy group (the lower alkyl group may be substituted with a halogen atom), an aryloxy group, an alaryloxy group, an aryl group, a heteroaryl group, a mono-lower alkylcarbamoyl group, a di-lower alkylcarbamoyl group, a lower alkylcarboxamido group, an arylcarboxamido group, a heteroarylcarboxamido group, an alkanoyl group, an alkylthio group, an alkoxycarbonylamino group, an alkylsulfonylamino group, an arylsulfonylamino group, and an alkylaminosulfonyl group or an arylaminosulfonyl group;

wherein substituent group δ is selected from the group consisting of:

a halogen atom, a nitro group, a lower alkyl group, a halo-lower alkyl group, a hydroxy group, a hydroxy-lower alkyl group, a cyclo-lower alkyl group, a lower alkenyl group, a hydroxyl group, a lower alkoxy group, a halo-lower alkoxy group, a lower alkylamino group, a di-lower alkylamino group, a lower alkylthio group, a carboxyl group, a lower alkanoyl group, and a lower alkoxycarbonyl group;

or a pharmaceutically acceptable salt thereof.

2. The compound of claim 1 wherein $A_1$ is a hydrogen atom, a lower alkyl group (wherein the lower alkyl group may be substituted with a halogen atom), a lower alkoxy group, a phenyl group, a pyridyl group, a carbamoyl group, a mono- or di-lower alkylcarbamoyl group, and $A_2$ and $A_4$ each are independently a hydrogen atom or a lower alkyl group.

3. The compound of claim 1 wherein one of $W_1$ and $W_2$ is $A_4$, and the other is E—O—W; or $W_1$ is E—O—W, and $A_2$—C=C—$W_2$ together forms a benzene ring or a heteroaryl ring having 1 or 2 nitrogen atoms in the ring.

4. The compound of claim 1 wherein E is a phenyl group, a pyridyl group, a pyrimidinyl group, a pyridazinyl group or a pyrazinyl group.

5. The compound of claim 1 wherein E is a phenyl group or a pyridyl group.

6. The compound of claim 1 wherein E is a phenyl group.

7. The compound of claim 1 wherein W is of the formula (II-1) or the formula (II-3).

8. The compound of claim 1 wherein the formula (I) is selected from the following formula (I-0), (I-2), (I-3) and (I-4):

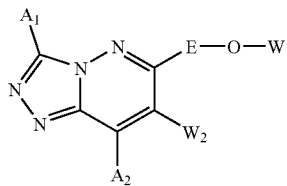
(I-0)

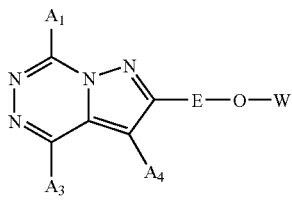
(I-1)

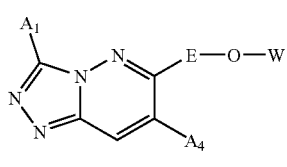
(I-2)

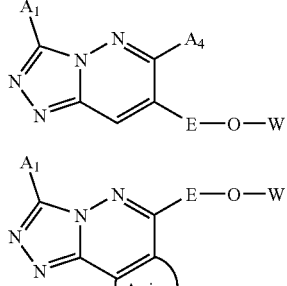
(I-3)

(I-4)

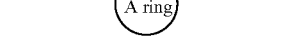

wherein:
the ring A represents a benzene ring or a heteroaryl ring having 1 or 2 nitrogen atoms in the ring (wherein the benzene ring and the heteroaryl ring is unsubstituted or substituted with a nitro group, a hydroxyl group, a lower alkyl group, a halo-lower alkyl group, a halogen atom, a lower alkoxy group, or an alkanoylamino group).

9. The compound of claim 7 wherein the ring A is a benzene ring or a pyridine ring.

10. A compound of the formula (I-0):

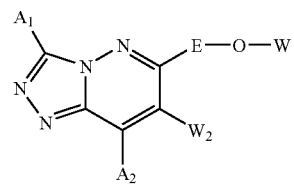
(I-0)

wherein:
$A_1$ represents a hydrogen atom, C(1-6)alkyl group optionally substituted with halogen atom, a pyridyl group, a phenyl group, a mono-C(1-6)alkylcarbamoyl group, a di-C(1-6)alkylcarbamoyl group, or a piperidin-1-yl-carbonyl group;

$A_2$ represents a hydrogen and $W_2$ represent $A_4$, or $A_2$ and $W_2$ together form a ring A, wherein ring A is selected from the group consisting of: a benzene ring, a pyridine ring, a thiophene ring, a furan ring and a pyrazine ring;

$A_4$ is selected from the definitions of $A_1$;

E represent a phenyl, a pyridyl, a pyrimidinyl or a pyridazinyl group;

W represents the formula (II-1):

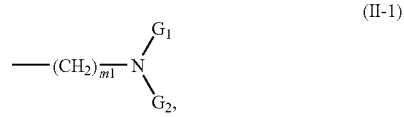
(II-1)

the formula (II-2):

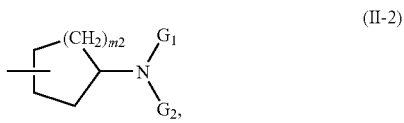
(II-2)

or the formula (II-3):

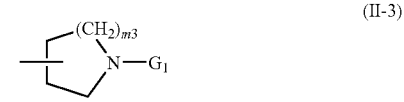
(II-3)

wherein $G_1$ and $G_2$ may be the same or different, each representing a C(1-6)alkyl group wherein the alkyl group may be further substituted with a halogen atom, or a C3 or C4 cycloalkyl group, or $G_1$ and $G_2$ form, together with the nitrogen atom adjacent to $G_1$ and $G_2$, a 5- to 8-membered aliphatic hetero-ring, wherein the hetero-ring may have, in the ring, 1 or 2 groups of a C(1-6)alkyl group optionally substituted with a halogen atom, or the hetero-ring may have, in the ring, 1 or 2 groups of a halogen atom;

m1 indicates an integer which is 2, 3 or 4;
m2 and m3 each indicate an integer which is 1, 2 or 3;
$(CH_2)m1$ in the formula (II-1) may be further substituted with an alkyl group having from 1 to 3 carbon atoms;
or a pharmaceutically acceptable salt thereof.

11. The compound of claim 10 wherein E is a phenyl or a pyridyl group.

12. The compound of claim 11 wherein E is a phenyl group.

13. The compound of claim 10 wherein $A_2$ is a hydrogen atom and $W_2$ represents $A_4$.

14. The compound of claim 10 wherein $A_2$ and $W_2$ together form the ring A.

15. The compound of claim 14 wherein the ring A is a benzene ring or a pyridine ring.

16. A compound which is selected from the group consisting of:
6-[4-(3-piperidin-1-ylpropoxy)-phenyl]-[1,2,4]triazolo[4,3-b]pyridazine, 7-methyl-6-[4-(3-piperidin-1-ylpropoxy)-phenyl]-[1,2,4]triazolo[4,3-b]pyridazine,
3-methyl-6-[4-(3-piperidin-1-ylpropoxy)-phenyl]-[1,2,4]triazolo[4,3-b]pyridazine,
6-[4-(3-piperidin-1-ylpropoxy)-phenyl]-3-trifluoromethyl-[1,2,4]triazolo[4,3-b]pyridazine,
3-tert-butyl-6-[4-(3-piperidin-1-ylpropoxy)-phenyl]-[1,2,4]triazolo[4,3-b]pyridazine,
3-phenyl-6-[4-(3-piperidin-1-ylpropoxy)-phenyl]-[1,2,4]triazolo[4,3-b]pyridazine,
6-[4-(3-piperidin-1-ylpropoxy)-phenyl]-3-(pyridin-2-yl)-[1,2,4]triazolo[4,3-b]pyridazine,
6-[4-(3-piperidin-1-ylpropoxy)-phenyl]-3-(pyridin-3-yl)-[1,2,4]triazolo[4,3-b]pyridazine,
7-methyl-3-phenyl-6-[4-(3-piperidin-1-ylpropoxy)-phenyl]-[1,2,4]triazolo[4,3-b]pyridazine,
6-methyl-7-[4-(3-piperidin-1-ylpropoxy)-phenyl]-1,2,4]triazolo[4,3-b]pyridazine,
3,6-dimethyl-7-[4-(3-piperidin-1-ylpropoxy)-phenyl]-[1,2,4]triazolo[4,3-b]pyridazine,
6-methyl-3-phenyl-[4-(3-piperidin-1-ylpropoxy)-phenyl]-[1,2,4]triazolo[4,3-b]pyridazine,
6-[4-(3-piperidin-1-ylpropoxy)-phenyl]-pyrido[3,2-d][1,2,4]triazolo[4,3-b]pyridazine,
3-phenyl-6-[4-(3-piperidin-1-ylpropoxy)-phenyl]-pyrido[2,3-d][1,2,4]triazolo[4,3-b]pyridazine,
3-phenyl-6-[6-(3-piperidin-1-ylpropoxy)-pyridin-3-ylmethoxy]-[1,2,4]triazolo[3,4-a]phthalazine,
3-phenyl-6-[4-(3-piperidin-1-ylpropoxy)-phenyl]-[1,2,4]triazolo[3,4-a]phthalazine,
6-[4-(3-piperidin-1-ylpropoxy)-phenyl]-3-(pyridin-3-yl)-[1,2,4]triazolo[3,4-a]phthalazine,
6-[4-(3-piperidin-1-ylpropoxy)-phenyl]-3-(pyridin-2-yl)-[1,2,4]triazolo[3,4-a]phthalazine,
3-phenyl-6-[4-(3-piperidin-1-ylpropoxy)-phenyl]-pyrido[3,2-d][1,2,4]triazolo[4,3-b]pyridazine,
6-[4-(3-piperidin-1-ylpropoxy)-phenyl]-pyrido[2,3-d][1,2,4]triazolo[4,3-b]pyridazine,
3-methyl-6-[4-(3-piperidin-1-ylpropoxy)-phenyl]-pyrido[3,2-d][1,2,4]triazolo[4,3-b]pyridazine,
3-methyl-6-[4-(3-piperidin-1-ylpropoxy)-phenyl]-pyrido[2,3-d][1,2,4]triazolo[4,3-b]pyridazine,
6-[4-(3-piperidin-1-ylpropoxy)-phenyl]-[1,2,4]triazolo[3,4-a]phthalazine,
3-methyl-6-[4-(3-piperidin-1-ylpropoxy)-phenyl]-[1,2,4]triazolo[3,4-a]phthalazine,
6-[4-(3-piperidin-1-ylpropoxy)-phenyl]-3-trifluoromethyl-[1,2,4]triazolo[3,4-a]phthalazine,
3-tert-butyl-6-[4-(3-piperidin-1-ylpropoxy)-phenyl]-[1,2,4]triazolo[3,4-a]phthalazine,
6-[4-(1-cyclopentyl-piperidin-4-yloxy)-phenyl]-[1,2,4]triazolo[4,3-b]pyridazine,
6-[4-(1-cyclobutyl-piperidin-4-yloxy)-phenyl]-[1,2,4]triazolo[4,3-b]pyridazine,
6-[4-(1-cyclopentyl-piperidin-4-yloxy)-phenyl]-3-methyl-[1,2,4]triazolo[4,3-b]pyridazine,
6-[4-(1-cyclopentyl-piperidin-4-yloxy)-phenyl]-7-methyl-[1,2,4]triazolo[4,3-b]pyridazine,
7-[4-(3-piperidin-1-ylpropoxy)-phenyl]-[1,2,4]triazolo[4,3-b]pyridazine,
7-[4-(1-cyclopentyl-piperidin-4-yloxy)-phenyl]-3-methyl-[1,2,4]triazolo[4,3-b]pyridazine,
7-[4-(1-cyclopentyl-piperidin-4-yloxy)-phenyl]-6-methyl-[1,2,4]triazolo[4,3-b]pyridazine,
7-[4-(1-cyclopentyl-piperidin-4-yloxy)-phenyl]-3,6-dimethyl-[1,2,4]triazolo[4,3-b]pyridazine,
7-[4-(1-cyclopentyl-piperidin-4-yloxy)-phenyl]-[1,2,4]triazolo[4,3-b]pyridazine,
7-[4-(1-cyclobutyl-piperidin-4-yloxy)-phenyl]-[1,2,4]triazolo[4,3-b]pyridazine,
6-[4-(1-cyclopentyl -piperidin-4-yloxy)-phenyl]-[1,2,4]triazolo[3,4-a]phthalazine,
6-[4-(1-cyclopentyl-piperidin-4-yloxy)-phenyl]-3-methyl-[1,2,4]triazolo[3,4-a]phthalazine,
6-[4-(3-pyrrolidin-1-ylpropoxy)-phenyl]-[1,2,4]triazolo[4,3-b]pyridazine,
3-methyl-7-[4-(3-piperidin-1-ylpropoxy)-phenyl]-[1,2,4]triazolo[4,3-b]pyridazine,
7-[4-(1-cyclobutyl-piperidin-4-yloxy)-phenyl]-3-methyl-[1,2,4]triazolo[4,3-b]pyridazine,
6-[4-(1-cyclobutyl-piperidin-4-yloxy)-phenyl]-3-methyl-[1,2,4]triazolo[4,3-b]pyridazine,
6-[4-(1-cyclobutyl-piperidin-4-yloxy)-phenyl]-[1,2,4]triazolo[3,4-a]phthalazine,
6-[4-(1-cyclobutyl-piperidin-4-yloxy)-phenyl]-7-methyl-[1,2,4]triazolo[4,3-b]pyridazine,
7-[4-(1-cyclobutyl-piperidin-4-yloxy)-phenyl]-6-methyl-[1,2,4]triazolo[4,3-b]pyridazine,
7-[4-(1-cyclobutyl-piperidin-4-yloxy)-phenyl]-3,6-dimethyl-[1,2,4]triazolo[4,3-b]pyridazine,
6-[4-(1-cyclobutyl-piperidin-4-yloxy)-phenyl]-3-methyl-[1,2,4]triazolo[3,4-a]phthalazine,
6-{4-[3-(2,6-dimethylpiperizin-1-yl)propoxy]-phenyl}-[1,2,4]triazolo[4,3-b]pyridazine,
6-{4-[3-(2,5-dimethylpyrrolidin-1-yl)propoxy]-phenyl}-[1,2,4]triazolo[4,3-b]pyridazine,
N-methyl-6-[4-(3-piperidin-1-ylpropoxy)phenyl]-[1,2,4]triazolo[4,3-b]pyridazine-3-carboxamide,
3-(piperidin-1-ylcarbonyl)-6-[4-(3-piperidin-1-ylpropoxy)phenyl]-[1,2,4]triazolo[4,3-b]pyridazine,
6-[4-(3-methylpiperidin-1-ylpropoxy)-phenyl]-[1,2,4]triazolo[4,3-b]pyridazine,
6-[4-{3-[(3S)-3-fluoropyrrolidin-1-yl]propoxy}-phenyl)-[1,2,4]triazolo[4,3-b]pyridazine,
6-{4-[3-(3-methylpiperidin-1-yl)propoxy]-phenyl}-[1,2,4]triazolo[4,3-b]pyridazine,
6-{4-[3-(4-fluoropiperidin-1-yl)propoxy]-phenyl}-[1,2,4]triazolo[4,3-b]pyridazine,
6-{4-[3-(3-fluoropiperidin-1-yl)propoxy]-phenyl}-[1,2,4]triazolo[4,3-b]pyridazine,
6-[4-{3-[(2R)-(2-methylpyrrolidin-1-yl]propoxy)-phenyl}-[1,2,4]triazolo[4,3-b]pyridazine,
6-[4-{3-[(2S )-(2-methylpyrrolidin-1-yl]propoxy)-phenyl}-[1,2,4]triazolo[4,3-b]pyridazine,
N,N-dimethyl-6-[4-{3-[(2R)-2-methylpyrrolidin-1-yl]propoxy)-phenyl}-[1,2,4]triazolo[3,4-a]phthalazine-3-carboxamide,
6-[4-(3-piperidin-1-ylpropoxy)-phenyl]-pyrido[3,4-d][1,2,4]triazolo[4,3-b]pyridazine,
6-[4-(3-pyrrolidin-1-ylpropoxy)-phenyl]-pyrido[3,4-d][1,2,4]triazolo[4,3-b]pyridazine,
6-[4-{3-[(3S)-3-methylpiperidin-1-yl]propoxy}-phenyl]-pyrido[3,4-d][1,2,4]triazolo[4,3-b]pyridazine,
3-methyl-6-[4-(3-piperidin-1-ylpropoxy)-phenyl]-pyrido[3,4-d][1,2,4]triazolo[4,3-b]pyridazine,
3-methyl-6-[4-(3-pyrrolidin-1-ylpropoxy)-phenyl]-pyrido[3,4-d][1,2,4]triazolo[4,3-b]pyridazine,
3-methyl-6-[4-{3-[(3S)-3-methylpiperidin-1-yl]propoxy}-phenyl]-pyrido[3,4-d][1,2,4]triazolo[4,3-b]pyridazine,
6-[4-{3-[(2R)-2-methylpyrrolidin-1-yl]propoxy}-phenyl]-pyrido[3,4-d][1,2,4]triazolo[4,3-b]pyridazine, 3-methyl-6-[4-{3-[(2R)-2-methylpyrrolidin-1-yl]propoxy}-phenyl]-pyrido[3,4-d][1,2,4]triazolo[4,3-b]pyridazine,
6-[4-(1-isopropylpiperidin-4-yloxy)phenyl]pyrido[3,4-d][1,2,4]triazolo[4,3-b]pyridazine,
6-[4-(1-cyclobutylpiperidin-4-yloxy)phenyl]pyrido[3,4-d][1,2,4]triazolo[4,3-b]pyridazine,
6-[4-(1-cyclopentylpiperidin-4-yloxy)phenyl]pyrido[3,4-d][1,2,4]triazolo[4,3-b]pyridazine,
6-[4-(1-isopropylpiperidin-4-yloxy)phenyl]-3-methylpyrido[3,4-d][1,2,4]triazolo[4,3-b]pyridazine,
6-[4-(1-cyclobutylpiperidin-4-yloxy)phenyl]-3-methylpyrido[3,4-d][1,2,4]triazolo[4,3-b]pyridazine,
6-[4-(1-cyclopentylpiperidin-4-yloxy)phenyl]-3-methylpyrido[3,4-d][1,2,4]triazolo[4,3-b]pyridazine,
3-methyl-6-[4-(3-pyrrolidin-1-ylpropoxy)-phenyl]-pyrido[3,2-d][1,2,4]triazolo[4,3-b]pyridazine,
3-methyl-6-[4-(3-pyrrolidin-1-ylpropoxy)-phenyl]-pyrido[2,3-d][1,2,4]triazolo[4,3-b]pyridazine,
3-methyl-6-(4-{3-[(3S)-3-methylpiperidin-1-yl]propoxy}-phenyl]-pyrido[3,2-d][1,2,4]triazolo[4,3-b]pyridazine,
3-methyl-6-(4-{3-[(3S)-3-methylpiperidin-1-yl]propoxy}-phenyl]-pyrido[2,3-d][1,2,4]triazolo[4,3-b]pyridazine,
3-methyl-6-(4-{3-[(2R)-3-methylpyrrolidin-1-yl]propoxy}-phenyl]-pyrido[3,2-d][1,2,4]triazolo[4,3-b]pyridazine,
3-methyl-6-(4-{3-[(2R)-3-methylpyrrolidin-1-yl]propoxy}-phenyl]-pyrido[2,3-d][1,2,4]triazolo[4,3-b]pyridazine,
6-[4-(1-isopropylpiperidin-4-yloxy)phenyl]-3-methylpyrido[3,2-d][1,2,4]triazolo[4,3-b]pyridazine,
6-[4-(1-isopropylpiperidin-4-yloxy)phenyl]-3-methylpyrido[2,3-d][1,2,4]triazolo[4,3-b]pyridazine,
6-[4-(1-cyclobutylpiperidin-4-yloxy)phenyl]-3-methylpyrido[3,2-d][1,2,4]triazolo[4,3-b]pyridazine,
6-[4-(1-cyclobutylpiperidin-4-yloxy)phenyl]-3-methylpyrido[2,3-d][1,2,4]triazolo[4,3-b]pyridazine,
6-[4-(1-cyclopentylpiperidin-4-yloxy)phenyl]-3-methylpyrido[3,2-d][1,2,4]triazolo[4,3-b]pyridazine,
6-[4-(1-cyclopentylpiperidin-4-yloxy)phenyl]-3-methylpyrido[2,3-d][1,2,4]triazolo[4,3-b]pyridazine,
6-[4-(1-isopropylpiperidin-4-yloxy)phenyl]pyrido[3,2-d][1,2,4]triazolo[4,3-b]pyridazine,
6-[4-(1-isopropylpiperidin-4-yloxy)phenyl]pyrido[2,3-d][1,2,4]triazolo[4,3-b]pyridazine,
6-[4-(1-cyclobutylpiperidin-4-yloxy)phenyl]pyrido[3,2-d][1,2,4]triazolo[4,3-b]pyridazine,
6-[4-(1-cyclobutylpiperidin-4-yloxy)phenyl]pyrido[2,3-d][1,2,4]triazolo[4,3-b]pyridazine,
6-[4-(1-cyclopentylpiperidin-4-yloxy)phenyl]pyrido[3,2-d][1,2,4]triazolo[4,3-b]pyridazine,
6-[4-(1-cyclopentylpiperidin-4-yloxy)phenyl]pyrido[2,3-d][1,2,4]triazolo[4,3-b]pyridazine,
6-[6-(3-piperidin-1-ylpropoxy)pyridin-3-yl]-[1,2,4]triazolo[3,4-a]phthalazine, and
6-{6-[(3S)-3-piperidin-1-ylpropoxy]pyridin-3-yl}-[1,2,4]triazolo[3,4-a]phthalazine,
or a pharmaceutically acceptable salt thereof.

17. A pharmaceutical composition which comprises the compound of claim 1 or a pharmaceutically acceptable salt thereof and a pharmaceutically acceptable carrier.

18. A pharmaceutical composition which comprises the compound of claim 10 or a pharmaceutically acceptable salt thereof and a pharmaceutically acceptable carrier.

19. A pharmaceutical composition which comprises the compound of claim 16 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 7,645,756 B2
APPLICATION NO. : 10/589832
DATED : January 12, 2010
INVENTOR(S) : Takahashi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 503 days.

Signed and Sealed this

Sixteenth Day of November, 2010

David J. Kappos
*Director of the United States Patent and Trademark Office*